US011178893B1

(12) United States Patent
Nordahl

(10) Patent No.: US 11,178,893 B1
(45) Date of Patent: *Nov. 23, 2021

(54) PACKAGED FROZEN ICE POPS OF CANNABIS JUICE PURÉE

(71) Applicant: Jeff Nordahl, Soquel, CA (US)

(72) Inventor: Jeff Nordahl, Soquel, CA (US)

( * ) Notice: Subject to any disclaimer, the term of this patent is extended or adjusted under 35 U.S.C. 154(b) by 35 days.

This patent is subject to a terminal disclaimer.

(21) Appl. No.: 15/965,975

(22) Filed: Apr. 30, 2018

Related U.S. Application Data

(63) Continuation of application No. 15/213,349, filed on Jul. 18, 2016, now Pat. No. 9,955,716.

(60) Provisional application No. 62/292,732, filed on Feb. 8, 2016.

(51) Int. Cl.
| | | |
|---|---|---|
| *A23L 19/00* | (2016.01) | |
| *B65D 85/00* | (2006.01) | |
| *A61K 31/352* | (2006.01) | |
| *A61K 31/192* | (2006.01) | |
| *A61K 9/00* | (2006.01) | |
| *A61K 36/185* | (2006.01) | |

(52) U.S. Cl.
CPC ............ *A23L 19/09* (2016.08); *A61K 9/0095* (2013.01); *A61K 31/192* (2013.01); *A61K 31/352* (2013.01); *A61K 36/185* (2013.01); *B65D 85/00* (2013.01); *A23V 2002/00* (2013.01); *A61K 2236/15* (2013.01)

(58) Field of Classification Search
CPC .. A61K 9/0095; A61K 31/192; A61K 31/352; A61K 36/185; A61K 2236/15; B65D 85/00; A23V 2002/00
USPC ........................... 426/86, 100, 615, 565, 524
See application file for complete search history.

(56) References Cited

U.S. PATENT DOCUMENTS

| | | | |
|---|---|---|---|
| 1,933,596 A | 11/1933 | Maclean | 206/804 |
| 2,157,476 A | 5/1939 | Brodesser | 206/525 |
| 2,248,963 A | 7/1941 | Copeman | 206/457 |
| 3,417,862 A | 12/1968 | Fong | 206/517 |
| 4,452,823 A | 6/1984 | Connolly et al. | 426/115 |
| 5,232,726 A | 8/1993 | Clark et al. | 426/519 |
| 6,231,904 B1 | 5/2001 | Mueller | 426/112 |
| 7,906,160 B2 | 3/2011 | Sherwood | 426/74 |
| 9,044,390 B1 | 6/2015 | Speier | |
| 9,050,631 B2 | 6/2015 | Raichart | |
| 9,066,910 B2 | 6/2015 | Rosenblatt et al. | |
| 9,078,838 B2 | 7/2015 | Andre et al. | |
| 9,095,544 B2 | 8/2015 | Karle et al. | |
| 9,095,563 B2 | 8/2015 | Sekura et al. | |
| 9,149,499 B1 | 10/2015 | Robinson | |
| 9,155,767 B2 | 10/2015 | Hospodor et al. | |
| 9,186,386 B2 | 11/2015 | Speier | |
| 9,205,063 B2 | 12/2015 | Guy et al. | |
| 9,220,294 B2 | 12/2015 | McCullough | |
| 9,277,763 B2 | 3/2016 | Beckman et al. | |
| 9,955,716 B1 * | 5/2018 | Nordahl | A23L 19/09 |
| 9,956,173 B1 * | 5/2018 | Nordahl | A61K 31/192 |
| 9,956,174 B1 * | 5/2018 | Nordahl | B65D 85/00 |
| 2007/0275131 A1 | 11/2007 | Bertini et al. | 426/115 |

OTHER PUBLICATIONS

"Dr. Courtney's raw cannabis juice", located at: https://www.alchimiaweb.com/blogen/dr-courtneys-raw-cannabis-juice/, downloaded on Jul. 13, 2016 (15 pages).
"Ohana Farms CBD Cubes", located at: http://www.ohanaedu.org/index.php/products/cbd-cubes/, downloaded on Jul. 18, 2016 (1 page).
"Cannabis Juice: The Elixir of Health", located at: http://www.cannabis.info/gb/abc/10003309-cannabis-juice-the-elixir-of-health, downloaded on Oct. 26, 2016 (5 pages).
"Juicing Raw Cannabis", by Martin A. Lee, O'Shaughnessy's, Winter/Spring 2013 (1 page).
"Juicing Cannabis: The Potential Health Benefits of Treating Cannabis Like a Vegetable", by Zack Reichard, Jan. 19, 2013 (4 pages).
"Cannabis: Drink Your Medicine! A Poor Man's Guide to Juicing", by Sharon Letts, Apr. 19, 2013 (24 pages).
"Cannabinoid Blend Calculator", located at: https://lift.co/cannabinoid-calculator/, downloaded on Dec. 16, 2016 (1 page).

(Continued)

*Primary Examiner* — Leslie A Wong
(74) *Attorney, Agent, or Firm* — Adibi IP Group, PC; Amir V. Adibi; Andrew C. Palmer

(57) ABSTRACT

A method of manufacturing and packaging frozen ice pops of cannabis juice purée involves collecting raw cannabis material. Next, raw cannabis material is blended with water, fruit juice, or vegetable juice and a sweetening or flavoring agent to form cannabis juice purée. Decarboxylated or non-decarboxylated high concentrate cannabis extract or decarboxylated cannabis infusion is optionally added to the purée. Next, the purée is poured into a tube shaped plastic container. Next, the container is frozen to obtain a packaged frozen ice pop of cannabis juice purée. The cannabis ice pop is provided singularly or in a package having additional cannabis ice pops. A dispensary can store the ice pops until distribution. The package includes labeling describing amounts and types of cannabinoids in the cannabis ice pops. In one example, the cannabis ice pop is non-psychoactive and includes no decarboxylated cannabinoids. In another example, the cannabis ice pop includes decarboxylated cannabinoids.

16 Claims, 52 Drawing Sheets

(56) References Cited

OTHER PUBLICATIONS

"Should You Be Adding Raw Cannabis to Your Smoothie? Some Medical Doctors Say, 'Yes'", located at www.GarmaOnHealth.com, Jun. 14, 2014.
"How Exactly Does Cannabis Juice Work?", Seshata, Oct. 2014.

* cited by examiner

MANUFACTURING AND PACKAGING FROZEN STRUCTURES OF CANNABIS JUICE PURÉE
(FIRST EMBODIMENT)

COLLECTING RAW CANNABIS MATERIAL

FORMING A CANNABIS JUICE PURÉE

DEPOSITING THE CANNABIS JUICE PURÉE
INTO MOLDS OF A TRAY

FREEZING THE TRAY OF MOLDS HAVING THE CANNABIS JUICE PURÉE

PACKAGING THE FROZEN STRUCTURES
INTO A PACKAGE

PACKAGE WITH FROZEN STRUCTURES OF
CANNABIS JUICE PURÉE HAVING NON-
DECARBOXYLATED CANNABINOIDS

PACKAGE WITH FROZEN STRUCTURES OF CANNABIS JUICE PURÉE HAVING NON-DECARBOXYLATED CANNABINOIDS (SIDE VIEW)

PACKAGE WITH FROZEN STRUCTURES OF CANNABIS JUICE PURÉE HAVING NON-DECARBOXYLATED CANNABINOIDS (TOP VIEW)

FROZEN STRUCTURES OF CANNABIS JUICE PURÉE
HAVING NON-DECARBOXYLATED CANNABINOIDS

FROZEN STRUCTURES OF CANNABIS JUICE PURÉE
HAVING NON-DECARBOXYLATED CANNABINOIDS
WITH ADDED NON-DECARBOXYLATED HIGH
CONCENTRATE CANNABIS EXTRACT (ALTERNATE EMBODIMENT)

| PRODUCTS OBTAINED FROM CANNABIS PLANT ||
|---|---|
| NON-CANNABINOID COMPONENTS | CANNABINOID COMPONENTS |
| - TERPENES<br>- FATTY ACIDS<br>- AMINOACIDS<br>- ENZYMES<br>- VITAMINS<br>- MINERALS<br>- CAROTENOIDS<br>- CHLOROPHYLL<br>- FLAVONOIDS<br>- DIETARY FIBERS | - CANNABIGEROLIC ACID (CBGA)<br>- CANNABIGEROVARIN ACID (CBGVA)<br>- TETRAHYDROCANNABINOLIC ACID (THCA)<br>- TETRAHYDROCANNABIVARIN CARBOXYLIC ACID (THCVA)<br>- CANNADIDIOLIC ACID (CBDA)<br>- CANNABIDIVARIN ACID (CBDVA)<br>- CANNABICHROME CARBOXYLIC ACID (CBCA)<br>- CANNABICHROME VARINIC ACID (CBCVA)<br>- TETRAHYDROCANNABINOL (THC)<br>- TETRAHYDROCANNABIDIVARIN (THCV)<br>- TETRAHYDROCANNABIVARIN ACID (THVA)<br>- CANNABIDIOL (CBD)<br>- CANNABIDIVARIN (CBDV)<br>- CANNABICHROMENE (CBC)<br>- CANNABICHROMEVARIN (CBCV)<br>- CANNABIGEROL (CBG)<br>- CANNABIGEROVARIN (CBGV)<br>- CANNABINEROLIC ACID (CBNA)<br>- CANNABIGEROVARINIC ACID (CBNVA)<br>- CANNABINOL (CBN)<br>- CANNABICYCLOL (CBL)<br>- CANNABICYCLOL ACID (CBLA) |

NON-CANNABINOID AND CANNABINOID COMPONENTS MAY BE ADDED TO OR EXCLUDED FROM CANNABIS JUICE PURÉE

PRODUCTS OBTAINED FROM CANNABIS PLANT

FIG. 10D

| TYPE | STRUCTURAL FORMULA | |
|---|---|---|
| TETRAHYDROCANNABINOLIC ACID (THCa) | 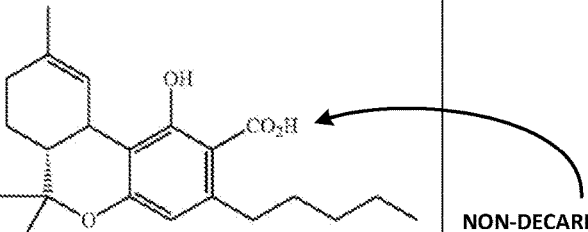 | NON-DECARBOXYLATED TYPES HAVE CARBOXYL GROUP |
| CANNABIDIOLIC ACID (CBDa) | 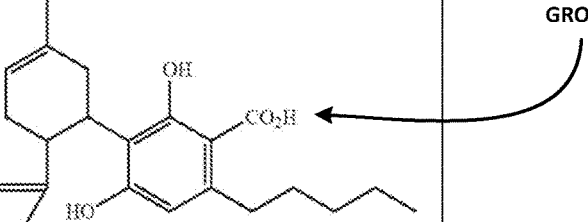 | |
EXAMPLES OF NON-DECARBOXYLATED CANNABINOIDS
FIG. 11

MANUFACTURING AND PACKAGING FROZEN STRUCTURES OF CANNABIS JUICE PURÉE WITH NON-DECARBOXYLATED AND DECARBOXYLATED CANNABINOIDS (SECOND EMBODIMENT)

COLLECTING RAW CANNABIS MATERIAL

FORMING A CANNABIS JUICE PURÉE

FORMING A DECARBOXYLATED CANNABIS
INFUSION INVOLVING OIL

DEPOSITING THE NON-DECARBOXYLATED CANNABIS JUICE PURÉE AND THE DECARBOXYLATED CANNABIS INFUSION INTO MOLDS OF A TRAY

FREEZING THE TRAY OF MOLDS

PACKAGING THE FROZEN STRUCTURES INTO A PACKAGE

PACKAGE WITH FROZEN STRUCTURES OF CANNABIS JUICE PURÉE HAVING NON-DECARBOXYLATED AND DECARBOXYLATED CANNABINOIDS

PACKAGE WITH FROZEN STRUCTURES OF CANNABIS JUICE PURÉE HAVING NON-DECARBOXYLATED AND DECARBOXYLATED CANNABINOIDS (SIDE VIEW)

PACKAGE WITH FROZEN STRUCTURES OF CANNABIS JUICE PURÉE HAVING NON-DECARBOXYLATED AND DECARBOXYLATED CANNABINOIDS (TOP VIEW)

FROZEN STRUCTURES OF NON-DECARBOXYLATED CANNABIS JUICE PURÉE WITH ADDED DECARBOXYLATED CANNABIS INFUSION

FROZEN STRUCTURES OF NON-DECARBOXYLATED CANNABIS JUICE PURÉE WITH ADDED DECARBOXYLATED CANNABIS INFUSION AND NON-DECARBOXYLATED HIGH CONCENTRATE CANNABIS EXTRACT
(ALTERNATE EMBODIMENT)

FROZEN STRUCTURES OF NON-DECARBOXYLATED CANNABIS JUICE PURÉE WITH ADDED DECARBOXYLATED HIGH CONCENTRATE CANNABIS EXTRACT
(ALTERNATE EMBODIMENT)

FROZEN STRUCTURES OF NON-DECARBOXYLATED CANNABIS JUICE PURÉE WITH ADDED NON-DECARBOXYLATED AND DECARBOXYLATED HIGH CONCENTRATE CANNABIS EXTRACT

(ALTERNATE EMBODIMENT)

EXAMPLES OF DECARBOXYLATED
CANNABINOIDS

STORING PACKAGED STRUCTURES OF FROZEN CANNABIS JUICE PURÉE HAVING NON-DECARBOXYLATED AND DECARBOXYLATED CANNABINOIDS

CUBE-SHAPED MOLD TRAY
(PERSPECTIVE VIEW)

CUBE SHAPED
MOLD TRAY
(TOP VIEW)

CYLINDRICAL SHAPED
MOLD TRAY
(TOP VIEW)

RECTANGULAR
SHAPED MOLD TRAY
(TOP VIEW)

HEXAGONAL SHAPED
MOLD TRAY
(TOP VIEW)

TRIANGULAR-SHAPED
MOLD TRAY
(TOP VIEW)

STAR-SHAPED MOLD
TRAY
(TOP VIEW)

TRAPEZOIDAL-
SHAPED MOLD TRAY
(TOP VIEW)

CONCAVE-SHAPED
MOLD TRAY
(TOP VIEW)

PARALLELOGRAM-
SHAPED MOLD TRAY
(TOP VIEW)

LEAF-SHAPED MOLD TRAY
(TOP VIEW)

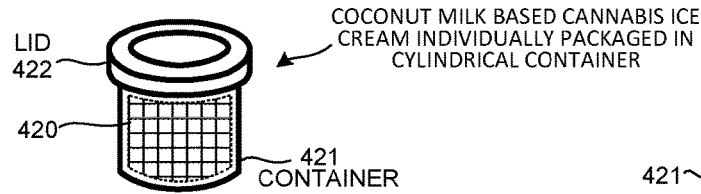
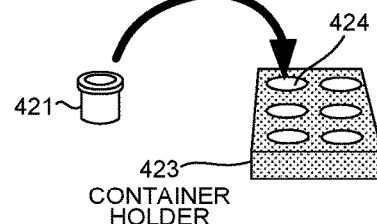

COCONUT MILK BASED CANNABIS ICE CREAM PACK

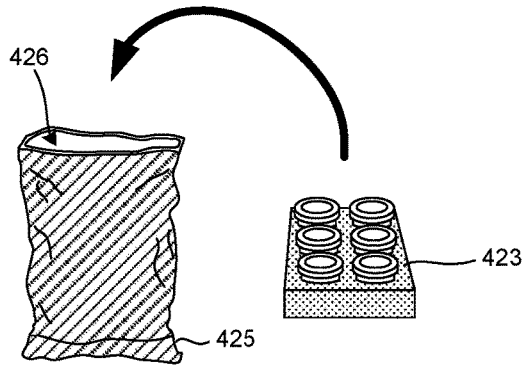
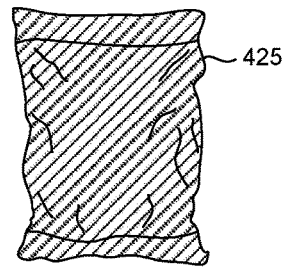

FIG. 39

PACKAGED COCONUT MILK BASED CANNABIS ICE CREAM PACKS

FIG. 40

| | STORAGE CAPACITY | PACKAGING COSTS | WASTE GENERATION | QUANTITY PER PACKAGE |
|---|---|---|---|---|
| NOVEL PACKAGE WITH PELLETS (FIGS. 7 AND 19) | MINIMAL  PACKAGES SAME SHAPE STACKING EFFICIENTLY | MINIMAL  VACUUM SEAL PELLETS IN BAG | MINIMAL  ONLY WASTE IS VACUUM SEAL BAG | 20 PELLETS |
| CONVENTIONAL PACKAGE WITH COCONUT MILK BASED CANNABIS ICE CREAM PACKS (FIG. 40) | SIGNIFICANT SPACE REQUIRED  PACKAGE HAS OBTUSE SHAPE | SUBSTANTIAL PACKAGING COSTS  1) PACK EACH ICE CREAM IN INDIVIDUAL CONTAINER 2) MATERIAL COSTS FOR CONTAINERS, LIDS, HOLDER, AND OUTER PACKAGE | ADDITIONAL WASTE  1) 6 CONTAINERS 2) 6 LIDS 3) HOLDER 4) OUTER PACKAGE | 6 CANNABIS ICE CREAMS |

FIG. 41

MANUFACTURING AND PACKAGING
FROZEN ICE POPS OF CANNABIS JUICE PURÉE
(THIRD EMBODIMENT)

DEPOSITING THE CANNABIS JUICE PURÉE
INTO A CONTAINER

FREEZING THE CONTAINER TO FORM A PACKAGED
FROZEN ICE POP OF CANNABIS JUICE PURÉE

PACKAGED FROZEN ICE POP OF
CANNABIS JUICE PURÉE
(WITHOUT DECARBOXYLATED CANNABINOIDS)

PACKAGED FROZEN ICE POP OF CANNABIS JUICE PURÉE WITH ADDED NON-DECARBOXYLATED HIGH CONCENTRATE CANNABIS EXTRACT (ALTERNATE EMBODIMENT)

PACKAGED FROZEN ICE POP OF CANNABIS JUICE PURÉE WITH ADDED DECARBOXYLATED CANNABIS INFUSION
(WITH DECARBOXYLATED CANNABINOIDS)

PRE-DETERMINED AMOUNT OF CANNABINOIDS IN EACH ICE POP

FROM RAW CANNABIS PLANT:

| | |
|---|---|
| THCa | 30 mg / 3 fl. oz. |
| CBDa | 45 mg / 3 fl. oz. |
| TOTAL FROM RAW CANNABIS: | 75 mg / 3 fl. oz. |

FROM DECARBOXYLATED CANNABIS INFUSION:

| | |
|---|---|
| THC | 5 mg / 3 fl. oz. |
| CBD | 90 mg / 3 fl. oz. |
| TOTAL FROM DECARB. CANNABIS INFUSION: | 95 mg / 3 fl. oz. |

FROM NON-DECARBOXYLATED HIGH CONCENTRATE CANNABIS EXTRACT (KIEF):

| | |
|---|---|
| THCa | 600 mg / 3 fl. oz. |
| CBDa | 900 mg / 3 fl. oz. |
| TOTAL FROM NON-DECARB. KIEF: | 1,500 mg / 3 fl. oz. |

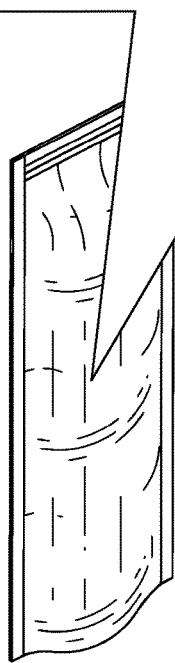

PACKAGED FROZEN ICE POP OF CANNABIS JUICE PURÉE WITH ADDED DECARBOXYLATED CANNABIS INFUSION AND NON-DECARBOXYLATED HIGH CONCENTRATE CANNABIS EXTRACT
(ALTERNATE EMBODIMENT)

FIG. 46B

PACKAGED FROZEN ICE POP OF CANNABIS JUICE PURÉE WITH ADDED DECARBOXYLATED HIGH CONCENTRATE CANNABIS EXTRACT (ALTERNATE EMBODIMENT)

PRE-DETERMINED AMOUNT OF CANNABINOIDS IN EACH ICE POP

| FROM RAW CANNABIS PLANT: | | FROM DECARBOXYLATED HIGH CONCENTRATE CANNABIS EXTRACT (KIEF): | | FROM NON-DECARBOXYLATED HIGH CONCENTRATE CANNABIS EXTRACT (KIEF): | |
|---|---|---|---|---|---|
| THCa | 30 mg / 3 fl. oz. | THC | 10 mg / 3 fl. oz. | THCa | 600 mg / 3 fl. oz. |
| CBDa | 45 mg / 3 fl. oz. | CBD | 300 mg / 3 fl. oz. | CBDa | 900 mg / 3 fl. oz. |
| TOTAL FROM RAW CANNABIS: | 75 mg / 3 fl. oz. | TOTAL FROM DECARB. KIEF: | 310 mg / 3 fl. oz. | TOTAL FROM NON-DECARB. KIEF: | 1,500 mg / 3 fl. oz. |

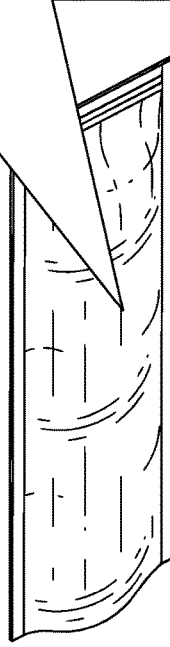

PACKAGED FROZEN ICE POP OF CANNABIS JUICE PURÉE WITH ADDED NON-DECARBOXYLATED AND DECARBOXYLATED HIGH CONCENTRATE CANNABIS EXTRACT (ALTERNATE EMBODIMENT)

FIG. 46D

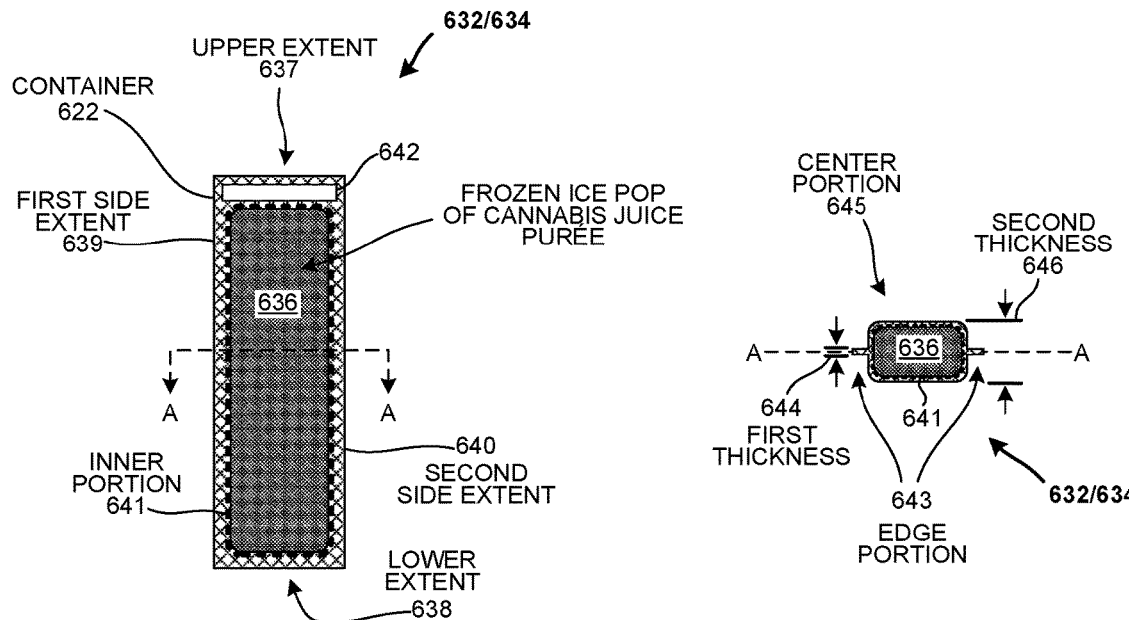
SIDE VIEW OF PACKAGED FROZEN ICE POP OF CANNABIS JUICE PURÉE
FIG. 48
TOP VIEW OF PACKAGED FROZEN ICE POP OF CANNABIS JUICE PURÉE
FIG. 49
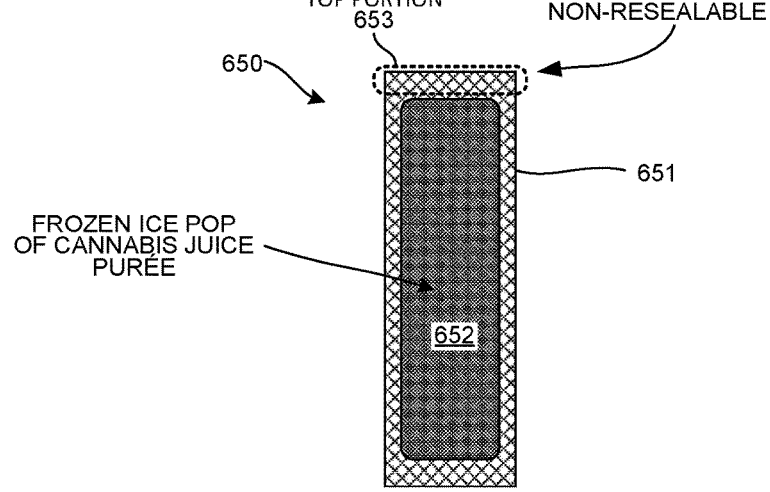
SIDE VIEW OF PACKAGED FROZEN ICE POP OF CANNABIS JUICE PURÉE
(ANOTHER EMBODIMENT)
FIG. 50

PACKAGING THE PLURALITY OF PACKAGED
FROZEN ICE POPS OF CANNABIS JUICE PURÉE

STORING PACKAGES HAVING THE PACKAGED
FROZEN ICE POPS OF CANNABIS JUICE PURÉE

MANUFACTURING AND PACKAGING
CANNABIS JUICE PURÉE
(FOURTH EMBODIMENT)

DEPOSITING THE CANNABIS JUICE PURÉE
INTO A CONTAINER

PACKAGING THE PLURALITY OF CONTAINERS HAVING THE CANNABIS JUICE PURÉE

PACKAGED CANNABIS JUICE PURÉE
(WITHOUT DECARBOXYLATED CANNABINOIDS)

PRE-DETERMINED AMOUNT OF CANNABINOIDS IN EACH CONTAINER

FROM RAW CANNABIS PLANT:

| THCa | 120 mg / 12 fl. oz. |
|---|---|
| CBDa | 180 mg / 12 fl. oz. |
| TOTAL FROM RAW CANNABIS: | 300 mg / 12 fl. oz. |

FROM NON-DECARBOXYLATED HIGH CONCENTRATE CANNABIS EXTRACT (KIEF):

| THCa | 2,400 mg / 12 fl. oz. |
|---|---|
| CBDa | 3,600 mg / 12 fl. oz. |
| TOTAL FROM NON-DECARB. KIEF: | 6,000 mg / 12 fl. oz. |

PACKAGED CANNABIS JUICE PURÉE WITH ADDED NON-DECARBOXYLATED HIGH CONCENTRATE CANNABIS EXTRACT (ALTERNATE EMBODIMENT)

FIG. 58B

PACKAGED CANNABIS JUICE PURÉE WITH ADDED DECARBOXYLATED CANNABIS INFUSION

PRE-DETERMINED AMOUNT OF CANNABINOIDS IN EACH CONTAINER

FROM RAW CANNABIS PLANT:

| THCa | 120 mg / 12 fl. oz. |
|---|---|
| CBDa | 180 mg / 12 fl. oz. |
| TOTAL FROM RAW CANNABIS: | 300 mg / 3 fl. oz. |

FROM DECARBOXYLATED CANNABIS INFUSION:

| THC | 10 mg / 12 fl. oz. |
|---|---|
| CBD | 270 mg / 12 fl. oz. |
| TOTAL FROM DECARB. CANNABIS INFUSION: | 280 mg / 12 fl. oz. |

FROM NON-DECARBOXYLATED HIGH CONCENTRATE CANNABIS EXTRACT (KIEF):

| THCa | 2,400 mg / 12 fl. oz. |
|---|---|
| CBDa | 3,600 mg / 12 fl. oz. |
| TOTAL FROM NON-DECARB. KIEF: | 6,000 mg / 12 fl. oz. |

PACKAGED CANNABIS JUICE PURÉE WITH ADDED DECARBOXYLATED CANNABIS INFUSION AND NON-DECARBOXYLATED HIGH CONCENTRATE CANNABIS EXTRACT (ALTERNATE EMBODIMENT)

FIG. 59B

| PRE-DETERMINED AMOUNT OF CANNABINOIDS IN EACH CONTAINER ||||
| FROM RAW CANNABIS PLANT: | | FROM DECARBOXYLATED HIGH CONCENTRATE CANNABIS EXTRACT (KIEF): | |
| THCa | 120 mg / 12 fl. oz. | THC | 10 mg / 12 fl. oz. |
| CBDa | 180 mg / 12 fl. oz. | CBD | 300 mg / 12 fl. oz. |
| TOTAL FROM RAW CANNABIS: | 300 mg / 12 fl. oz. | TOTAL FROM DECARB. KIEF: | 310 mg / 12 fl. oz. |

PACKAGED CANNABIS JUICE PURÉE WITH ADDED DECARBOXYLATED HIGH CONCENTRATE CANNABIS EXTRACT (ALTERNATE EMBODIMENT)

FIG. 59C

PRE-DETERMINED AMOUNT OF CANNABINOIDS IN EACH CONTAINER

| FROM RAW CANNABIS PLANT: | | FROM DECARBOXYLATED HIGH CONCENTRATE CANNABIS EXTRACT (KIEF): | | FROM NON-DECARBOXYLATED HIGH CONCENTRATE CANNABIS EXTRACT (KIEF): | |
|---|---|---|---|---|---|
| THCa | 120 mg / 12 fl. oz. | THC | 10 mg / 12 fl. oz. | THCa | 2,400 mg / 12 fl. oz. |
| CBDa | 180 mg / 12 fl. oz. | CBD | 300 mg / 12 fl. oz. | CBDa | 3,600 mg / 12 fl. oz. |
| TOTAL FROM RAW CANNABIS: | 300 mg / 3 fl. oz. | TOTAL FROM DECARB. KIEF: | 310 mg / 12 fl. oz. | TOTAL FROM NON-DECARB. KIEF: | 6,000 mg / 12 fl. oz. |

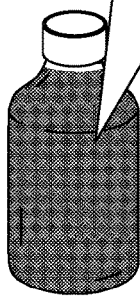

PACKAGED CANNABIS JUICE PURÉE WITH ADDED
NON-DECARBOXYLATED AND DECARBOXYLATED
HIGH CONCENTRATE CANNABIS EXTRACT (ALTERNATE EMBODIMENT)

FIG. 59D

STORING PACKAGED CONTAINERS WITH CANNABIS JUICE PURÉE

| 1100 | THC | CBD | CBG | CBN | CBC | THCV | THCA | CBDA |
|---|---|---|---|---|---|---|---|---|
| PAIN RELIEF | X | X |  | X | X |  |  |  |
| APPETITE/ WEIGHT LOSS |  |  |  |  |  | X |  |  |
| SUPPRESS BACTERIAL GROWTH |  | X | X |  |  |  |  |  |
| REDUCE BLOOD SUGAR |  | X | X |  |  |  |  |  |
| REDUCE SEIZURES |  | X |  |  |  | X |  |  |
| REDUCE INFLAMMATION |  | X | X |  | X |  | X | X |
| AIDS SLEEP |  |  |  | X |  |  |  |  |
| REDUCE RISK OF ARTERY BLOCKAGE |  |  | X |  |  |  |  |  |
| INHIBIT TUMOR/ CANCER CELL GROWTH |  | X | X |  | X |  | X | X |
| TREATS PSORIASIS |  | X |  |  |  |  |  |  |
| TRANQUILIZING/ MANAGE PSYCHOSIS |  | X |  |  |  |  |  |  |
| SUPPRESS MUSCLE SPASM | X | X |  | X |  |  | X |  |
| RELIEVE ANXIETY |  | X |  |  |  |  |  |  |
| STIMULATE APPETITE | X |  |  |  |  |  |  |  |
| PROMOTE BONE GROWTH |  | X | X |  | X | X |  |  |
| REDUCE IMMUNE SYS. FUNCTION |  | X |  |  |  |  |  |  |
| PROTECT NERVOUS SYS. DEGENERATION |  | X |  |  |  |  |  |  |

FIG. 62

PACKAGED FROZEN ICE POPS OF CANNABIS JUICE PURÉE

CROSS REFERENCE TO RELATED APPLICATIONS

This application is a continuation of, and claims the benefit under 35 U.S.C. § 120 from, nonprovisional U.S. patent application Ser. No. 15/213,349, entitled "Packaged Frozen Ice Pops Of Cannabis Juice Puree," filed on Jul. 18, 2016, now U.S. Pat. No. 9,955,716. U.S. patent application Ser. No. 15/213,349 claims the benefit under 35 U.S.C. § 119 of U.S. provisional patent application Ser. No. 62/292,732, entitled "Dietary Supplement and Method of Production," filed on Feb. 8, 2016. The subject matter of each of the foregoing documents is expressly incorporated herein by reference.

TECHNICAL FIELD

The present disclosure relates generally to methods for manufacturing and packaging dietary supplements, and more particularly to manufacturing and packaging cannabinoid products.

BACKGROUND INFORMATION

The cannabis plant genus is known to produce over four hundred and eighty different chemical substances, and at least eighty of these chemical substances are classified as cannabinoids. Many cannabinoids have been found to have diverse medicinal uses which include analgesic, anti-inflammatory, anticancer, antibioitic, anti-anxiety, and anti-oxidant properties. There are now thousands of strains of the cannabis plant that have evolved naturally or have been developed through hybridization. The different strains of cannabis tend to contain different combinations of these cannabinoids in varying amounts.

Cannabinoids found in their natural state typically are in a non-decarboxylated form. Cannabinoids can be converted into a decarboxylated form by a process referred to as decarboxylation. Decarboxylation is a chemical reaction that removes the carboxyl group from a compound. In the case of cannabinoids, decarboxylation involves removing the carboxyl group from the cannabinoid compounds. One common technique for performing decarboxylation is by heating cannabis material to 240° F. or higher for ten minutes to a few hours. Decarboxylation also occurs in cannabis material if the material is allowed to be dry cured. These cannabinoids provide different medicinal benefits when they are in their 'raw' or non-decarboxylated form, compared to their properties after they are decarboxylated.

Two cannabinoids that show tremendous medicinal potential are tetrahydrocannabinol (THC) and cannabidiol (CBD). THC is the decarboxylated cannabinoid that is considered to be psychoactive. However, if the cannabis material is never heated, 'decarboxylated', the cannabinoid will remain in its acid form, tetrahydrocannabinolic acid (THCa). THCa is not considered to be psychoactive. THCa also provides many medicinal benefits without causing psychoactive effects for the user. Most notably, THCa has many anti-inflammatory and cancer cell fighting properties while not being psychoactive. The cannabinoid CBD also is present in the acid form, cannabidiolic acid (CBDa), if the raw cannabis material is not decarboxylated. But when decarboxylated, the CBDa is converted to CBD. Both CBDa and CBD have a different set of medicinal properties.

Because decarboxylation occurs when the cannabis material is dried or heated, it is challenging to find methods for consumers to have access to the 'raw' non-decarboxylated cannabis material. Raw cannabis leaves and flowers will begin to spoil or decarboxylate after a few days of being removed from the living plant. As a result, commercial distribution of raw non-decarboxylated cannabis material has been commercially unfeasible. A solution that overcomes these challenges is desired.

SUMMARY

Methods of manufacturing, packaging, and storing cannabis products are provided. In one embodiment, a plurality of frozen structures of cannabis juice purée that comprises a pre-determined amount of non-decarboxylated cannabinoids is packaged and stored. In one example, the frozen structures of cannabis juice purée are frozen cubes of cannabis juice purée. The frozen cubes are also referred to as "frozen cannabis juice purée cubes" or "cubes" due to their cubic shape. The frozen structures of cannabis juice purée can be made to form shapes other than cubic shaped structures. The frozen cannabis juice purée cubes are administered to individuals desiring the pre-determined amount of non-decarboxylated cannabinoids. A user can combine the frozen cannabis juice purée cubes with other juices, fruits, vegetables, or supplements for consumption, for example, by adding a desired number of the cubes to a "smoothie" blend. The frozen cannabis juice purée cubes do not include any decarboxylated cannabinoids. Decarboxylated cannabinoids are formed by heating raw cannabis material thereby converting THCa to THC. THC may have psychoactive properties. Because the non-decarboxylated frozen cannabis juice purée cubes do not include such decarboxylated cannabinoids, the frozen cannabis juice purée cubes are generally non-psychoactive. Thus, a person can consume the frozen cannabis juice purée cubes and obtain therapeutic benefits while still retaining his/her faculties to perform his/her ordinary daily routine.

The non-decarboxylated cannabinoid frozen cannabis juice purée cubes are frozen thereby extending the shelf life of the cannabinoids within the cubes to at least six months. In conventional techniques used to collect and store non-decarboxylated cannabinoid material, the non-decarboxylated cannabinoid material lasts only between two and three days before spoiling. Due to the known shelf life limitations, packaging and distributing the non-decarboxylated cannabinoid material is not practical or commercially feasible. Unfortunately, individuals who require the non-decarboxylated cannabinoids for treating illnesses or health conditions do not have ready access to a consistent supply of non-decarboxylated cannabinoids, especially cannabis material which contains the optimal levels and ratios of cannabinoids. The novel packaged frozen cannabis juice purée cubes overcome this shortcoming by extending shelf life resulting in consistent and reliable access to cannabinoids in specific dosage amounts for individuals who require the cannabinoids to treat various medical conditions and to live more comfortably than they would be able to otherwise.

In a first step, raw cannabis material is collected by trimming leaves or flowers of a cannabis plant. The raw cannabis material includes leaves, flowers, stems, trichomes, and other plant material from the cannabis plant. The trimmed cannabis material has a particular cannabinoid profile that has desired therapeutic qualities. The cannabinoid profile indicates types and proportions of cannabinoids present in the cannabis material. Different types of cannabis plants exhibit different cannabinoid profiles that are beneficial for certain types of medical conditions. The cannabinoid profile for a specific plant can be determined by a laboratory capable of performing a full spectrum cannabinoid profiling and analysis. Such laboratories often employ High Performance Liquid Chromatography (HPLC/UV) to conduct the analysis.

In one example, the cannabis plant is selected such that the cannabinoid profile has tetrahydrocannabinolic acid (THCa) and cannabidiolic acid (CBDa) such that the THCa to CBDa ratio is 3 CBDa to 2 THCa. This means that for every 3.0 milligrams of CBDa in a unit of cannabis material, there is approximately 2.0 milligrams of THCa. In another example, the cannabis profile is taken from the group consisting of: 2 CBDa to 1 THCa, 1 CBDa to 1 THCa, 1 CBDa to 2 THCa, 1 CBDa to 3 THCa, 3 CBDa to 1 THCa, 0 CBDa to 1 THCa (no CBDa, only THCa), and 1 CBDa to 0 THCa (no THCa, only CBDa).

In a second step, a cannabis juice purée is formed from the collected raw cannabis material by blending the collected raw cannabis material along with water and a thickening agent. The resulting cannabis juice purée has a liquid composition and is also referred to as "a uniform purée" or "a liquefied cannabis juice purée". The water is filtered water, unfiltered water, ice formed from filtered water, or ice formed from unfiltered water. Alternatively, fruit juice or vegetable juice can be used in addition to or instead of water. The thickening agent aids in suspending the cannabis material thereby aiding in a uniform distribution of cannabinoids throughout the cannabis juice purée. A uniform distribution of cannabinoids throughout the cannabis juice purée is desired to ensure that each cube has a consistent dose of cannabinoids. In one example, the variation in amount of cannabinoids in each cube is 10%. Without the thickening agent, the resulting mixture would have an upper layer with the water and a bottom layer with the cannabis material rather than a uniform mixture. The thickening agent may be banana, avocado, psyllium husk, tapioca, or any food-grade thickening agent.

In accordance with one novel aspect, the cannabis juice purée is formed without a juicing process. In a juicing process, a portion of the cannabis plant material is separated from the juice of the cannabis plant. At least part of the separated cannabis plant material is treated as waste and is disposed. To form the cannabis juice purée, however, all of the cannabis plant material is converted into the cannabis juice purée. The resulting cannabis juice purée includes all of the cannabis plant material placed in the blender and all of the extracted cannabis juice that is extracted in the blending process. No waste product is generated in forming the cannabis juice purée. Accordingly, the cannabis juice purée has all of the cannabis plant material and is rich in dietary fibers and non-cannabinoid components that include terpenes, fatty acids, aminoacids, enzymes, vitamins, minerals, carotenoids, chlorophyll, and flavonoids.

In a third step, the cannabis juice purée is deposited into molds of a tray. The tray has a plurality of molds each having a substantially identical size, shape, and volume. Depositing the cannabis juice purée into similar molds results in each cube having a substantially similar amount of cannabinoids. An individual tends to prefer reliable and consistent doses, thus similarly sized cubes with substantially the same cannabinoid profiles are desired. In addition, by using a tray with the same size of molds, the cubes can be effectively mass produced thereby reducing the overall cost of cubes to the consumer.

In a fourth step, the tray of molds having the cannabis juice purée is frozen to form the frozen cannabis juice purée cubes. In one example, the tray having the cannabis juice purée is placed in a freezer having a temperature less than 5.0° F., or alternatively less than 0.0° F. Freezing the cannabis juice purée results in a shelf-life of more than six months if the cubes are properly stored in a freezer. The cannabis juice purée used to form the cubes does not contain any dairy product, milk-based product, or cream type of product, such as coconut milk. The frozen cannabis juice purée cubes are in a solid state and are frozen, solid structures that maintain their structure when placed next to each other. The frozen cannabis juice purée cubes do not have a soft, malleable consistency such as a sorbet-type consistency or ice cream-type consistency.

In a fifth step, the frozen cannabis juice purée cubes having the non-decarboxylated cannabinoids are packaged into a package. The frozen cannabis juice purée cubes are packaged in a vacuum sealed package, a bag, or a container having a detachable lid. A label identifying the contents can be placed onto the outside of the package. No additional packaging material is placed inside the package. The cubes are loosely packed so that they do not touch, or are tightly packed so that each cube contacts at least one other cube. Because the frozen cannabis juice purée cubes are frozen prior to packaging and the purée recipe freezes to a hardness similar to ice (not a soft malleable texture like ice cream or sorbet), the frozen cannabis juice purée cubes can contact each other inside the package without damaging their integrity or dosage amount per cube. Each cube has at least one surface that directly contacts a surface of the package. Each cube is adjacent to at least two other cubes. The cubes within the package consume over 95% of the total volume of package. In addition, the package of cubes has at least two flat surfaces thereby providing optimal storing and transporting characteristics. In another example, the cubes are stacked so that not all of the cubes contact the package.

In accordance with another novel aspect, a plurality of packages having frozen cannabis juice purée cubes with only non-decarboxylated cannabinoids is stored. The packages are stored in a freezer by stacking each package above another package. Each package has at least two flat surfaces due to the uniform size and shape of each cube. Accordingly, the packages stack compactly in the freezer. In one example, a manufacturing entity manufactures and provides the packaged frozen cannabis juice purée cubes with only non-decarboxylated cannabinoids to a dispensary entity. The dispensary entity handles storing the packaged cubes until the packaged cubes are provided to end consumers.

In a second embodiment, the packaged frozen cannabis juice purée cubes comprise non-decarboxylated cannabinoids and decarboxylated cannabinoids. The amount of decarboxylated cannabinoids in each frozen structure is at least 5 mg. A structure with less than 5 mg is not considered to be a therapeutic dose of decarboxylated cannabinoids because consuming less than 5 mg decarboxylated cannabinoids has negligible, if any, effects on the user. The amount of decarboxylated cannabinoids may include one type of decarboxylated cannabinoid (such as CBD) or more than one type of decarboxylated cannabinoid (such as CBD and THC).

The packaged frozen cannabis juice purée cubes with both non-decarboxylated cannabinoids and decarboxylated cannabinoids provides consumers with a full spectrum of THCa, THC, CBDa, CBD, and all of the other cannabis compounds in both the non-decarboxylated and decarboxylated forms, in one easy-to-consume frozen purée cube. The frozen cannabis juice purée cubes include at least one cannabinoid taken from the group consisting of: cannabigerolic acid (CBGa), cannabigerovarin acid (CBGVA), tetrahydrocannabinolic acid (THCA), tetrahydrocannabivarin carboxylic acid (THCVA), cannadidiolic acid (CBDA), cannabidivarin acid (CBDVA), cannabichrome carboxylic acid (CBCA), cannabichrome varinic acid (CBCVA), tetrahydrocannabinol (THC), tetrahydrocannabidivarin (THCV), tetrahydrocannabivarin acid (THVA), cannabidiol (CBD), cannabidivarin (CBDV), cannabichromene (CBC), cannabichromevarin (CBCV), cannabigerol (CBG), cannabigerovarin (CBGV), cannabinerolic acid (CBNA), cannabigerovarinic acid (CBNVA), cannabinol (CBN), cannabicyclol (CBL), and cannabicyclol acid (CBLA).

In a first step, two separate portions of raw cannabis material are collected. The first portion of raw cannabis material may come from a strain of cannabis with a unique cannabinoid ratio (for example, 3 CBDa to 2 THCa). This first portion will remain in its non-decarboxylated state. Other cannabinoid ratios in the first portion include: 2 CBDa to 1 THCa, 1 CBDa to 1 THCa, 1 CBDa to 2 THCa, 1 CBDa to 3 THCa, 3 CBDa to 1 THCa, 0 CBDa to 1 THCa (no CBDa, only THCa), and 1 CBDa to 0 THCa (no THCa, only CBDa). The second portion of cannabis is collected from a different strain of cannabis plant with a different unique cannabinoid profile (for example, 30 CBDa to 1 THCa). This second portion will later be decarboxylated. When this second portion is decarboxylated, the ratio of the decarboxylated cannabinoids becomes 30 CBD to 1 THC. Other cannabinoid ratios in the decarboxylated second portion include: 20 CBD to 1 THC, 10 CBD to 1 THC, or 5 CBD to 1 THC.

In an alternative step, the first portion (non-decarboxylated portion) of raw cannabis material and the second portion (to be decarboxylated) of raw cannabis material are collected from the same strain of cannabis plant with the exact same cannabinoid profile. In one example, the first portion Is 3 CBDa to 2 THCa, and the second portion is also 3 CBDa to 2 THCa. Once decarboxylated, the second portion will convert to a ratio of 3 CBD to 2 THC. Other combinations of cannabinoid materials having different cannabinoid profiles can be selected depending upon the desired therapeutic effects or medical conditions being targeted. An artisan of ordinary skill would appreciate the vast number of combinations of types and amounts of cannabinoids that can be used to create the cubes.

In a second step, a non-decarboxylated cannabis juice purée is formed from the first portion of raw cannabis material and a decarboxylated cannabis infusion is formed from the second portion of raw cannabis material. The non-decarboxylated cannabis juice purée is formed by blending the first portion of collected raw cannabis material along with water and a thickening agent. The decarboxylated cannabis infusion is formed by heating the second portion of collected raw cannabis material. Decarboxylating cannabis material can be achieved through heating the cannabis material at a temperature of 240° F. for 30 minutes or longer in a mixture of fatty oil. Decarboxylating cannabis material can also be achieved through heating the cannabis material in an oven without any oil or substance.

In a third step, the non-decarboxylated cannabis juice purée and the decarboxylated cannabis infusion are deposited into molds of a tray such that each mold has non-decarboxylated and decarboxylated cannabinoids. The non-decarboxylated cannabis juice purée is deposited into each mold to fill approximately half of the mold. Next, the decarboxylated cannabis infusion is deposited at a center location on the top surface of the half-filled mold. Next, the non-decarboxylated cannabis juice purée is deposited above the decarboxylated cannabis infusion to fill the rest of each mold.

Alternatively, the decarboxylated cannabis infusion is deposited into the non-decarboxylated cannabis juice purée during the blending process. By adding the decarboxylated cannabis infusion during the blending process, the decarboxylated cannabinoids are uniformly distributed throughout the cannabis juice purée resulting in a uniform distribution of cannabinoids in each cube after the freezing process.

In a fourth step, the tray of molds having the cannabis juice purée is frozen to form the frozen cannabis juice purée cubes having non-decarboxylated and decarboxylated cannabinoids. The cannabis juice purée used to form the cubes does not contain any dairy product, milk-based product, or cream type of product, such as coconut milk. The tray of molds having the cannabis juice purée is placed in a freezer having a temperature less than 5.0° F., or alternatively less than 0.0° F. Freezing the cannabis juice purée results in an extended shelf-life of at least six months if the frozen cannabis juice purée cubes are properly stored in a freezer. The frozen cannabis juice purée cubes are in a solid state and are frozen, solid structures that maintain their structure when placed next to each other. The frozen cannabis juice purée cubes do not have a soft, malleable consistency such as a sorbet-type consistency or ice cream-type consistency.

In a fifth step, the frozen cannabis juice purée cubes having the non-decarboxylated and decarboxylated cannabinoids are packaged into a package. The frozen cannabis juice purée cubes are packaged in a vacuum sealed package, a bag, or a container having a detachable lid. A label identifying the contents can be placed onto the outside of the package. No additional packaging material is placed inside the package. The cubes are loosely packed so that not all of the cubes contact each other, or are tightly packed so that each cube contacts at least one other cube. Because the frozen cannabis juice purée cubes are frozen prior to packaging and the purée recipe freezes to a hardness similar to ice (not a soft malleable texture like ice cream or sorbet), the frozen cannabis juice purée cubes can contact each other inside the package without damaging their integrity or dosage amount per cube. Each cube has at least one surface that directly contacts a surface of the package. Each cube is adjacent to at least two other cubes. The cubes within the package consume over 95% of the total volume of package. In addition, the package of cubes has at least two flat surfaces thereby providing optimal storing and transporting characteristics. In another example, the cubes are stacked so that not all of the cubes contact the package.

In accordance with another novel aspect, a plurality of packages having frozen cannabis juice purée cubes is stored. The packages are stored in a freezer by stacking each package above another package. Each package has at least two flat surfaces due to the uniform size and shape of each cube. Accordingly, the packages stack compactly in the freezer. In one example, a manufacturing entity manufactures and provides the packaged frozen cannabis juice purée cubes to a dispensary entity. The dispensary entity handles storing the packaged cubes until the packaged cubes are provided to end consumers.

In a third embodiment, a method of manufacturing and packaging frozen ice pops of cannabis juice purée is provided. The resulting packaged frozen ice pops of cannabis juice purée are also referred to as a "frozen cannabis to go pack", "frozen cannabis on the go pop", "frozen cannabis icicle", or "frozen cannabis popsicle". In one specific embodiment, the packaged frozen ice pop of cannabis juice purée has an amount of non-decarboxylated cannabinoids and is non-psychoactive. In another specific embodiment, the packaged frozen ice pop of cannabis juice purée has an amount of non-decarboxylated cannabinoids and an amount of decarboxylated cannabinoids.

In a first step, a cannabis juice purée is formed. To form a packaged frozen ice pop of cannabis juice purée that is non-psychoactive, raw cannabis material having an amount of non-decarboxylated cannabinoids is collected but never heated. The amount of non-decarboxylated cannabinoids is blended together with a thickening agent and a sweetening agent such as honey, stevia, fruit juice, sugar, or corn syrup. The sweetening agent is optional and is not included in some embodiments. Flavoring agents are included in other embodiments, such as fruit flavor or spice (apple, cherry, mint, tart, etc.). Fruit juice, fruit, or vegetable material may also be added, such as blueberries, blueberry juice, carrots, or carrot juice. Non-decarboxylated high concentrate cannabis extract may also be added to the cannabis juice purée prior to freezing to increase the amount of non-decarboxylated cannabinoids in each ice pop.

To form a packaged frozen ice pop of cannabis juice purée that has decarboxylated cannabinoids, a portion of the collected raw cannabis material is heated to obtain an amount of decarboxylated cannabinoids. The amount of decarboxylated cannabinoids are added to the cannabis juice purée prior to freezing. Non-decarboxylated high concentrate cannabis extract, decarboxylated high concentrate cannabis extract, decarboxylated cannabis infusion, or heated cannabis material may also be added to the cannabis juice purée prior to freezing to increase the amount of non-decarboxylated and decarboxylated cannabinoids in each ice pop.

In a second step, the cannabis juice purée is deposited into a container. In one example, the container is a tube shaped container made of a flexible material. The container is a tube shaped container formed from a thermoplastic polymer such as polypropylene plastic resin. In one example, the tube shaped container has a resealable end. In another example, the tube shaped container is not resealable and a user must permanently tear a portion of the container to access the frozen ice pop of cannabis juice purée.

In a third step, the container having the cannabis juice purée is frozen to form a packaged frozen ice pop of cannabis juice purée. The container having the cannabis juice purée is placed in a freezer so that the cannabis juice purée in the container (along with any added cannabis infusion or high concentrate cannabis extract) can freeze. The temperature within the freezer is typically between 0.0° F. and 5.0° F., but may be less than 0.0° F. The resulting frozen ice pop of cannabis juice purée assumes the shape of the container. In one example, packaged frozen ice pop of cannabis juice purée is a cylindrical tube shaped structure.

In a fourth embodiment, a method of manufacturing and packaging a cannabis juice purée is provided. In one specific embodiment, the packaged cannabis juice purée has an amount of non-decarboxylated cannabinoids and is non-psychoactive. In another specific embodiment, the packaged cannabis juice purée has an amount of non-decarboxylated cannabinoids and an amount of decarboxylated cannabinoids.

In a first step, a cannabis juice purée is formed. To form a packaged cannabis juice purée that is non-psychoactive, raw cannabis material having an amount of non-decarboxylated cannabinoids is collected but never heated. The raw cannabis material is blended together with a thickening agent and a sweetening agent such as honey, stevia, fruit juice, sugar, or corn syrup. Non-decarboxylated high concentrate cannabis extract may also be added to the cannabis juice purée to increase the amount of non-decarboxylated cannabinoids in each container.

To form a packaged cannabis juice purée that comprises decarboxylated cannabinoids, a portion of the collected raw cannabis material is heated to obtain an amount of decarboxylated cannabinoids. The amount of decarboxylated cannabinoids are added to the cannabis juice purée. Non-decarboxylated high concentrate cannabis extract, decarboxylated high concentrate cannabis extract, decarboxylated cannabis infusion, or heated cannabis material may also be added to the cannabis juice purée to increase the amount of non-decarboxylated and decarboxylated cannabinoids in each container.

In a second step, cannabis juice purée is deposited into a container. The container is a cylindrical shaped structure having a lid. The container is formed from a glass material, a plastic material, or a paper-based material. The cannabis juice purée is deposited into the container through an opening.

In a third step, the container having the cannabis juice purée is packaged. In one example, the cannabis juice purée is processed using high pressure processing (HPP). In HPP, the cannabis juice purée is loaded into a high pressure chamber filled with pressure transmitting fluid, such as water. The pressure is applied to the cannabis juice purée. A lid is used to seal the opening of the container.

HPP allows the mixture to be pasturized without applying heat. HPP extends shelf life of the cannabis juice purée to several weeks to months without applying heat that could undesirably decarboxylate the cannabinoids present in the cannabis juice purée. Thus, shelf life is preserved while providing a liquid beverage form of cannabis juice purée.

Forming the cannabis juice purée and freezing cannabis juice purée into serving size cubes or ice pops is a significant improvement over the conventional art. Significant research and testing was involved to ascertain the optimal process and technique. For example, this development process involves selecting the most effective strains of cannabis having optimal cannabinoid profiles, determining the effective proportions and amounts of materials to combine to ensure a consistent dosage amount of cannabinoids per serving, and selecting the optimal technique for creating the cannabis juice purée, selecting the size and shape of the cube, and determining the most efficient and convenient packaging for the end consumer.

In particular, the invention yields significant advantages over prior attempts of forming mixture via juicing machines or wheat grass juicers. For example, prior attempts using conventional juicing machines or wheat grass juicers resulted in very little juice and substantial leaf pulp. The conventional juicing machines or wheat grass juicers were not powerful enough to blend the raw cannabis leaves into the smooth purée consistency that is desired for the cannabis juice purée. Such conventional blenders generated leaf pulp that was too thick and abrasive for consumption. However, a high powered juice blender (such as a Vitamix blender) with water and banana achieved the most desirable cannabis juice purée having the proper texture and purée composition. In addition, without the banana, the cannabis juice purée separated into raw cannabis material on bottom and water on top.

In addition, conventional techniques did not have the proper size and shape to achieve a dosage of over 20 milligrams of cannabinoids per cube. The recipe, cube size, and technique for creating the cubes resulted from substantial laboratory testing to achieve the desired results. Consequently, one of ordinary skill will appreciate that the various novel embodiments allow the mass market to have reliable and cost effective access to non-decarboxylated cannabis material which contains consistent levels of THCa, CBDa, and all of the other non-decarboxylated cannabinoids present in raw cannabis material.

One technique for making "marijuana juice" ice cubes is known. To make "marijuana juice" ice cubes, a juice extractor is used to extract "marijuana juice" from leaves of cannabis plants. The extracted "marijuana juice" is used to make ice cubes. Several shortcomings exist with this technique. First, using a juice extractor removes many non-cannabinoid components present in the cannabis plant material (stems, leaves, flowers, etc.) that offer significant nutritional value. Second, juice extractors tend to emit heat during use, especially extended use, and this emitted heat may undesirably decarboxylate the cannabinoids present in the leaves. Such overheating also renders juice extractors inefficient for commercial production. Third, the "marijuana juice" ice cubes do not have consistent doses of cannabinoids in each ice cube. One ice cube may have more cannabinoids than another ice cube. Consistent dosage is essential for patients who require specific amounts of cannabinoids to treat illness and who also require consistent doses to monitor progress and adjust cannabinoid intake as needed. Additionally, many patients require specific ratios of one cannabinoid to another cannabinoid for achieving desired medical benefits. The "marijuana juice" ice cubes do not yield consistent doses of cannabinoids or specific ratios of cannabinoids. Fourth, the "marijuana juice" ice cubes are not packaged and are meant to be removed from an ice cube tray to be consumed by the user. Typical patients require consistent access to cannabinoids. Packaging the "marijuana juice" ice cubes is difficult because the ice cubes can meld together causing additional inconsistencies in dosage amounts. No effective way to package, store, and commercially distribute the "marijuana juice" ice cubes is known. Consequently, the "marijuana juice" ice cubes are not a commercially viable technique for administering cannabinoids along with cannabis plant material rich in nutrients that are stored and packaged for mass distribution. Lastly, no technique is known for adding high concentrate cannabis extract or cannabis infusion to the "marijuana juice" ice cubes. Many patients require high amounts of specific non-decarboxylated or decarboxylated cannabinoids which is not feasible to achieve by consuming the "marijuana juice" ice cubes. The novel packaged frozen cannabis juice purée cubes solve all of these shortcomings.

The foregoing is a summary and thus contains, by necessity, simplifications, generalizations and omissions of detail; consequently it is appreciated that the summary is illustrative only. Still other methods, and structures and details are set forth in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 10D is a table 170 showing various non-cannabinoid components and cannabinoid components that are obtainable from cannabis plant material.

FIG. 11 is a table 163 showing two general types of non-decarboxylated cannabinoids.

FIG. 37 is a diagram of a conventional coconut milk based cannabis ice cream 420.

FIG. 38 is a diagram showing how the container 421 is placed onto a container holder 423.

FIG. 39 is a diagram showing how the container holder 423 having six containers is placed into a package 425.

FIG. 40 is a diagram of the package 425 containing the container holder 423 having the six containers with coconut milk based cannabis ice creams.

FIG. 41 is a table 500 showing the advantages of novel package 154 (shown in FIG. 7) and novel package 254 (shown in FIG. 19) over the conventional package 425 shown in FIG. 40.

FIG. 46B is a perspective diagram of another embodiment of a packaged frozen ice pop of cannabis juice purée with added decarboxylated cannabis infusion and non-decarboxylated high concentrate cannabis extract.

FIG. 46D is a perspective diagram of another embodiment of a packaged frozen ice pop of cannabis juice purée with added decarboxylated high concentrate cannabis extract and non-decarboxylated high concentrate cannabis extract.

FIG. 48 is a diagram of a side view of the packaged frozen ice pop of cannabis juice purée 632/634.

FIG. 49 is a diagram of a top view of the packaged frozen ice pop of cannabis juice purée 632/634.

FIG. 50 is a diagram of a side view of another embodiment of a packaged frozen ice pop of cannabis juice purée 650 having a container 651 that is not resealable.

FIG. 58B is a perspective diagram of another embodiment of a packaged cannabis juice purée with added non-decarboxylated high concentrate cannabis extract.

FIG. 59B is a perspective diagram of another embodiment of a packaged cannabis juice purée with added decarboxylated cannabis infusion and non-decarboxylated high concentrate cannabis extract.

FIG. 59C is a perspective diagram of another embodiment of a packaged cannabis juice purée with added decarboxylated high concentrate cannabis extract.

FIG. 59D is a perspective diagram of another embodiment of a packaged cannabis juice purée with added decarboxylated high concentrate cannabis extract and non-decarboxylated high concentrate cannabis extract.

FIG. 62 is a table 1100 that shows the therapeutic benefits of various types of cannabinoids.

Reference will now be made in detail to some embodiments of the invention, examples of which are illustrated in the accompanying drawings.

DETAILED DESCRIPTION

Figure 1:
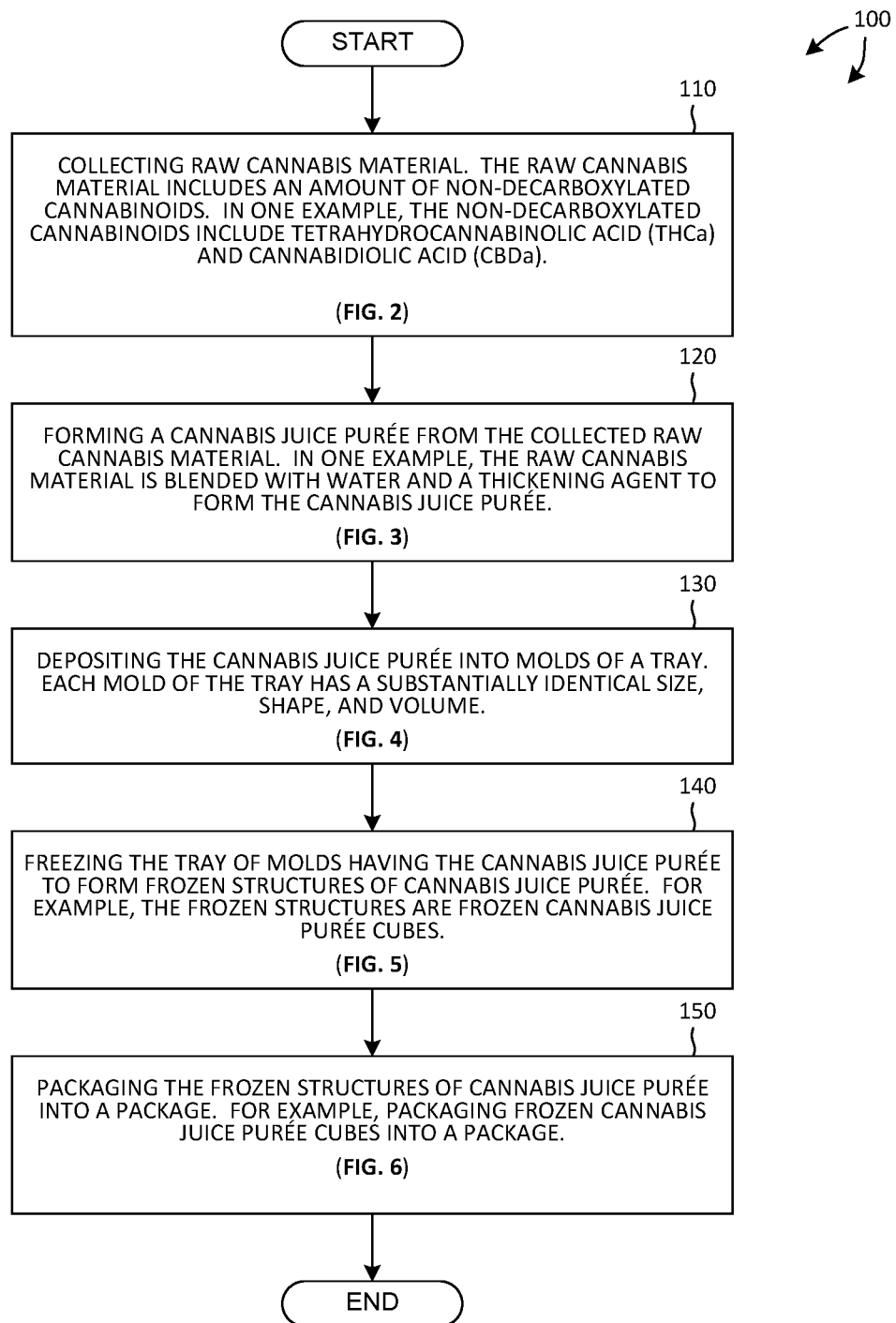
FIG. 1 is a flowchart of a method 100 in accordance with one embodiment.

FIG. 1 is a flowchart of a method 100 in accordance with one embodiment. The method 100 is a method of manufacturing and packaging a plurality of frozen structures of cannabis juice purée that comprises a pre-determined amount of non-decarboxylated cannabinoids.

Figure 10A:
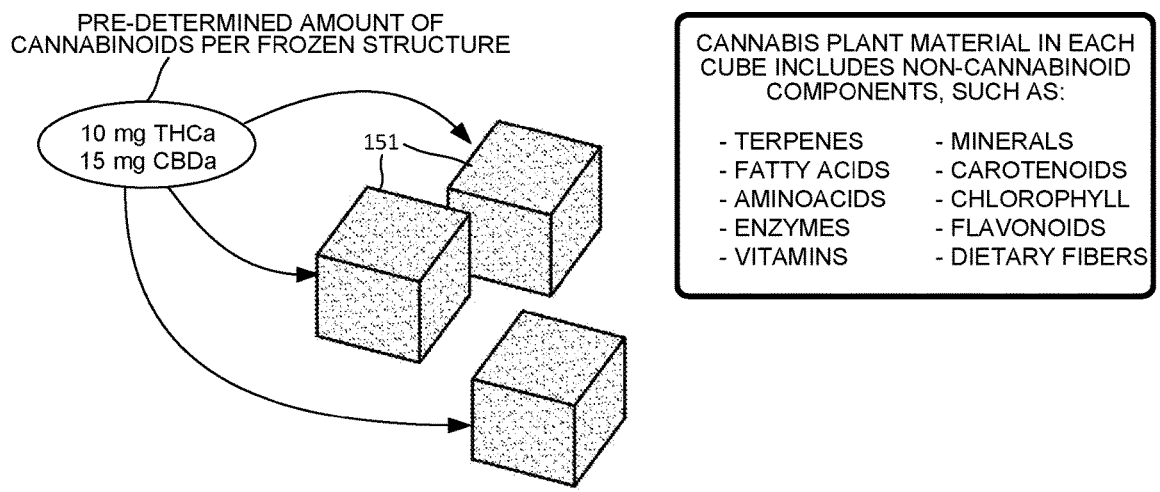
FIG. 10A is a perspective diagram of frozen cannabis juice purée cubes 151 having an amount of non-decarboxylated cannabinoids.

In a first step (step 110), raw cannabis material is collected. The raw cannabis material includes an amount of non-decarboxylated cannabinoids. The term "non-decarboxylated" means that the cannabinoids are in their acid form. Non-decarboxylated cannabinoids are not considered to be psychoactive. For example, in FIG. 2, raw cannabis material 112 is collected by trimming leaves 113 from the cannabis plant 111. The cannabinoid profile indicates types and proportions of cannabinoids present in the cannabis material. An example of a cannabinoid profile is shown in FIG. 10A where the cannabinoid contents of the cubes is shown.

Figure 2:
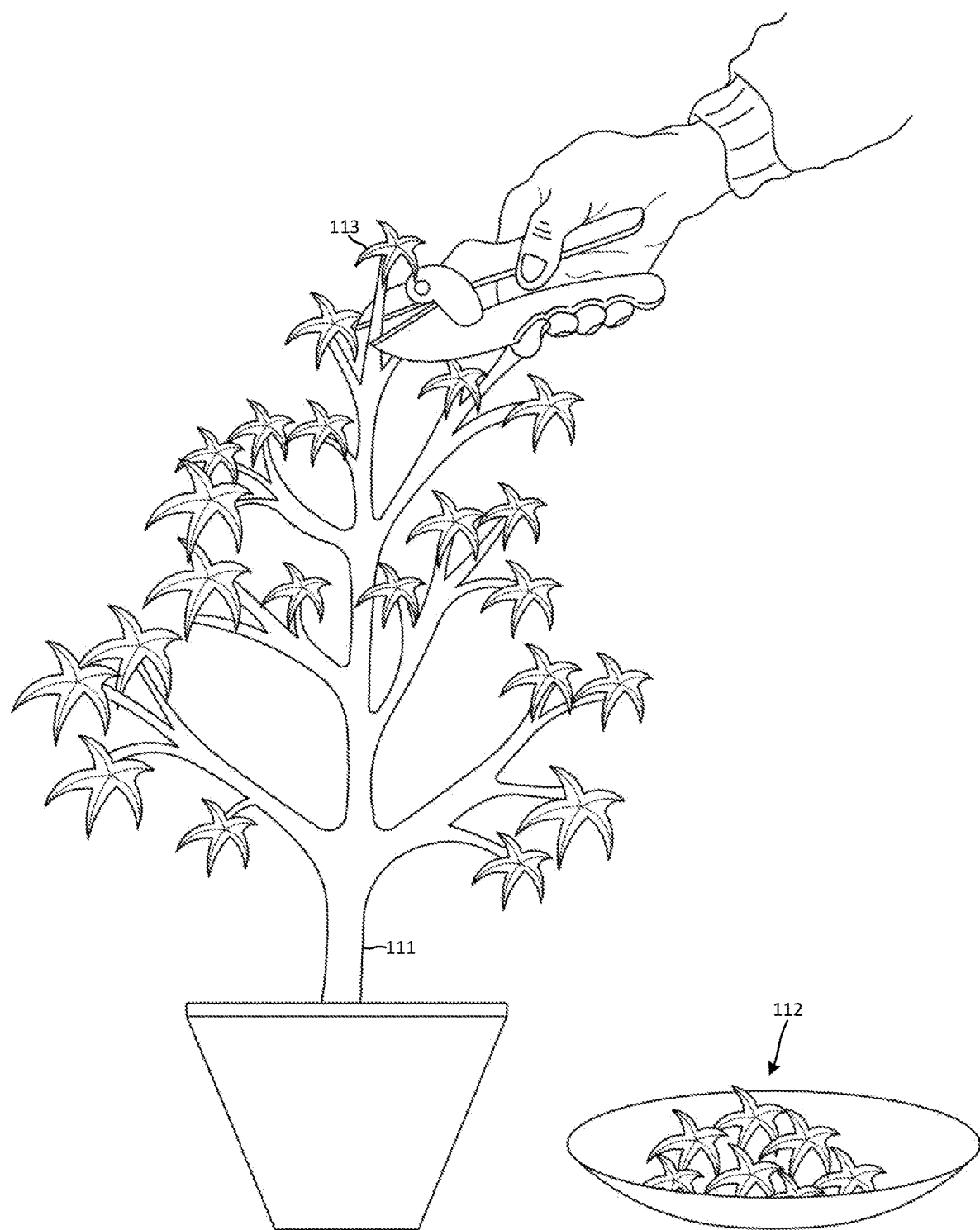
FIG. 2 is a perspective diagram showing how raw cannabis material 112 is collected by trimming leaves 113 from the cannabis plant 111.

The cannabis plant 111 is cultivated to have a specific cannabinoid profile. Different cannabinoid profiles yield different therapeutic benefits appreciated by an artisan of ordinary skill. In this example, the cannabis plant 111 has a cannabinoid profile that includes tetrahydrocannabinolic acid (THCa) and cannabidiolic acid (CBDa). The cannabis plant 111 is selected having a cannabinoid profile where the amount of THCa and CBDa is present in a desired ratio. In the example of FIG. 2, the ratio is 3 CBDa to 2 THCa. In other examples, the ratio is taken from the group consisting of: 2 CBDa to 1 THCa, 1 CBDa to 1 THCa, 1 CBDa to 2 THCa, 1 CBDa to 3 THCa, 3 CBDa to 1 THCa, 0 CBDa to 1 THCa (no CBDa, only THCa), and 1 CBDa to 0 THCa (no THCa, only CBDa).

For additional information on cannabinoid profiles, their therapeutic benefits, and techniques for delivering the cannabinoids to a user, see: (1) U.S. Pat. No. 9,220,294, entitled "Methods and Devices Using Cannabis Vapors", filed Apr. 29, 2014 by McCullough; (2) U.S. Pat. No. 9,205,063, entitled "Cannabinoid-containing Plant Extracts As Neuroprotective Agents", filed Jan. 24, 2014 by Guy et al.; (3) U.S. Pat. No. 9,186,386, entitled "Pharmaceutical Composition And Method Of Manufacturing", filed May 28, 2015 by Speier; (4) U.S. Pat. No. 9,155,767, entitled "Essential Element Management", filed Oct. 18, 2012 by Hospodor et al.; (5) U.S. Pat. No. 9,149,499, entitled "Cannabis Based Therapeutic And Method Of Use", filed May 19, 2014 by Robinson; (6) U.S. Pat. No. 9,095,563, entitled "Topical Treatments Incorporating Cannabis Sp. Derived Botanical Drug Product", filed Sep. 26, 2014 by Sekura et al.; (7) U.S. Pat. No. 9,095,544, entitled "Breeding, Production, Processing and Use of Specialty Cannabis", filed Mar. 17, 2014 by Lewis et al.; (8) U.S. Pat. No. 9,078,838, entitled "Cosmetic or Dermatological Compositions Comprising A Mixture Of Essential Oils, And Its Uses Thereof, Particularly For The Care Of Sensitive Or Sensitized Skin", filed Sep. 3, 2009 by Andre et al.; (9) U.S. Pat. No. 9,066,910, entitled "Methods and Compositions of Cannabis Extracts", filed Apr. 15, 2010 by Rosenblatt et al.; (10) U.S. Pat. No. 9,050,631, entitled "Apparatus and Related Methods For Extracting Resins From Cannabis", filed Feb. 6, 2013 by Raichart; and (11) U.S. Pat. No. 9,044,390, entitled "Pharmaceutical Composition And Method Of Manufacturing", filed Apr. 17, 2014 by Speier (the subject matter of these patent documents is incorporated herein in its entirety).

Figure 3:
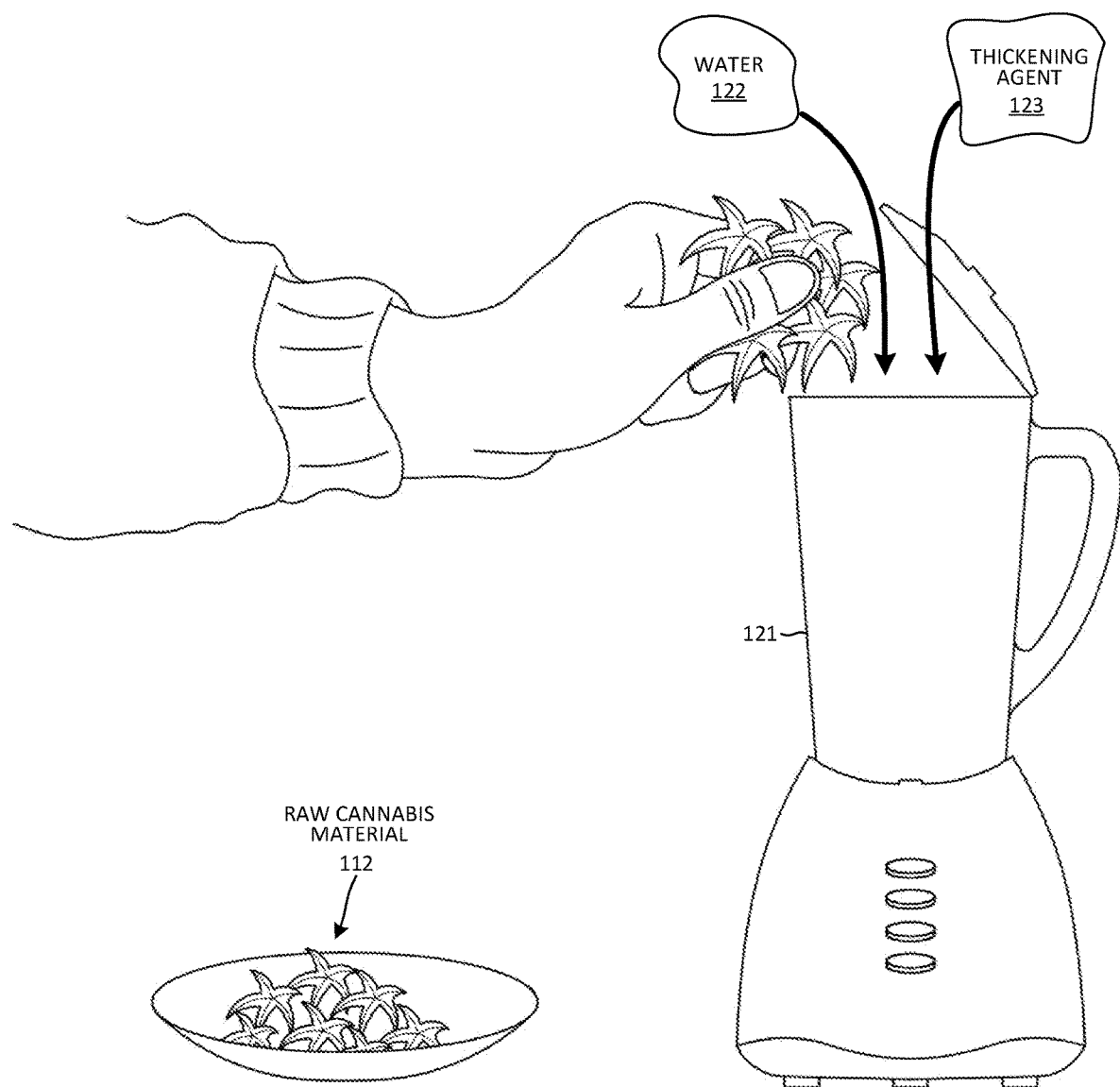
FIG. 3 is a perspective diagram showing how the cannabis juice purée is formed.

In a second step (step 120), a cannabis juice purée is formed from the collected raw cannabis material. The cannabis juice purée has a liquid composition and is also referred to as a uniform purée. For example, in FIG. 3, the raw cannabis material 112 is blended in a blender 121 with water 122 and a thickening agent 123 to form a cannabis juice purée. In one example, 210.0 grams of fresh cannabis leaves, 200.0 grams of banana, and 20.0 ounces of filtered water are combined in blender 121 and blended together. The blender 121 is not a juicing machine. Both the shredded cannabis plant material and the extracted cannabis juice remain in the blender after the blending process and become part of the resulting cannabis juice purée.

In accordance with one novel aspect, the cannabis juice purée is formed without a juicing process. In a juicing process, a portion of the cannabis plant material is separated from the juice of the cannabis plant. At least part of the separated cannabis plant material is treated as waste and is disposed. To form the cannabis juice purée, however, all of the cannabis plant material is converted into the cannabis juice purée. The resulting cannabis juice purée includes all of the cannabis plant material placed in the blender and all of the extracted cannabis juice that is extracted in the blending process. No waste product is generated in forming the cannabis juice purée. Accordingly, the cannabis juice purée has all of the cannabis plant material and is rich in dietary fibers and non-cannabinoid components that include terpenes, fatty acids, aminoacids, enzymes, vitamins, minerals, carotenoids, chlorophyll, and flavonoids.

The water 122 may be filtered water, unfiltered water, ice formed from filtered water, or ice formed from unfiltered water. Alternatively, fruit juice or vegetable juice can be used in addition to or instead of water. The thickening agent 123 aids in suspending the cannabis material throughout thereby yielding a more uniform distribution of cannabinoids than would otherwise be achieved without the thickening agent 123. If no thickening agent 123 is used, then blending the cannabis material 112 and water 122 results in a mixture having the cannabis material sinking to the bottom with water disposed above the cannabis material. The thickening agent 123 may be banana, avocado, psyllium husk, tapioca, or any other food-grade thickening agent.

Figure 4:
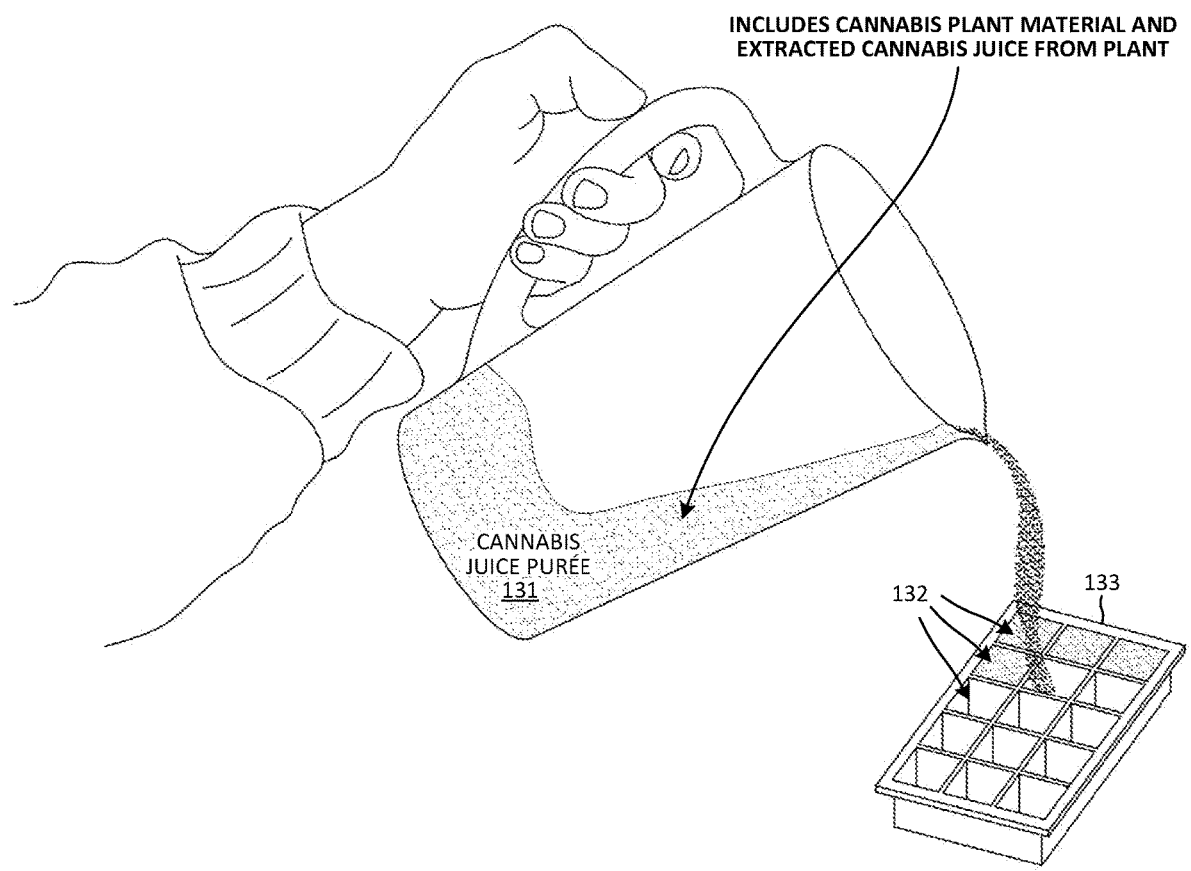
FIG. 4 is a perspective diagram showing how the cannabis juice purée 131 is deposited into molds 132.

In a third step (step 130), the cannabis juice purée is deposited into molds of a tray. The tray has a plurality of molds each having a substantially identical size, shape, and volume. Depositing the cannabis juice purée into similar molds results in each cube having a substantially similar cannabinoid profile. For example, in FIG. 4, the cannabis juice purée 131 is deposited into molds 132 of a tray 133. In the embodiment of FIG. 4, the tray 133 has fifteen cubic shaped molds that each holds one fluid ounce. The size, shape, and volume of each mold and the number of molds on the tray are selected depending on the desired size of the frozen cannabis juice purée cubes and amount of cannabinoids to be delivered in each dose.

Figure 5:
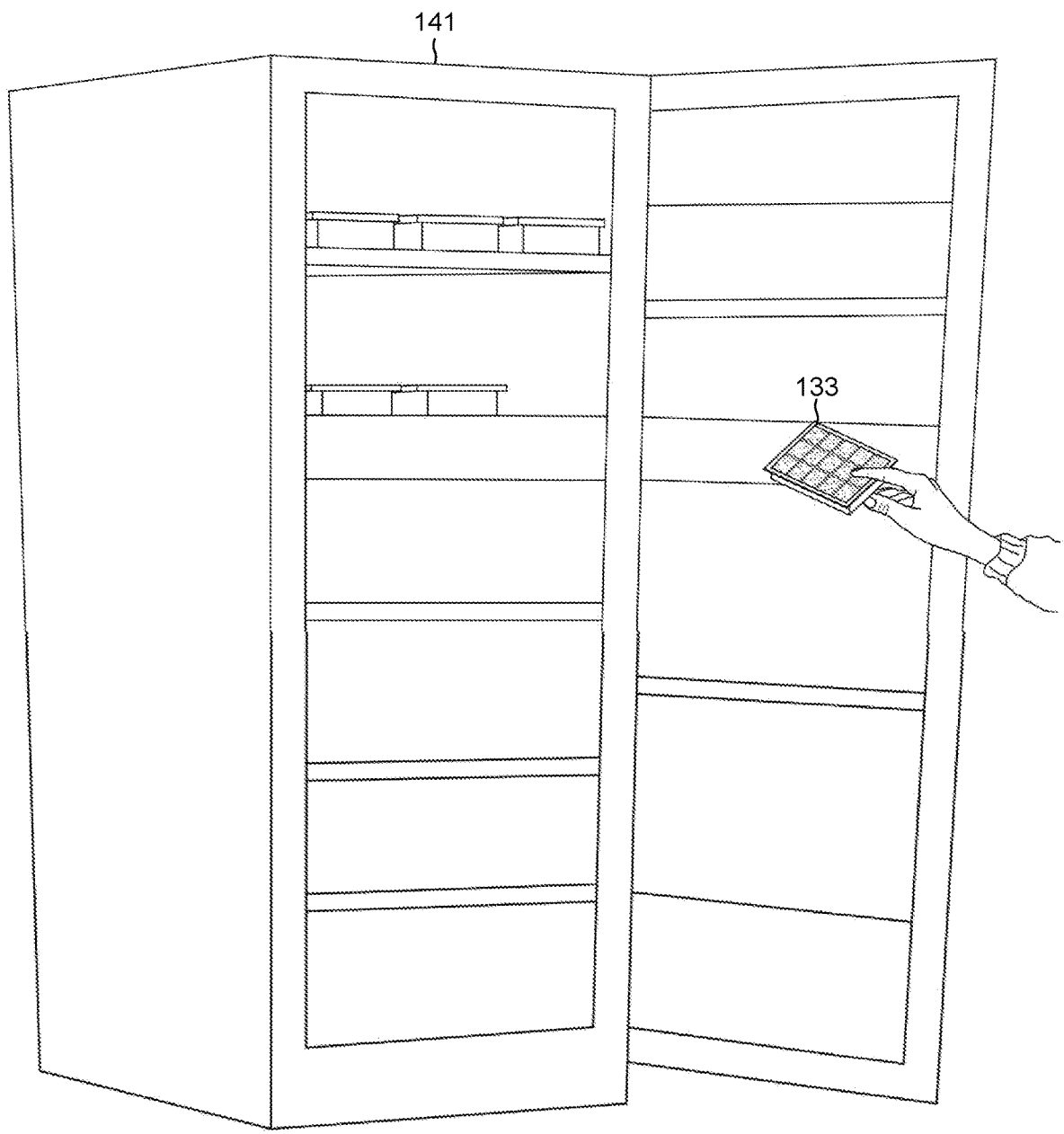
FIG. 5 is a perspective diagram showing how the tray 133 is placed in a freezer 141.

In a fourth step (step 140), the tray of molds having the cannabis juice purée are frozen to form frozen structures of cannabis juice purée. In one example, frozen structures of cannabis juice purée are frozen cannabis juice purée cubes. In FIG. 5, for example, the tray 133 of molds 132 having the cannabis juice purée 131 is placed in a freezer 141 so that the cannabis juice purée 131 in each mold of tray 133 can freeze. The temperature within freezer 141 is typically between 0.0° F. and 5.0° F., but may be less than 0.0° F. Freezing the cannabis juice purée promotes preservation because harvested raw cannabis material is not acceptable for consumption after three days, even when the cannabis material is stored in a refrigerator. However, by freezing the cannabis juice purée to form frozen cannabis juice purée cubes, the shelf-life is extended for at least six months if the frozen cannabis juice purée cubes are properly stored in a freezer.

Figure 6:
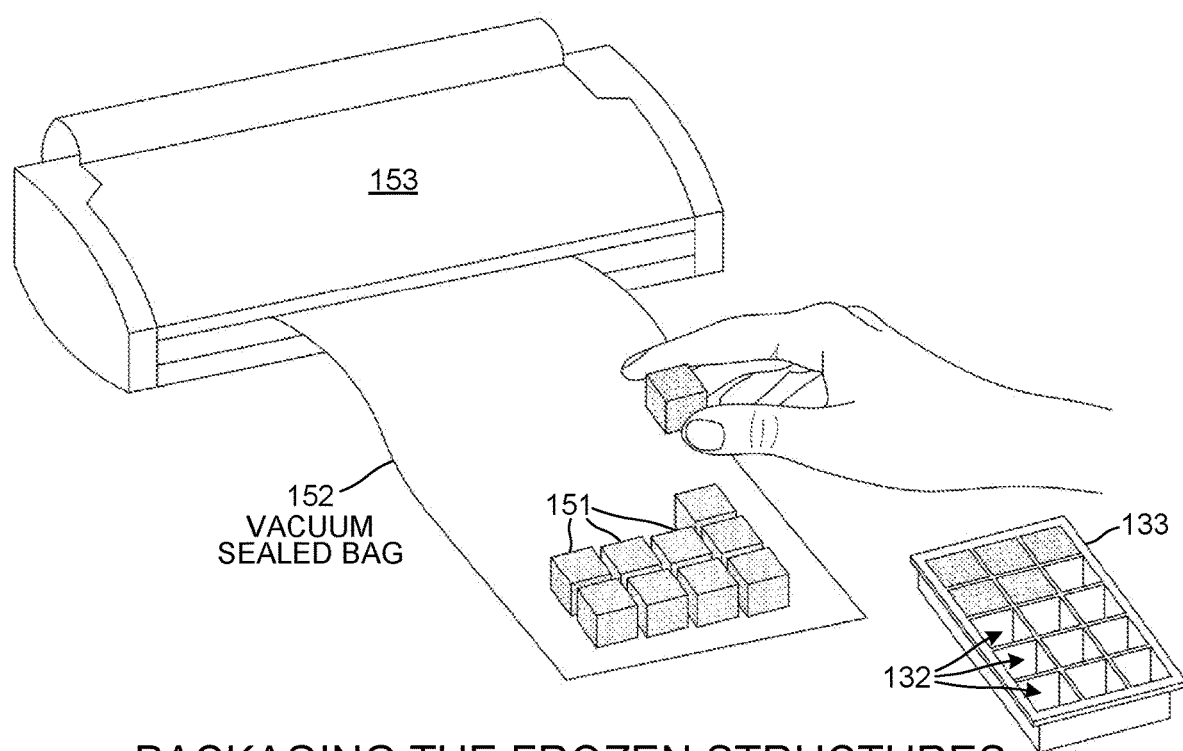
FIG. 6 is a perspective diagram showing how the frozen cannabis juice purée cubes 151 are removed from tray 133 and placed on vacuum sealed bag 152.

In a fifth step (step 150), the frozen structures of cannabis juice purée are packaged into a package. The frozen structures of cannabis juice purée are packaged in a vacuum sealed package, a bag, or a container having a detachable lid. The frozen structures may be loosely packed or may directly contact each other. In the example of FIG. 6, the frozen cannabis juice purée cubes 151 are removed from the molds 132 of the tray 133 and are placed on vacuum sealed bag 152. The vacuum sealed bag 152 is sealed by vacuum sealing machine 153 to form a vacuum sealed package having the frozen cannabis juice purée cubes 151.

Figure 7:
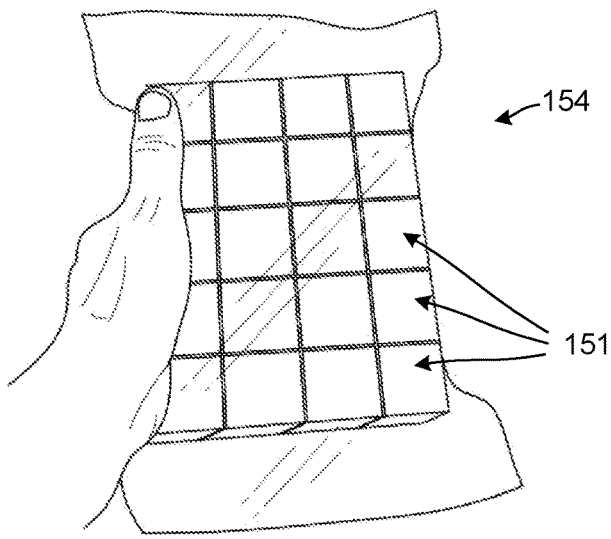
FIG. 7 is a perspective diagram of a package 154 with the frozen cannabis juice purée cubes 151.

FIG. 7 is a perspective diagram of a package 154 with the frozen cannabis juice purée cubes 151. The frozen cannabis juice purée cubes 151 have non-decarboxylated cannabinoids because the cannabis material 112 involved in forming the cubes 151 has not been heated. The package 154 delivers the frozen cannabis juice purée cubes 151 cheaply because the only packaging material involved is the vacuum sealed bag. The package 154 provides for optimal storing, packing, and transporting because the packages are rectangular or square and have flat surfaces that allow the packages to be stacked above each other. The frozen cannabis juice purée cubes 151 consume over 95% of the total volume of package 154 allowing for maximum delivery of frozen cannabis juice purée cubes per shipment of packages.

Figure 8:
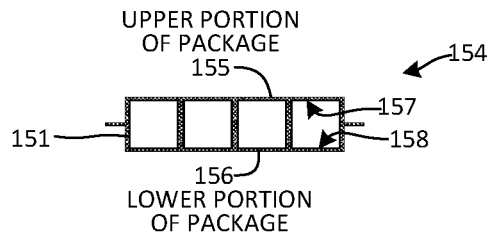
FIG. 8 is a side view of the package 154 with the cubes 151.

FIG. 8 is a side view of the package 154 with the cubes 151. The package 154 has an upper portion 155 and a lower portion 156. Each of the cubes 151 has an upper surface 157 and a lower surface 158. Each upper surface 157 of the cubes contacts the upper portion 155 of the package 154 and each lower surface 158 of the cubes 151 contacts a lower portion 156 of the package 154. No packaging material is disposed within the package.

Figure 9:
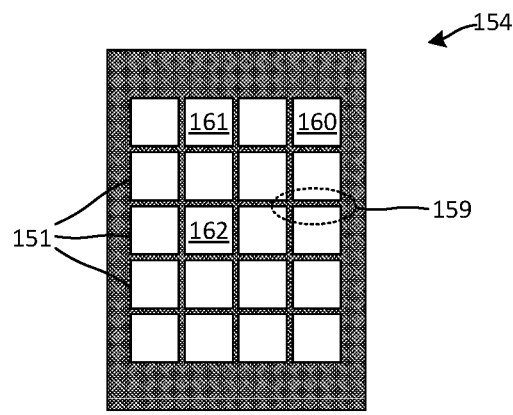
FIG. 9 is top view of the package 154 with the frozen cannabis juice purée cubes 151.

FIG. 9 is top view of the package 154 with the frozen cannabis juice purée cubes 151. The frozen cannabis juice purée cubes 151 are packaged in an array formation. Each of the frozen cannabis juice purée cubes 151 has a substantially identical shape and each cube is adjacent to at least one other cube. Reference numeral 159 identifies a surface of one cube adjacent to a surface of another cube. Each cube has at least two surfaces that are adjacent to surfaces of at least two other cubes.

Reference numeral 160 identifies a cube along a corner of the array of cubes 151 having a first surface that is adjacent to a surface of a second cube and a second surface that is adjacent to a surface of a third cube. Cube 160 has two surfaces each of which contacts a surface of one of two other cubes. Reference numeral 161 identifies a cube along an edge of the array of cubes 151 having a first surface that is adjacent to a surface of a second cube, a second surface that is adjacent to a surface of a third cube, and a third surface that is adjacent to a surface of a fourth cube. Cube 161 has three surfaces each of which contacts a surface of one of three other cubes. Reference numeral 162 identifies a cube at an inner portion of the array of cubes 151 having a first surface that is adjacent to a surface of a second cube, a second surface that is adjacent to a surface of a third cube, a third surface that is adjacent to a surface of a fourth cube, and a fourth surface that is adjacent to a surface of a fifth cube. Cube 162 has four surfaces each of which contacts a surface of one of four other cubes.

In accordance with at least one novel aspect, the cubes 151 are not contained in separate containers. No packaging material is present between the cubes 151. Although a gap is shown between the cubes 151, some or all of the cubes 151 may be directly contacting each other. The tight packing of the cubes 151 and the omission of additional packaging material between the cubes significantly reduces packaging, storing, and shipping costs.

In another example, the frozen cannabis juice purée cubes 151 are loosely packed in a bag without vacuum sealing. Costs and packaging time are substantially reduced by not vacuum sealing. Not all of the cubes 151 contact a surface of the bag. Some of the cubes in the bag are surrounded by other cubes and do not touch a surface of the bag. In yet another example, the frozen cannabis juice purée cubes 151 are loosely packed in a plastic container having a lid. Not all of the cubes contact a surface of the plastic container. Depending on the size of the container, the cubes may not contact the lid of the container.

FIG. 10A is a perspective diagram of frozen cannabis juice purée cubes 151 having an amount of non-decarboxylated cannabinoids. The amount of non-decarboxylated cannabinoids comprises an amount of tetrahydrocannabinolic acid (THCa) and an amount of cannabidiolic acid (CBDa). The cubes 151 do not include any decarboxylated cannabinoids and the cubes 151 are not psychoactive. Each of cubes 151 is a frozen cube of one fluid ounce and has ten milligrams of THCa and fifteen milligrams of CBDa. The ratio of CBDa to THCa is 3:2. In other examples, each frozen structure has between 0.1 fluid ounce and 5.0 fluid ounces of cannabis juice purée. Each cube comprises cannabis plant material that includes leaves, stems, flowers, or trichomes of the cannabis plant. Each cube can be modified to include or exclude non-cannabinoid components of the cannabis plant such as terpenes, fatty acids, aminoacids, enzymes, vitamins, minerals, carotenoids, chlorophyll, flavonoids, and dietary fibers.

In the example of FIG. 10A, the amount of CBDa in each cube is greater than the amount of THCa. In other embodiments, each cube has ratio of CBDa to THCa taken from the group consisting of: 2 CBDa to 1 THCa, 1 CBDa to 1 THCa, 1 CBDa to 2 THCa, 1 CBDa to 3 THCa, 3 CBDa to 1 THCa, 0 CBDa to 1 THCa (no CBDa, only THCa), and 1 CBDa to 0 THCa (no THCa, only CBDa). An artisan will appreciate that another combination of cannabinoids (amount, type, or ratio) can be selected to form the cubes according to the type of ailment being targeted.

Figure 10B:
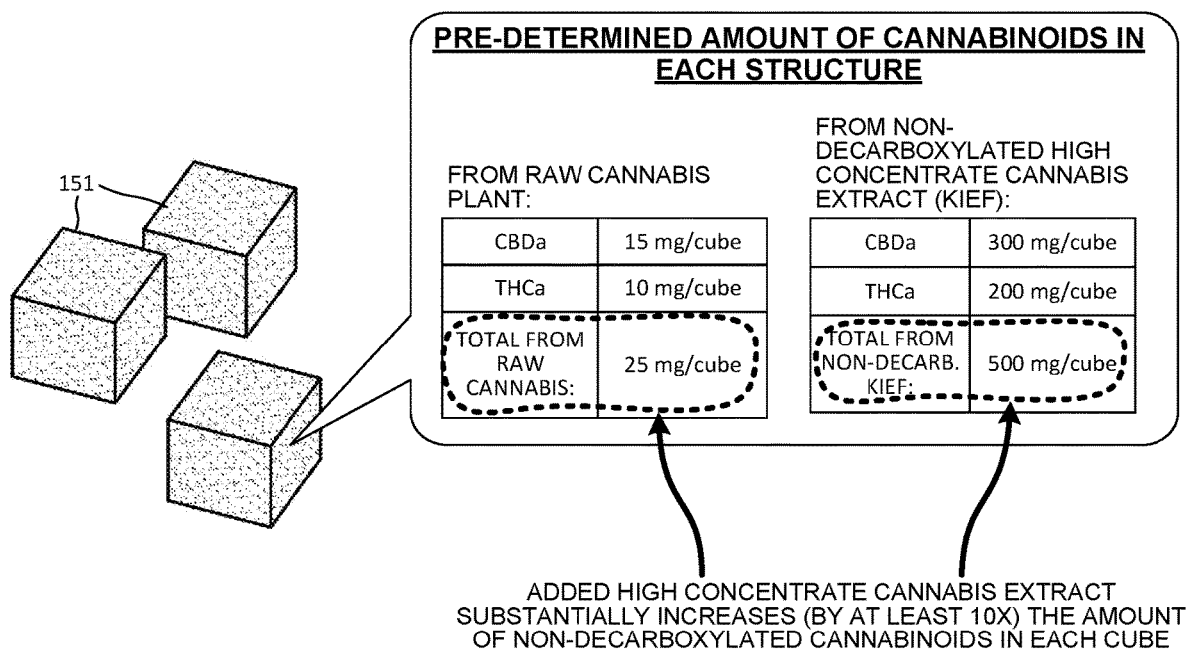
FIG. 10B is a perspective diagram of another embodiment of the frozen structures where an amount of non-decarboxylated high concentrate cannabis extract has been added to the cannabis juice purée prior to freezing.

FIG. 10B is a perspective diagram of another embodiment of the frozen structures where an amount of non-decarboxylated high concentrate cannabis extract has been added to the cannabis juice purée prior to freezing. High concentrate cannabis extract is also referred to as "kief". The added amount of non-decarboxylated high concentrate cannabis extract substantially increases the amount of non-decarboxylated cannabinoids in each cube. For example, in addition to the 25 milligrams of non-decarboxylated cannabinoids derived from the cannabis leaf, there is an additional 500 milligrams of non-decarboxylated cannabinoids in each cube derived from the added non-decarboxylated high concentrate cannabis extract. The amount of cannabinoids from the non-decarboxylated high concentrate cannabis extract is at least ten times the amount of non-decarboxylated cannabinoids from the raw cannabis plant. The high concentrate cannabis extract is obtained through numerous processes and added to the cubes, as explained below in connection with FIG. 10C.

Figure 10C:
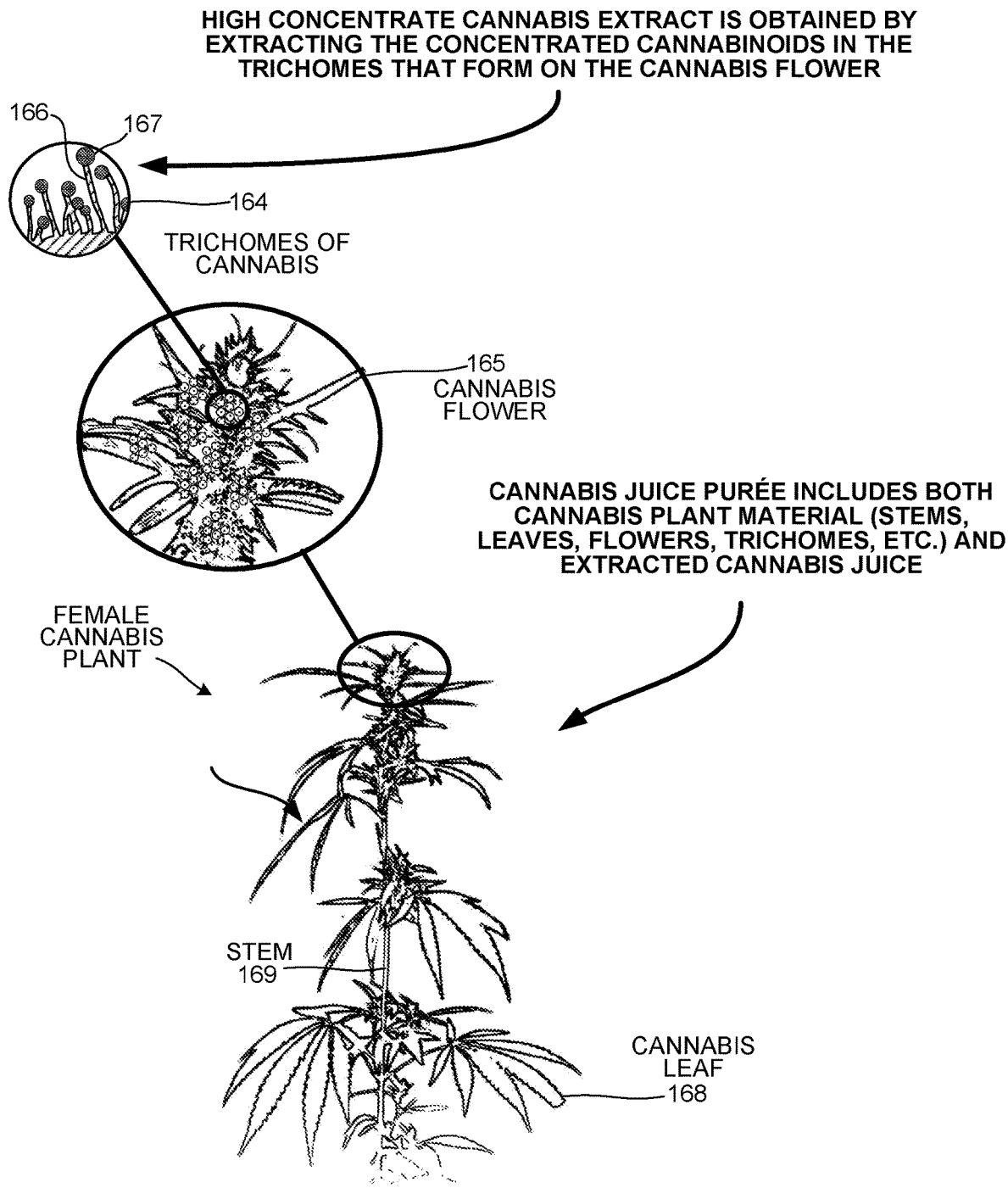
FIG. 10C is a diagram of a female cannabis plant with flowers 165 having trichomes 164.

FIG. 10C is a diagram of a female cannabis plant with flowers 165 having trichomes 164. The high concentrate cannabis extract is obtained by collecting the trichomes 164 from many cannabis plants. The trichomes 164 are typically present along an upper surface of a cannabis flower 165. Each trichome has a stalk 166 and a gland head 167. Secretory vesicles along the gland head 167 receive nutrients and turn them into cannabinoids. As flowering progresses, cannabinoids accumulate on an outer layer of the gland head 167. Generally, the greatest concentration of cannabinoids in a cannabis plant is found in the trichomes 164. The high concentrate cannabis extract is obtained by extracting the cannabinoids from the trichomes 164 of the cannabis plant. High concentrate cannabis extract is any material that has a greater percentage of cannabinoids per unit mass than cannabis in its unprocessed and natural occurring state, such as in the leaves 168 or stem 169. The high concentrate cannabis extract is also referred to as "kief" or "high potency resin extract".

Several techniques exist to obtain high concentrate cannabis extract. A first technique to obtain high concentrate cannabis extract involves sifting or tumbling raw cannabis flower material. The cannabis material that contains trichrome—the cannabinoid crystals—is generally present in the cannabis flower material. Agitating and sifting the flower material causes the trichrome crystals to separate from the plant material. By employing this technique, the high concentrate cannabis extract will have much higher percentage of cannabinoids per gram. It is not uncommon for high concentrate cannabis extract to contain between 30% and 60% cannabinoids per gram. This could result in at least between 300 milligrams and 600 milligrams of cannabinoids (THCa or CBDa) per gram of high concentrate cannabis extract. When adding raw kief to frozen cannabis juice purée cubes, each gram of high concentrate cannabis extract added to the cube can increase the amount of cannabinoids per ounce of cube by between 300 milligrams and 600 milligrams.

A second type of high concentrate cannabis extract is obtained by using $CO_2$ extraction, alcohol extraction, or other forms of high concentrate extraction using solvents or alcohols. High concentrate cannabis extract obtained through these other extractions methods may be obtained and added to the frozen cannabis juice purée cubes prior to freezing or after freezing. Such high concentrate extraction, when performed with high quality precision equipment, results in considerably high concentrate cannabis extract or oils with almost undetectable amounts of the solvent remaining. If the resulting high concentrate cannabis extract are never heated (decarboxylated), these high concentrate cannabis extract or oils can be added to the cannabis juice purée to dramatically increase the amount of cannabinoids per cube.

In one example, while pouring the cannabis juice purée into the molds, an amount of high concentrate cannabis extract is weighed and added into each of the individual molds. For example, the cannabis juice purée is filled to half the volume of the mold. Next, the high concentrate cannabis extract is deposited into the half filled mold. Next, the remainder of the mold is filled with the cannabis juice purée. This would maintain the high concentrate cannabis extract in a center of the frozen cannabis juice purée cubes. In another example, while blending the raw cannabis material, high concentrate cannabis extract is added to the entire cannabis juice purée. This is not as preferred, as some of the valuable high concentrate cannabis extract could be lost in the residue on the side of the mixing or blending apparatus.

By adding high concentrate cannabis extract to the cubes, the concentration of cannabinoids per cube can be increased to over 600 mg of cannabinoids per cube, if an entire gram of high concentrate cannabis extract were added per cube. In one specific embodiment, 500 milligrams of high concentrate cannabis extract is added in each cannabinoid cube. An artisan of ordinary skill will appreciate that employing high concentrate cannabis extract allows for a completely 'natural' way to achieve very high cannabinoid potency per cube. In addition, there are no solvents or alcohol used to extract the high concentrate cannabis extract thereby reducing costs and production time and yields 'food grade' frozen cannabis juice purée cubes.

FIG. 10D is a table 170 showing various non-cannabinoid components and cannabinoid components that are obtainable from cannabis plant material. The left-side column of table 170 shows non-cannabinoid components that can be obtained from the cannabis plant. The non-cannabinoid components include terpenes, fatty acids, aminoacids, enzymes, vitamins, minerals, carotenoids, chlorophyll, flavonoids, and dietary fibers. The right-side column of table 170 shows cannabinoid components that can be obtained from the cannabis plant. The cannabinoid components include cannabigerolic acid (CBGa), cannabigerovarin acid (CBGVA), tetrahydrocannabinolic acid (THCA), tetrahydrocannabivarin carboxylic acid (THCVA), cannadidiolic acid (CBDA), cannabidivarin acid (CBDVA), cannabichrome carboxylic acid (CBCA), cannabichrome varinic acid (CBCVA), tetrahydrocannabinol (THC), tetrahydrocannabidivarin (THCV), tetrahydrocannabivarin acid (THVA), cannabidiol (CBD), cannabidivarin (CBDV), cannabichromene (CBC), cannabichromevarin (CBCV), cannabigerol (CBG), cannabigerovarin (CBGV), cannabinerolic acid (CBNA), cannabigerovarinic acid (CBNVA), cannabinol (CBN), cannabicyclol (CBL), and cannabicyclol acid (CBLA).

FIG. 11 is a table 163 showing two general types of non-decarboxylated cannabinoids, THCa and CBDa, along with their chemical names and structural formulas. The non-decarboxylated cannabinoids include a carboxyl group (COOH).

Figure 12:
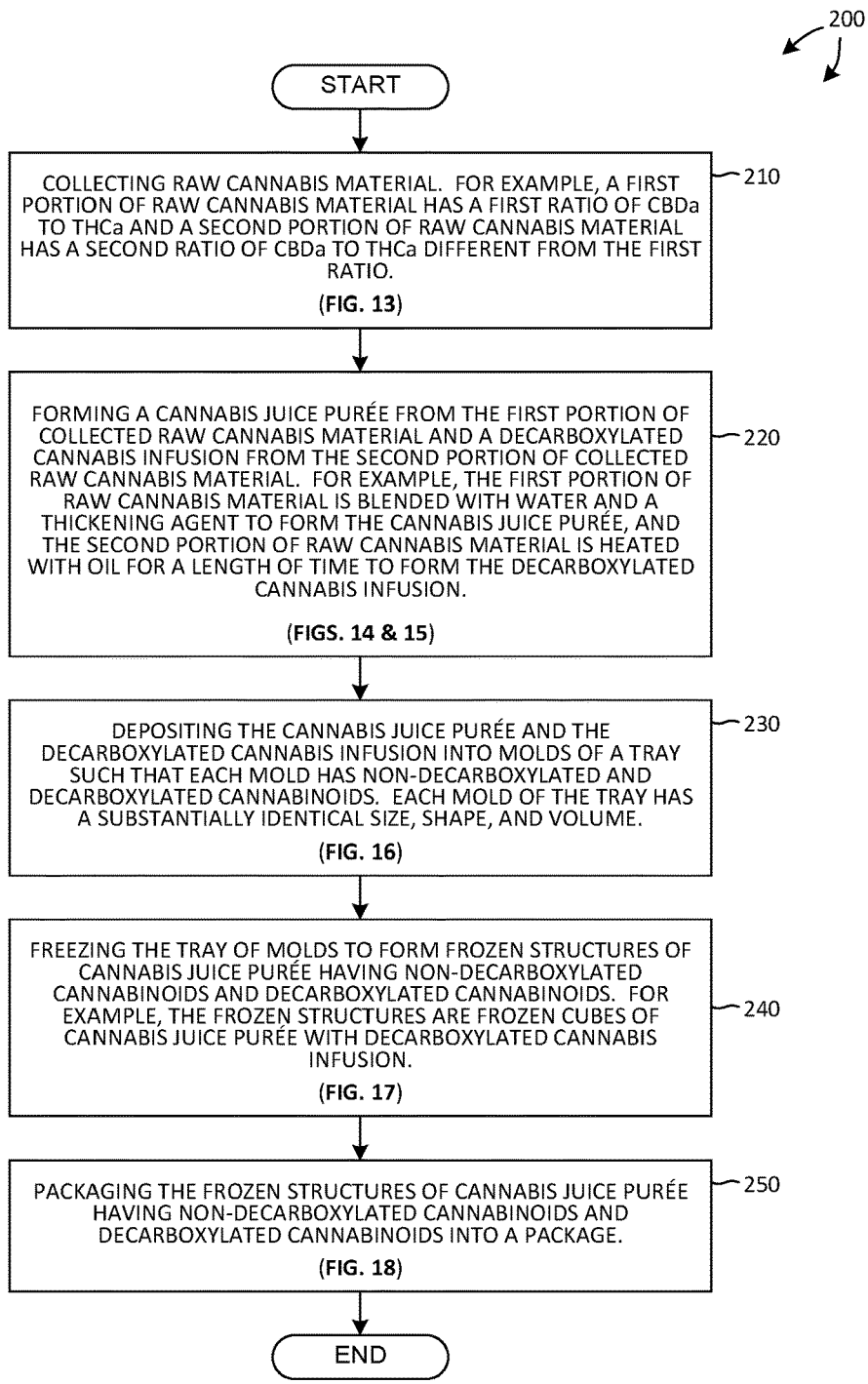
FIG. 12 is a flowchart of a method 200 in accordance with a second embodiment.

FIG. 12 is a flowchart of a method 200 in accordance with a second embodiment. The method 200 is a method of manufacturing and packaging a plurality of frozen structures of cannabis juice purée that comprises a pre-determined amount of non-decarboxylated and decarboxylated cannabinoids. The amount of decarboxylated cannabinoids in each frozen structure is at least 5 mg. A structure with less than 5 mg is not considered to be a therapeutic dose of decarboxylated cannabinoids because consuming less than 5 mg decarboxylated cannabinoids has negligible, if any, effects on the user. The amount of decarboxylated cannabinoids may include one type of decarboxylated cannabinoid (such as CBD) or more than one type of decarboxylated cannabinoid (such as CBD and THC).

Non-decarboxylated cannabinoids exhibit therapeutic benefits without psychoactive side effects. Decarboxylated cannabinoids also offer therapeutic benefits but may be considered psychoactive depending on the amount of THC present. Decarboxylated cannabinoids are typically produced by heating raw cannabis material. By providing the pre-determined amount of non-decarboxylated cannabinoids and decarboxylated cannabinoids in a single frozen structure, therapeutic results in treating certain medical conditions are achieved.

Figure 13:
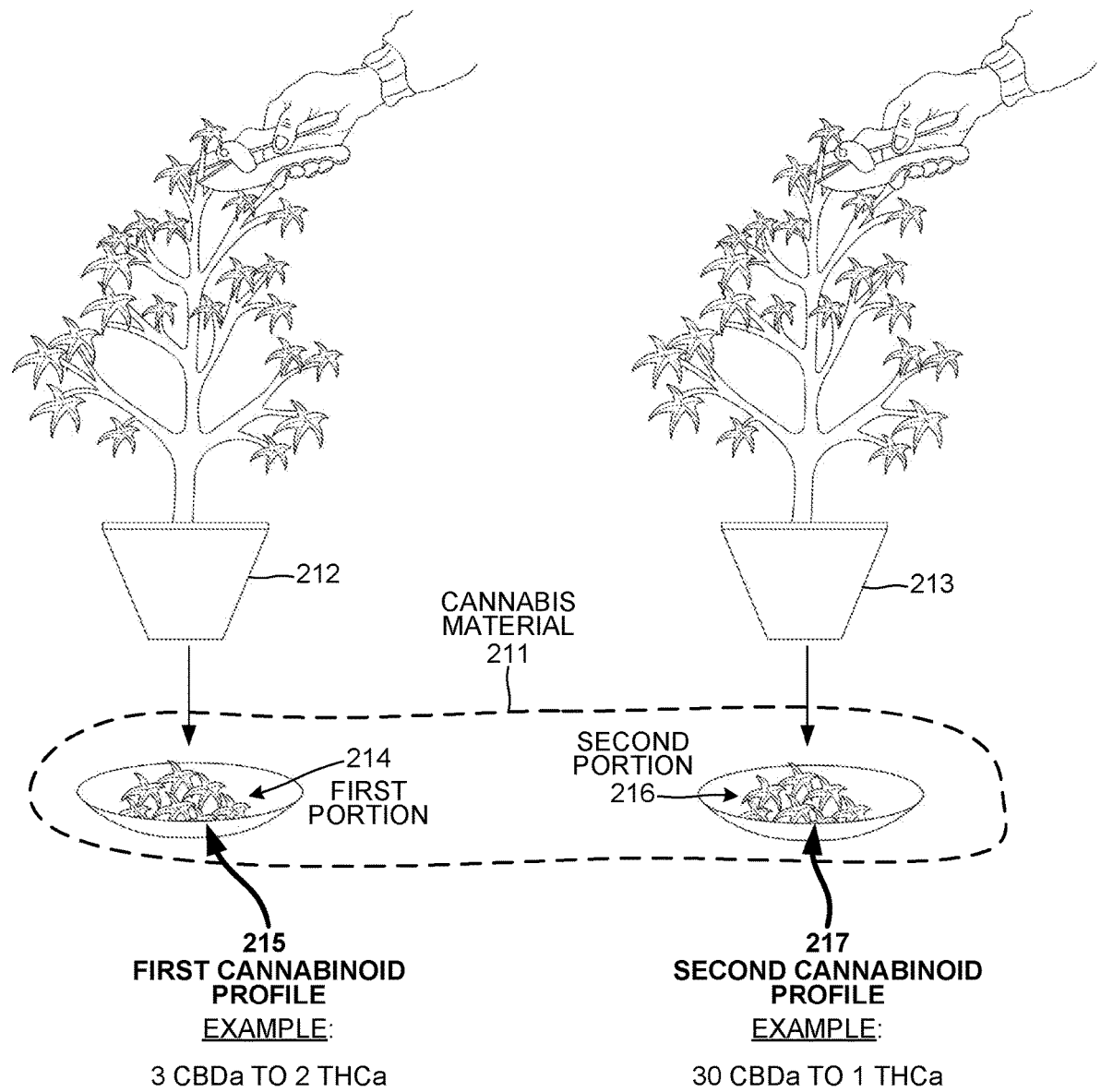
FIG. 13 is a perspective diagram showing how raw cannabis material 211 is collected from a first cannabis plant 212 and a second cannabis plant 213.

In a first step (step 210), raw cannabis material is collected. For example, in FIG. 13, raw cannabis material 211 is collected from a first cannabis plant 212 and a second cannabis plant 213. A first portion 214 of the raw cannabis material 211 is obtained from the first cannabis plant 212. The first portion 214 has a first cannabinoid profile 215 of 3 CBDa to 2 THCa. A second portion 216 of the raw cannabis material 211 is obtained from the second cannabis plant 213. The second portion 216 has a second cannabinoid profile 217 of 30 CBDa to 1 THCa. The second portion 216 of the raw cannabis material 211 will eventually be heated to obtain decarboxylated cannabinoids. At step 210, the first portion 214 and second portion 216 in FIG. 13 are non-decarboxylated as both are raw cannabis material that has not been heated.

The amounts of non-decarboxylated and decarboxylated cannabinoids can be created in unlimited combinations based on using different strains of cannabis which have different ratios of THCa and CBDa. In this example, the second portion 216 has a second cannabinoid profile 217 different from the first cannabinoid profile 215. In other embodiments, the first portion 214 and the second portion 216 have the same cannabinoid profile. Other cannabinoid profiles for the first portion include: 2 CBDa to 1 THCa, 1 CBDa to 1 THCa, 1 CBDa to 2 THCa, 1 CBDa to 3 THCa, 3 CBDa to 1 THCa, 0 CBDa to 1 THCa (no CBDa, only THCa), and 1 CBDa to 0 THCa (no THCa, only CBDa). Other cannabinoid profiles for the second portion include: 20 CBD to 1 THC, 10 CBD to 1 THC, or 5 CBD to 1 THC. A skilled artisan will appreciate that other cannabinoid profiles are obtainable.

In a second step (step 220), a non-decarboxylated cannabis juice purée is formed from the first portion of collected raw cannabis material and a decarboxylated cannabis infusion is formed from the second portion of collected raw cannabis material. Forming the non-decarboxylated cannabis juice purée does not involve heating the raw cannabis material. For example, in FIG. 14, the first portion of raw cannabis material 214 is blended in a blender 221 with water 222 and a thickening agent 223 to form a non-decarboxylated cannabis juice purée. In one example, 210.0 grams of fresh cannabis leaves 214, 200.0 grams of banana 223, and 20.0 ounces of filtered water 222 are combined in blender 221 and blended together. The blender 221 is not a juicing machine. Both the cannabis plant material and the extracted cannabis juice remain in the blender after blending and become part of the resulting cannabis juice purée. The water 222 may be filtered water, unfiltered water, ice formed from filtered water, or ice formed from unfiltered water. The thickening agent 223 aids in suspending the cannabis material yielding a more uniform mixture than would be achieved without the thickening agent 223. The thickening agent 223 may be banana, avocado, psyllium husk, tapioca, corn starch, or any other food-grade thickener.

The cannabis juice purée is formed without a juicing process. In a juicing process, a portion of the cannabis plant material is separated from the juice of the cannabis plant. At least part of the separated cannabis plant material is treated as waste and is disposed. To form the cannabis juice purée, however, all of the cannabis plant material is converted into the cannabis juice purée. The resulting cannabis juice purée includes all of the cannabis plant material placed in the blender and all of the extracted cannabis juice that is extracted in the blending process. No waste product is generated in forming the cannabis juice purée. Accordingly, the cannabis juice purée has all of the cannabis plant material and is rich in dietary fibers and non-cannabinoid components that include terpenes, fatty acids, aminoacids, enzymes, vitamins, minerals, carotenoids, chlorophyll, flavonoids, and dietary fibers.

Figure 15:
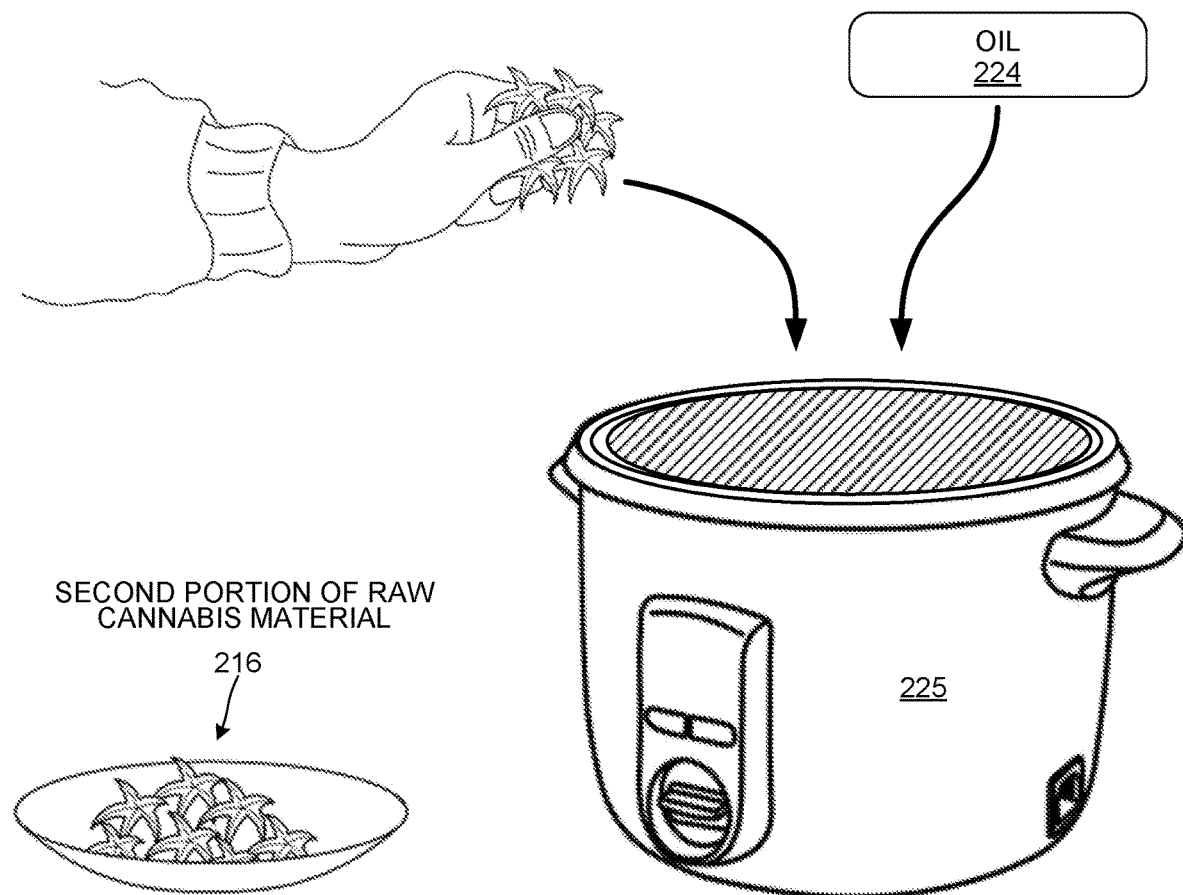
FIG. 15 is a perspective diagram showing how to make a decarboxylated cannabis infusion.

Forming the decarboxylated cannabis infusion involves heating the second portion of collected raw cannabis material. For example, in FIG. 15, the second portion of raw cannabis material 216 is heated along with fatty oil 224 in a heating mechanism 225. A typical ratio is one ounce of dried cannabis flower mixed with six cups of olive or coconut oil and is heated in a heating mechanism 225 for one to eight hours to create the decarboxylated cannabis infusion. The heating mechanism 225 shown in FIG. 15 is a crock pot.

In another example, the decarboxylated cannabinoid is generated by heating dried cannabis flower in an oven without oil. For example, the dried cannabis flower is heated in an oven at 240° F. for thirty to forty minutes. Other conventional methods for generating decarboxylated cannabis may be employed.

In a third step (step 230), the non-decarboxylated cannabis juice purée and the decarboxylated cannabis infusion are deposited into molds of a tray such that each mold has non-decarboxylated and decarboxylated cannabinoids. The tray has a plurality of molds each having a substantially identical size, shape, and volume. Depositing the cannabis juice purée and cannabis infusion into similar molds results in each cube having a substantially similar cannabinoid profile. For example, in FIG. 16, the non-decarboxylated cannabis juice purée 231 and the decarboxylated cannabis infusion 234 are deposited into molds 232 of a tray 233. First, the non-decarboxylated cannabis juice purée 231 is deposited into each mold 232 to fill approximately half of the mold 232. Next, the decarboxylated cannabis infusion 234 is deposited at a center location on the top surface of the half-filled mold. In this example, a measuring syringe 235 is employed to deposit a particular amount decarboxylated cannabis infusion 234 into the molds 232. Next, the non-decarboxylated cannabis juice purée 231 is deposited into each mold above the layer of decarboxylated cannabis infusion 234 to fill the rest of each mold 232.

Figure 16:
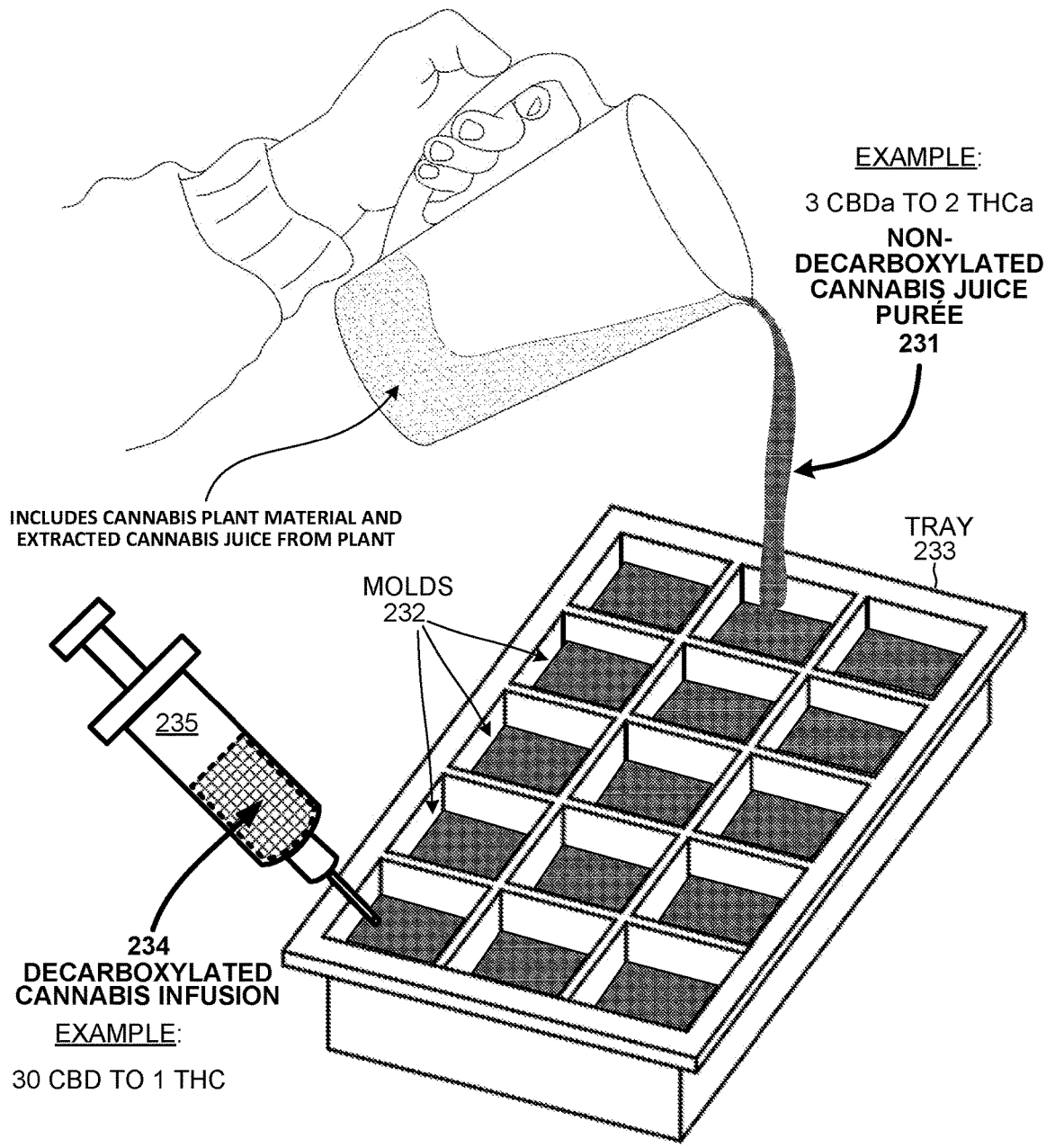
FIG. 16 is a perspective diagram showing how the non-decarboxylated cannabis juice purée 231 and the decarboxylated cannabis infusion 234 are deposited into molds 232.

In the embodiment of FIG. 16, the tray 233 has fifteen cubic shaped molds that each holds one fluid ounce. The size, shape, and volume of each mold and the number of molds on the tray are selected depending on the desired size of the frozen cannabis juice purée cubes and amount of cannabinoids to be delivered in each dose.

Figure 14:
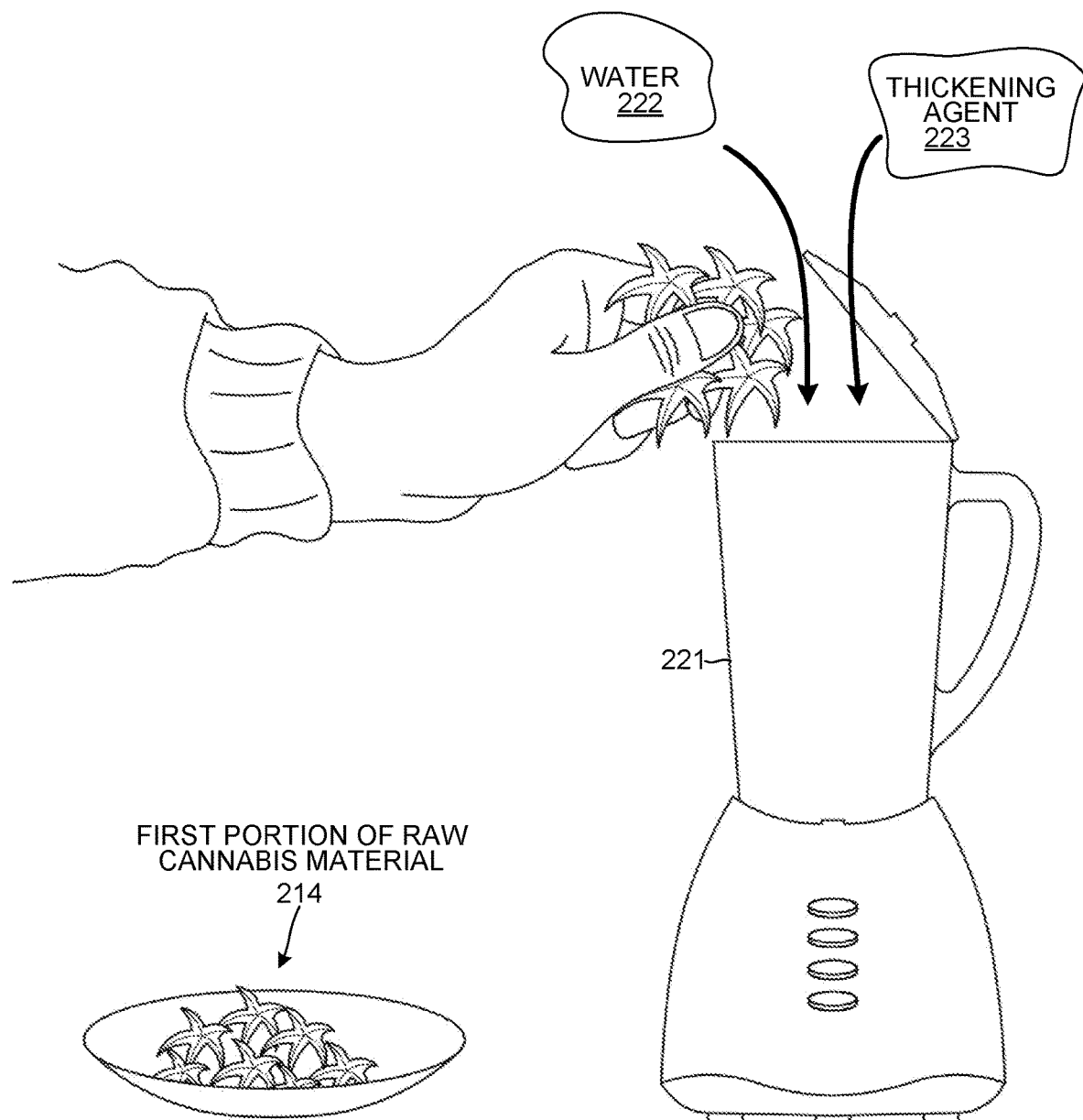
FIG. 14 is a perspective diagram showing how the non-decarboxylated cannabis juice purée is formed.

In another example, the decarboxylated cannabis infusion is deposited directly into the non-decarboxylated cannabis juice purée 231 in the blender 221 of FIG. 14. The resulting mixture has generally uniform distribution of decarboxylated cannabinoids and non-decarboxylated cannabinoids that is deposited into the molds of the tray. No syringe 235 is needed using this technique.

Figure 17:
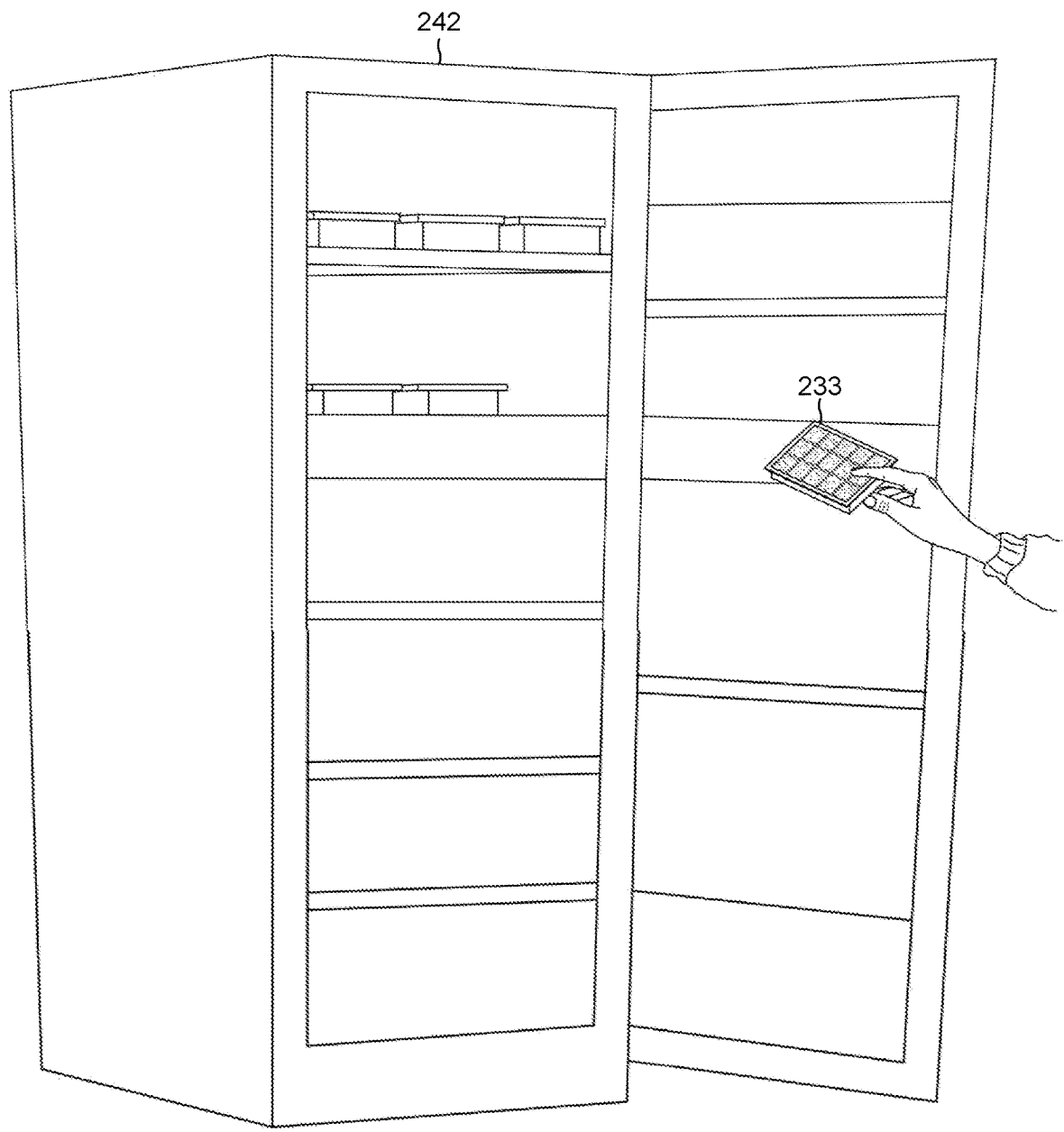
FIG. 17 is a perspective diagram showing how the tray 233 is placed in a freezer 242.

In a fourth step (step 240), the tray of molds having the cannabis juice purée and decarboxylated cannabis infusion are frozen to form frozen cannabis juice purée cubes having non-decarboxylated cannabinoids and decarboxylated cannabinoids. For example, in FIG. 17, the tray 233 having the non-decarboxylated cannabis juice purée 231 and the decarboxylated cannabis infusion 234 is placed in a freezer 242 so that the non-decarboxylated cannabis juice purée 231 and the decarboxylated cannabis infusion 234 in each mold 232 of tray 233 can freeze. The temperature within freezer 242 is typically between 0.0° F. and 5.0° F., but may be less than 0.0° F. Freezing the cannabis juice purée promotes preservation because harvested raw cannabis material is not acceptable for consumption after three days, even when the cannabis material is stored in a refrigerator. However, by freezing the cannabis juice purée to form frozen cannabis juice purée cubes, the shelf-life is extended for at least six months if the frozen cannabis juice purée cubes are properly stored in a freezer.

Figure 18:
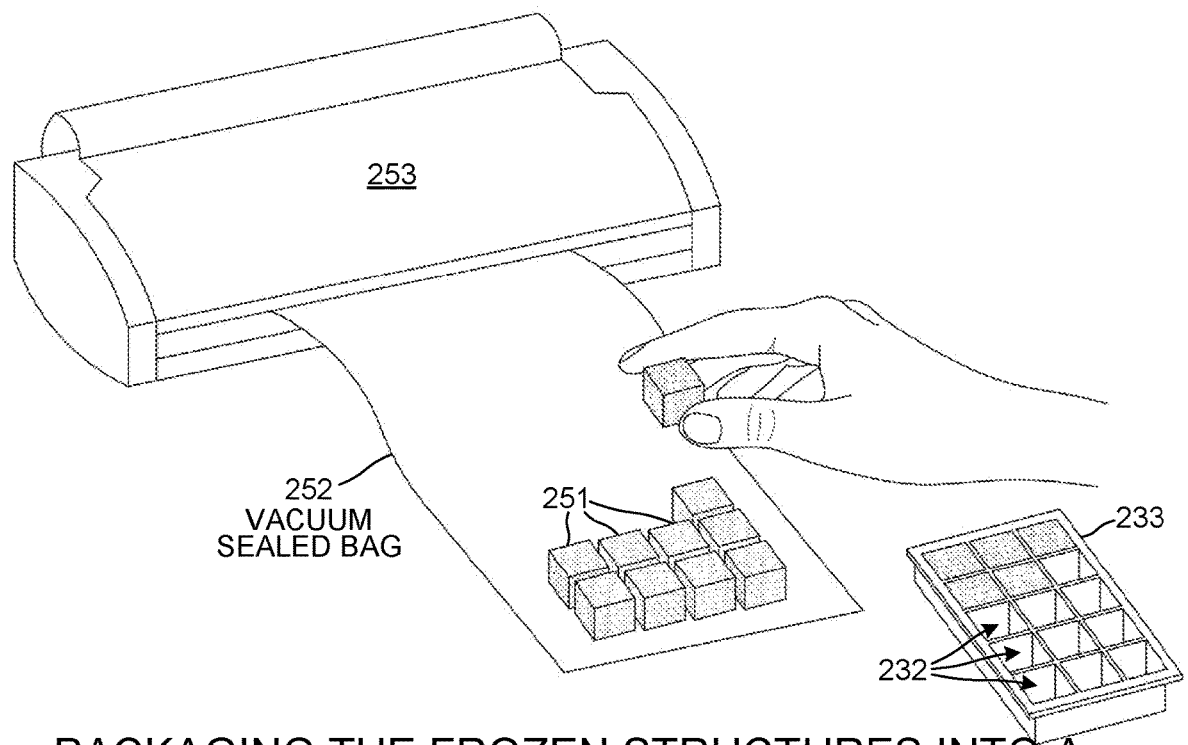
FIG. 18 is a perspective diagram showing how the frozen cannabis juice purée cubes 251 are removed from the tray 233 and placed on vacuum sealed bag 252.

In a fifth step (step 250), the cubes having non-decarboxylated cannabinoids and decarboxylated cannabinoids are packaged into a package. The frozen cannabis juice purée cubes are packaged in a vacuum sealed package, a bag, or a container having a detachable lid. For example, in FIG. 18, the frozen cannabis juice purée cubes 251 are removed from the molds 232 of the tray 233 and are placed on vacuum sealed bag 252. The vacuum sealed bag 252 is sealed by vacuum sealing machine 253 to form a vacuum sealed package having the frozen cannabis juice purée cubes 251.

Figure 19:
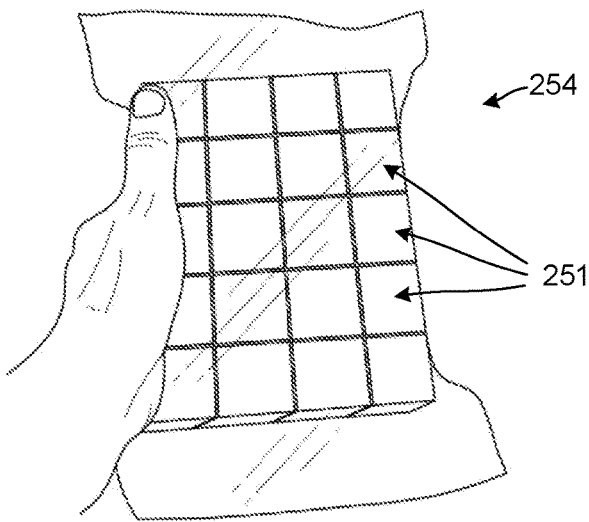
FIG. 19 is a perspective diagram of a package 254 with the frozen cannabis juice purée cubes 251.

FIG. 19 is a perspective diagram of a package 254 with the frozen cannabis juice purée cubes 251. The frozen cannabis juice purée cubes 251 have non-decarboxylated cannabinoids and decarboxylated cannabinoids. The package 254 delivers the frozen cannabis juice purée cubes 251 cheaply because the only packaging material involved is the vacuum sealed bag 252. The package 254 provides for optimal storing, packing, and transporting because the packages are rectangular or square and have flat surfaces that allow the packages to be stacked above each other. The frozen cannabis juice purée cubes 251 consume over 95% of the total volume of package 254 allowing for maximum delivery of frozen cannabis juice purée cubes per shipment of packages.

Figure 20:
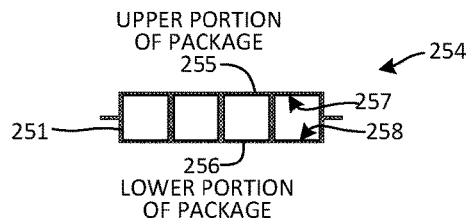
FIG. 20 is a side view of the package 254 with the frozen cannabis juice purée cubes 251.

FIG. 20 is a side view of the package 254 with the frozen cannabis juice purée cubes 251. The package 254 has an upper portion 255 and a lower portion 256. Each of the cubes 251 has an upper surface 257 and a lower surface 258. Each upper surface 257 of the cubes contacts the upper portion 255 of the package 254 and each lower surface 258 of the cubes 251 contacts a lower portion 256 of the package 254. No packaging material is disposed within the package.

Figure 21:
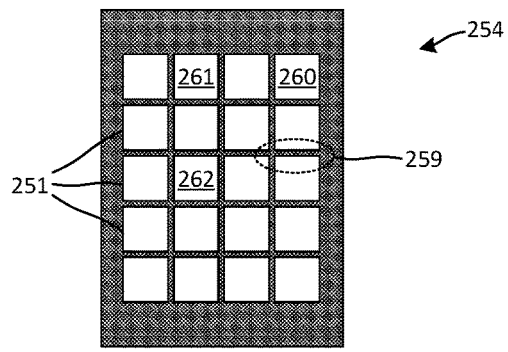
FIG. 21 is top view of the package 254 with the frozen cannabis juice purée cubes 251.

FIG. 21 is top view of the package 254 with the frozen cannabis juice purée cubes 251. The frozen cannabis juice purée cubes 251 are packaged in an array formation. Each of the frozen cannabis juice purée cubes 251 has a substantially identical shape and each cube is adjacent to at least one other cube. Reference numeral 259 identifies a surface of one cube adjacent to a surface of another of the cubes. Each frozen cannabis juice purée cube has at least two surfaces that are adjacent to surfaces of at least two other cubes.

Reference numeral 260 identifies a frozen cannabis juice purée cube along a corner of the array of cubes 251 having a first surface that is adjacent to a surface of a second cube and a second surface that is adjacent to a surface of a third cube. Cube 260 has two surfaces each of which contacts a surface of one of two other cubes. Reference numeral 261 identifies a frozen cannabis juice purée cube along an edge of the array of cubes 251 having a first surface that is adjacent to a surface of a second cube, a second surface that is adjacent to a surface of a third cube, and a third surface that is adjacent to a surface of a fourth cube. Cube 261 has three surfaces each of which contacts a surface of one of three other cubes. Reference numeral 262 identifies a frozen cannabis juice purée cube at an inner portion of the array of cubes 251 having a first surface that is adjacent to a surface of a second cube, a second surface that is adjacent to a surface of a third cube, a third surface that is adjacent to a surface of a fourth cube, and a fourth surface that is adjacent to a surface of a fifth cube. Cube 262 has four surfaces each of which contacts a surface of one of four other cubes.

In accordance with at least one novel aspect, the frozen cannabis juice purée cubes 251 are not contained in separate containers. No packaging material is present between the frozen cannabis juice purée cubes 251. Although a gap is shown between the cubes 251, some or all of the cubes 251 may be directly contacting each other. The tight packing of the cubes 251 significantly reduces packaging, storing, and shipping costs.

In another example, the frozen cannabis juice purée cubes 251 are loosely packed in a bag without vacuum sealing. Costs and packaging time are substantially reduced by not vacuum sealing. Not all of the cubes contact a surface of the bag. Some of the cubes in the bag are surrounded by other cubes and do not touch a surface of the bag. In yet another example, the frozen cannabis juice purée cubes 251 are loosely packed in a plastic container having a lid. Not all of the cubes contact a surface of the plastic container. Depending on the size of the container, the cubes may not contact the lid of the container.

Figure 22A:
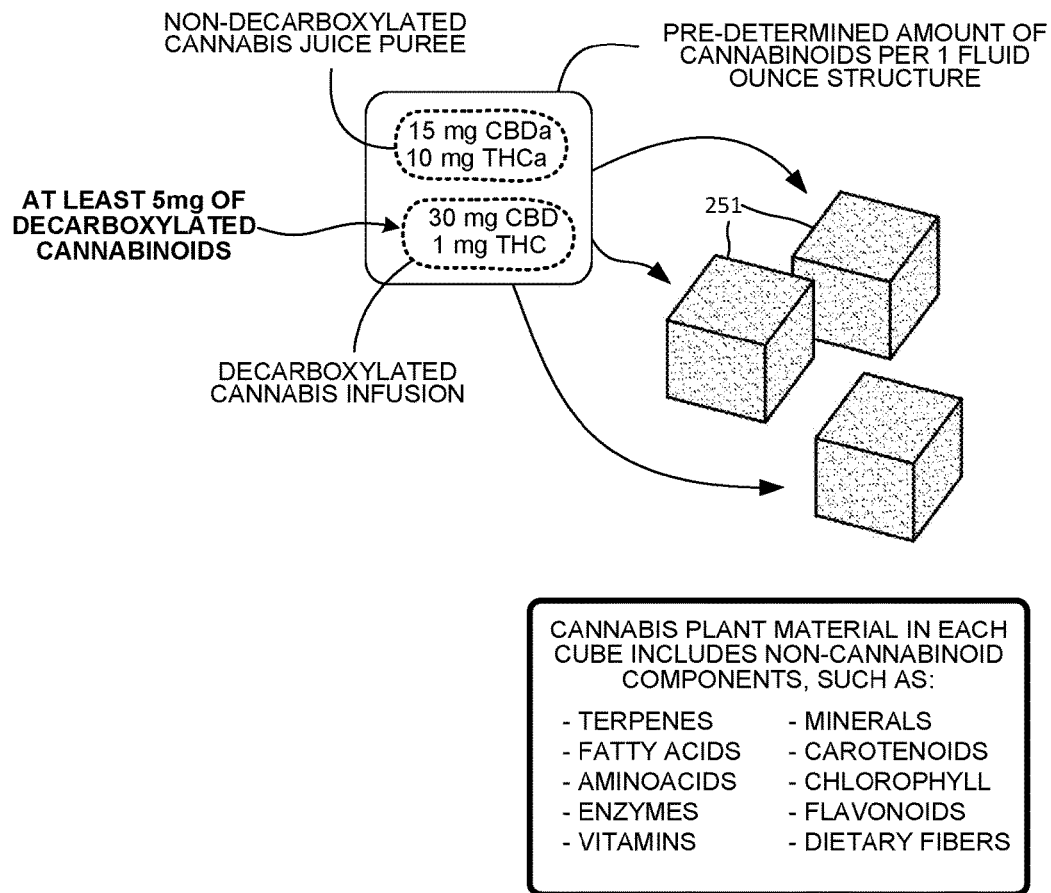
FIG. 22A is a perspective diagram of frozen cannabis juice purée cubes 251 having an amount of non-decarboxylated cannabinoids and an amount of decarboxylated cannabinoids.

FIG. 22A is a perspective diagram of frozen cannabis juice purée cubes 251 having an amount of non-decarboxylated cannabinoids and an amount of decarboxylated cannabinoids. The amount of non-decarboxylated cannabinoids comprises an amount of tetrahydrocannabinolic acid (THCa) and an amount of cannabidiolic acid (CBDa). The amount of decarboxylated cannabinoids comprises an amount of tetrahydrocannabinol (THC) and an amount of cannabidiol (CBD). Each of cubes 251 is a frozen cube of one fluid ounce and has 10 mg of THCa, 1 mg of THC, 15 mg of CBDa, and 30 mg of CBD. In this example, the ratio of CBDa to THCa is 3:2 and the ratio of CBD to THC is 30:1. The amount of CBDa in each cube is greater than the amount of THCa, and the amount of CBD in each cube is greater than the amount of THC. The frozen cannabis juice purée cubes may be made to include or exclude non-cannabinoid components that include terpenes, fatty acids, aminoacids, enzymes, vitamins, minerals, carotenoids, chlorophyll, flavonoids, and dietary fibers.

Figure 22B:
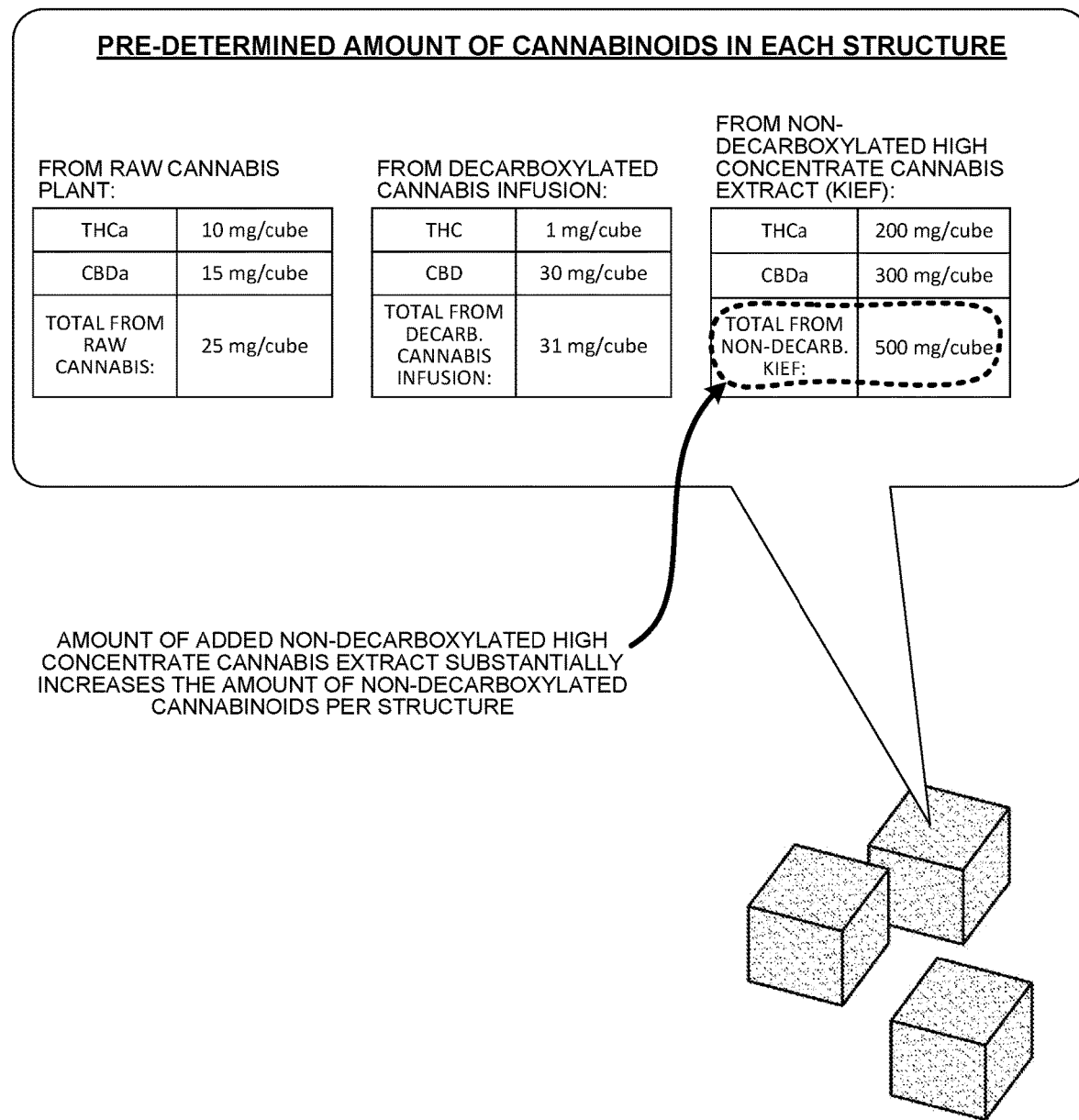
FIG. 22B is a perspective diagram of another embodiment of frozen structures of cannabis juice purée with added decarboxylated cannabis infusion and non-decarboxylated high concentrate cannabis extract.

FIG. 22B is a perspective diagram of another embodiment of frozen structures of cannabis juice purée having decarboxylated cannabis infusion and non-decarboxylated high concentrate cannabis extract. In the example of FIG. 22B, the frozen structures have 25 mg of non-decarboxylated cannabinoids from raw cannabis plant, 31 mg of decarboxylated cannabinoids from decarboxylated cannabis infusion, 500 mg of non-decarboxylated cannabinoids from non-decarboxylated high concentrate cannabis extract. The added amount of non-decarboxylated high concentrate cannabis extract substantially increases the amount of cannabinoids in each frozen structure. In this example, the non-decarboxylated high concentrate cannabis extract adds an additional 500 mg of non-decarboxylated cannabinoids in each structure. The amount of non-decarboxylated cannabinoids from the non-decarboxylated high concentrate cannabis extract is at least ten times the amount of non-decarboxylated cannabinoids derived from the raw cannabis plant. The high concentrate cannabis extract is obtained through numerous processes and included in the frozen structures as explained above in connection with FIG. 10B.

Figure 22C:
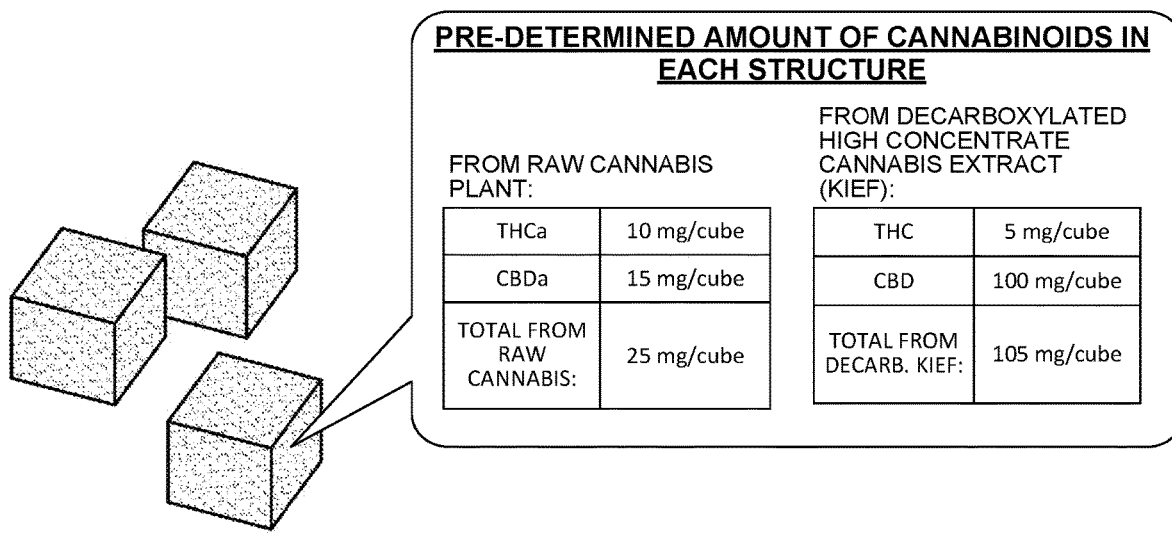
FIG. 22C is a perspective diagram of another embodiment of frozen structures of cannabis juice purée with added decarboxylated high concentrate cannabis extract.

FIG. 22C is a perspective diagram of another embodiment of frozen structures of cannabis juice purée having decarboxylated high concentrate cannabis extract. In the example of FIG. 22C, the frozen structures have 25 mg of non-decarboxylated cannabinoids from raw cannabis plant and 105 mg of decarboxylated cannabinoids from decarboxylated high concentrate cannabis extract. The added amount of decarboxylated high concentrate cannabis extract substantially increases the amount of cannabinoids in each frozen structure. In this example, the decarboxylated high concentrate cannabis extract adds an additional 105 mg of decarboxylated cannabinoids to each structure. The decarboxylated high concentrate cannabis extract is obtained by heating the high concentrate cannabis extract obtained through numerous processes described above in connection with FIG. 10B. A few techniques are described below.

The high concentrate cannabis extract is decarboxylated by first heating the non-decarboxylated high concentrate cannabis extract on a dish in an oven at temperatures between 212° F. and 340° F. The high concentrate cannabis extract becomes decarboxylated as a result of heating thus converting the THCa and CBDa to THC and CBD, respectively, as well as other decarboxylated cannabinoids. This results in a substantially high potency of THC and CBD, for example, approximately 30% and 60% decarboxylated cannabinoids per gram. In a second technique, the cannabis flower and flower trim can also be decarboxylated in an oven at temperatures between 212° F. and 340° F. This would result in plant material being decarboxylated at between about 10% and 30% decarboxylated cannabinoids per gram. The percentage yield in this technique is less due to plant material. In a third technique, the high concentrate cannabis extract or cannabis flower can also be added to a food grade oil mixture and heated to between 212° F. and 340° F. Such food grade oil mixture is selected from the group consisting of olive oil, coconut oil, avocado oil, or similar cooking oil. A crockpot or pressure cooker can be employed to heat the oils. The result of this technique is an infused oil that contains decarboxylated cannabinoids comprising between 100 mg and 300 mg of cannabinoids per fluid ounce.

To incorporate the decarboxylated high concentrate cannabis into the frozen structures, several techniques may be employed. In one example, while pouring the cannabis juice purée into the molds, an amount of decarboxylated high concentrate cannabis extract is weighed and added into each of the individual molds. For example, the cannabis juice purée is filled to half the volume of the mold. Next, the decarboxylated high concentrate cannabis extract is deposited. Next, the remainder of the mold is filled with the cannabis juice purée. This would maintain the decarboxylated high concentrate cannabis extract within a center of the frozen frozen cannabis juice purée cubes. In another example, while blending the raw cannabis material, decarboxylated high concentrate cannabis extract is added to the entire cannabis juice purée. The resulting cannabis juice purée would have a uniform amount of the decarboxylated high concentrate cannabis extract. This is not as preferred, as some of the valuable decarboxylated high concentrate cannabis extract could be lost in the residue on the side of the mixing or blending apparatus. Depending on the potency desired, any amount of decarboxylated high concentrate cannabis extract can be added to the cannabis juice purée.

The amounts and types of cannabinoids varies and is selected according to the desired potency and amount desired. For example, non-decarboxylated frozen cannabis juice purée cubes that do not have the high concentrate cannabis extract range between 5 mg and 200 mg of non-decarboxylated cannabinoid per fluid ounce of cube. Non-decarboxylated frozen cannabis juice purée cubes that do have the high concentrate cannabis extract range between 5 mg and 2,500 mg of non-decarboxylated cannabinoid per fluid ounce of cube. Decarboxylated frozen cannabis juice purée cubes that have the high concentrate cannabis extract range between 5 mg and 2,500 mg of non-decarboxylated cannabinoids per fluid ounce of cube and between 5 mg and 2,500 mg of decarboxylated cannabinoids per fluid ounce of cube. Decarboxylated frozen cannabis juice purée cubes that have the decarboxylated oil or flower described above range between 5 mg and 2,500 mg of non-decarboxylated cannabinoids per fluid ounce of cube and between 5 mg and 2,500 mg of decarboxylated cannabinoids per fluid ounce of cube.

Figure 22D:
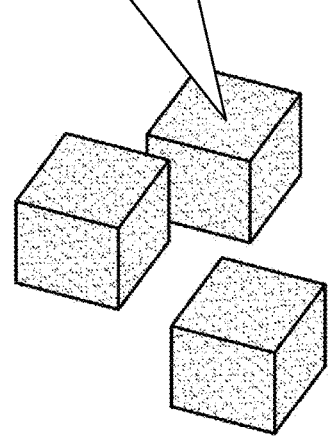
FIG. 22D is a perspective diagram of another embodiment of frozen structures of cannabis juice purée with added decarboxylated high concentrate cannabis extract and non-decarboxylated high concentrate cannabis extract.

FIG. 22D is a perspective diagram of another embodiment of frozen structures of cannabis juice purée having decarboxylated high concentrate cannabis extract and non-decarboxylated high concentrate cannabis extract. In the example of FIG. 22D, the frozen structures have 25 mg of non-decarboxylated cannabinoids from raw cannabis plant, 105 mg of decarboxylated cannabinoids from decarboxylated high concentrate cannabis extract, and 500 mg of non-decarboxylated cannabinoids from non-decarboxylated high concentrate cannabis extract.

Figure 23:
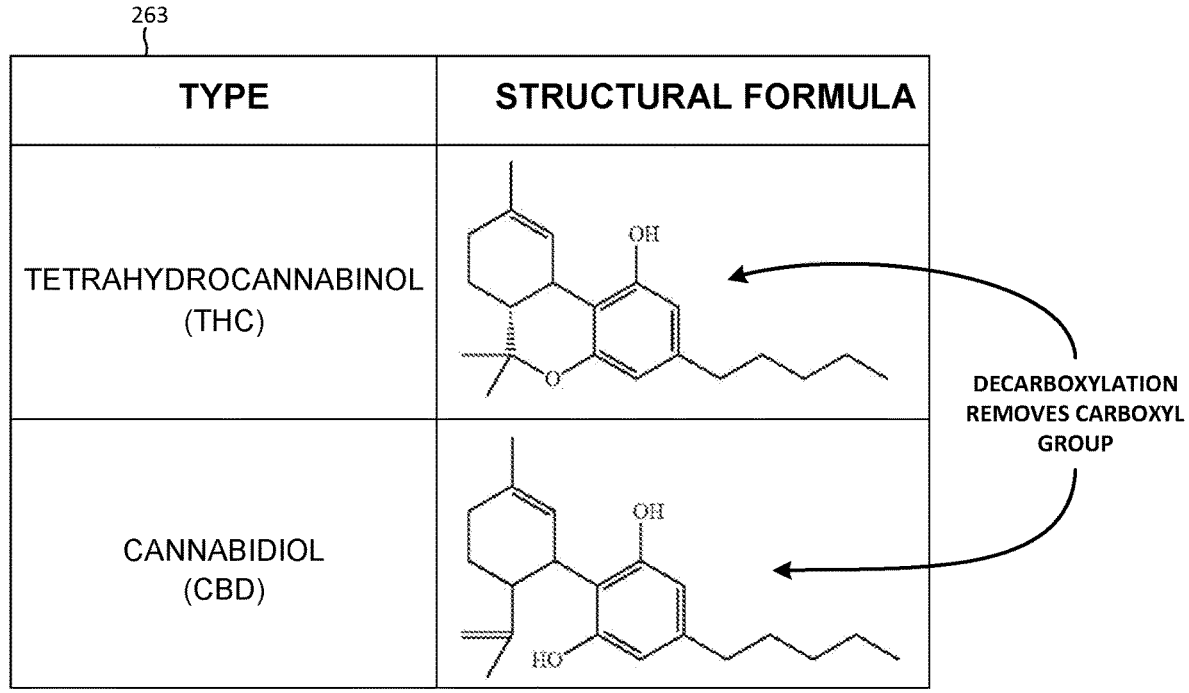
FIG. 23 is a table 263 showing two general types of decarboxylated cannabinoids, THC and CBD, along with their chemical names and structural formulas.

FIG. 23 is a table 263 showing two general types of decarboxylated cannabinoids, THC and CBD, along with their chemical names and structural formulas. The decarboxylated cannabinoids are formed through a decarboxylation process that removes the carboxyl group (COOH).

Figure 24:
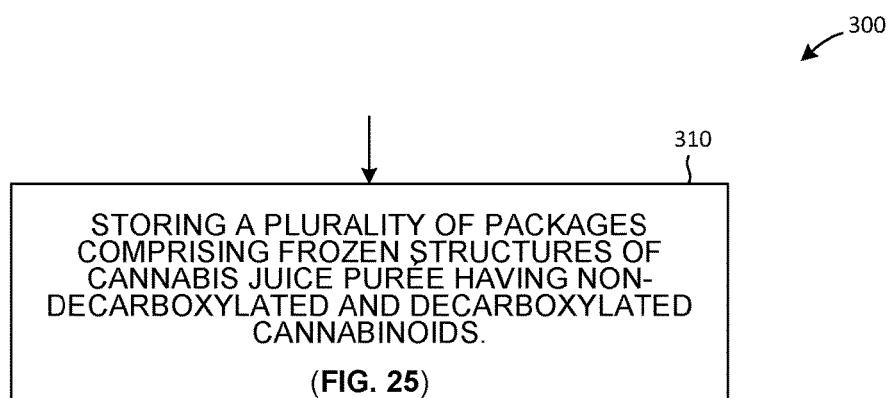
FIG. 24 is a flowchart of a method 300 in accordance with another novel aspect.
Figure 25:
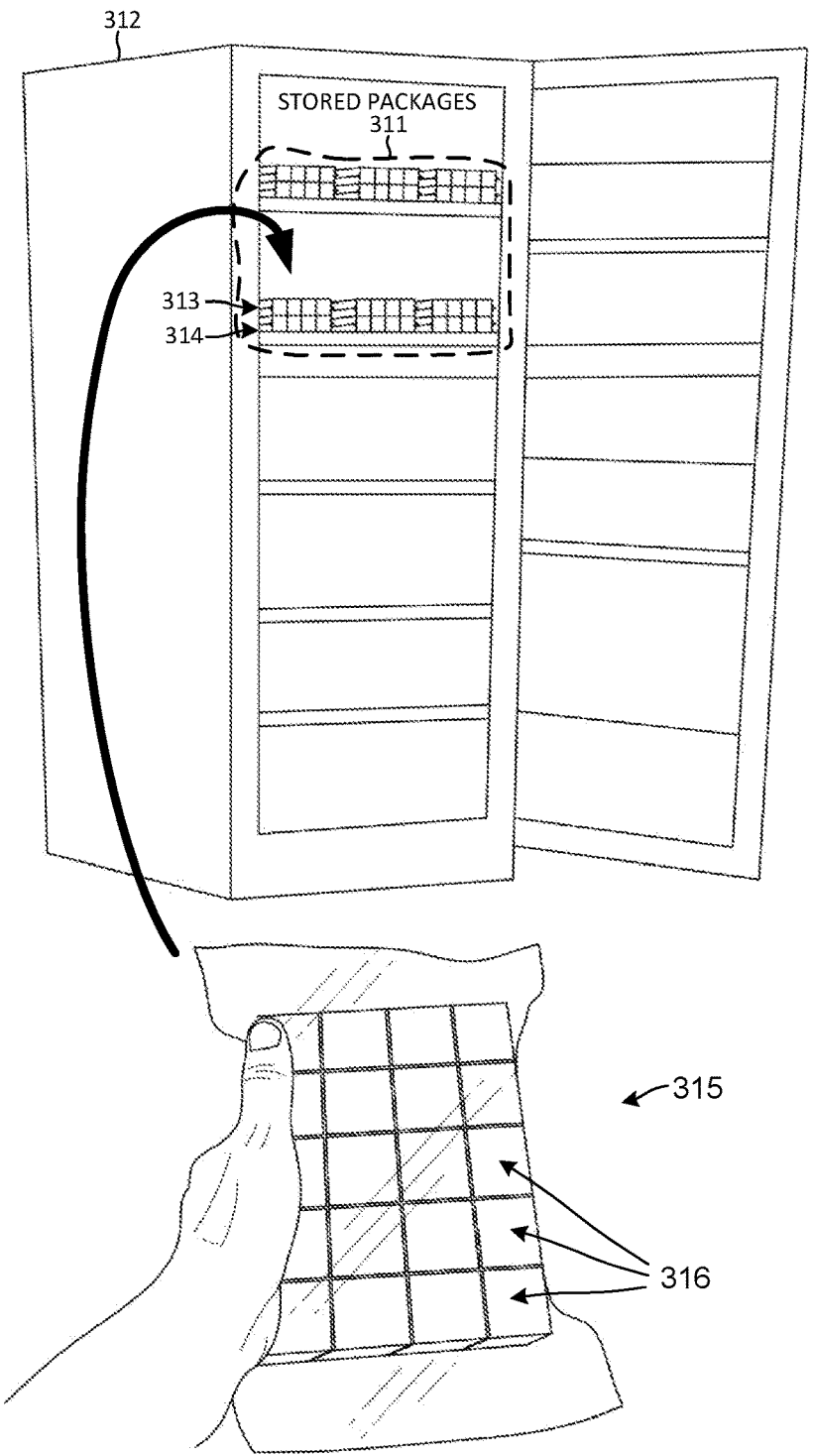
FIG. 25 is a perspective diagram showing how a plurality of packages 311 is stored in a freezer 312.

FIG. 24 is a flowchart of a method 300 in accordance with another novel aspect. In a first step (step 310), a plurality of packages having frozen structures of cannabis juice purée is stored. For example, in FIG. 25, a plurality of packages 311 is stored in a freezer 312. The packages are 311 are stored by stacking each package above another package. For example, package 313 is disposed above package 314. Package 315 is to be placed above package 313. Each of the packages comprises a plurality of frozen cannabis juice purée cubes 316. At least one of the frozen cannabis juice purée cubes contacts the package. Each package has at least two flat surfaces due to the uniform size and shape of each cube 316. Accordingly, the packages 311 stack compactly in the freezer 312. If, on the other hand, the cubes within in each package were not uniform in size and shape, then the packages would not have flat surfaces adapted for stacking. Additionally, by not placing each cube in a separate package and by not including any additional packaging materials between the package 315 and each cube 316, each package consumes minimal space in freezer 312 thereby increasing the number of packages that can be stored per unit volume of storage capacity.

Figure 26:
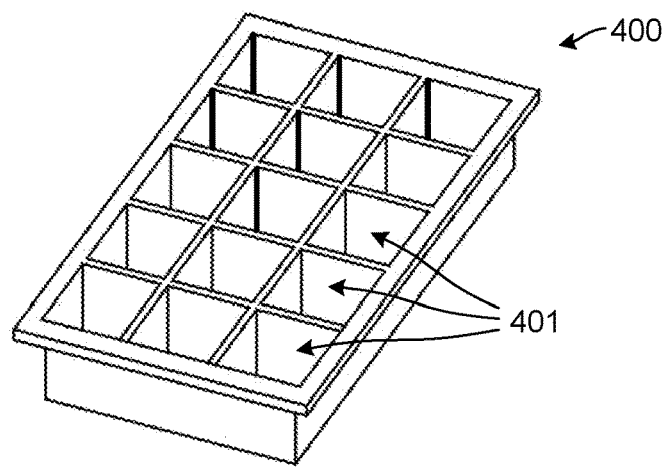
FIG. 26 is a perspective diagram of a tray 400 having a plurality of molds 401.

FIG. 26 is a perspective diagram of a tray 400 having a plurality of molds 401. All of the molds 401 have a substantially identical structure thereby yielding cubes having a consistent size and dosage of cannabinoids. In this example, each mold is cubic shaped and holds one fluid ounce. In other embodiments, the molds may be smaller or larger depending on the desired size of the cubes. The volume of each mold 401 is typically between 0.125 cubic inches (0.5 inches×0.5 inches×0.5 inches) and 8.0 cubic inches (2.0 inches×2.0 inches×2.0 inches). An artisan of ordinary skill appreciates that the molds may be larger or shaped differently. Other trays may be selected that frozen structures of cannabis juice purée of between 0.1 fluid ounce and 5.0 fluid ounces of cannabis juice purée.

Figure 27:
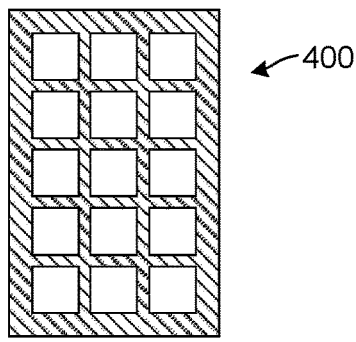
FIG. 27 is a top view of the tray 400 having a plurality of molds 401.

FIG. 27 is a top view of the tray 400 having a plurality of molds 401.

Other frozen structures of cannabis juice purée may be formed having different shapes. FIGS. 28-36 show how the frozen structures may be formed into various other shapes that are non-cubic.

Figure 28:
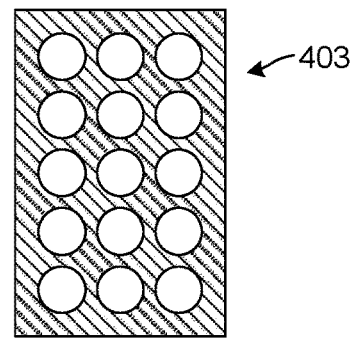
FIG. 28 is a top view of a tray 403 having a plurality of cylindrical shaped molds.

FIG. 28 is a top view of a tray 403 having a plurality of cylindrical shaped molds.

Figure 29:
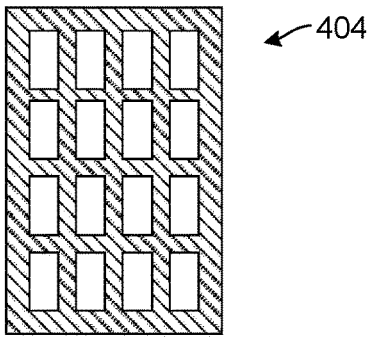
FIG. 29 is a top view of a tray 404 having a plurality of rectangular shaped molds.

FIG. 29 is a top view of a tray 404 having a plurality of rectangular shaped molds.

Figure 30:
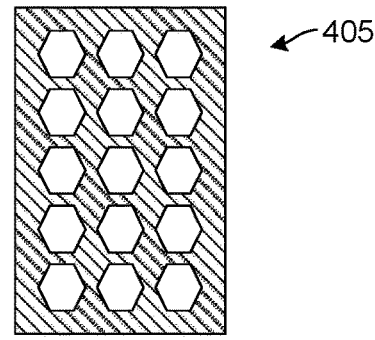
FIG. 30 is a top view of a tray 405 having a plurality of hexagonal shaped molds.

FIG. 30 is a top view of a tray 405 having a plurality of hexagonal shaped molds.

Figure 31:
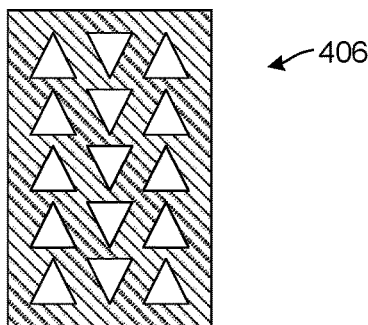
FIG. 31 is a top view of a tray 406 having a plurality of triangular shaped molds.

FIG. 31 is a top view of a tray 406 having a plurality of triangular shaped molds.

Figure 32:
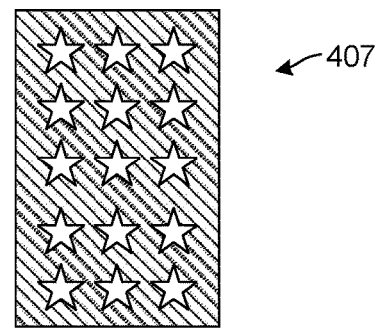
FIG. 32 is a top view of a tray 407 having a plurality of star shaped molds.

FIG. 32 is a top view of a tray 407 having a plurality of star shaped molds.

Figure 33:
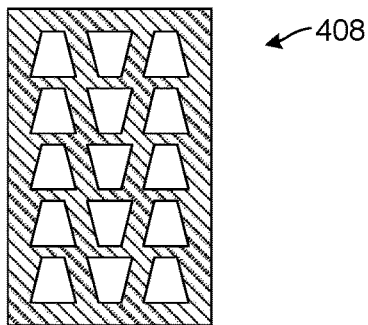
FIG. 33 is a top view of a tray 408 having a plurality of trapezoidal shaped molds.

FIG. 33 is a top view of a tray 408 having a plurality of trapezoidal shaped molds.

Figure 34:
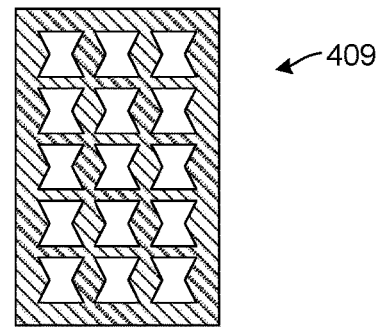
FIG. 34 is a top view of a tray 409 having a plurality of concave shaped molds.

FIG. 34 is a top view of a tray 409 having a plurality of concave shaped molds.

Figure 35:
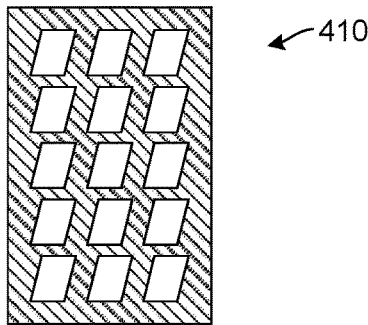
FIG. 35 is a top view of a tray 410 having a plurality of parallelogram shaped molds.

FIG. 35 is a top view of a tray 410 having a plurality of parallelogram shaped molds.

Figure 36:
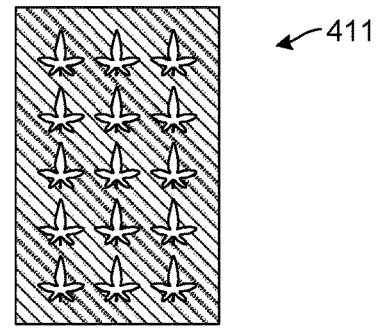
FIG. 36 is a top view of a tray 411 having a plurality of leaf shaped molds.

FIG. 36 is a top view of a tray 411 having a plurality of leaf shaped molds.

FIG. 37 is a diagram of a conventional coconut milk based cannabis ice cream 420. The coconut milk based cannabis ice cream 420 is packaged in a container 421 having a lid 422. The conventional coconut milk based cannabis ice cream 420 is available from Ohana Farms at (http://www.ohanaedu.org/index.php/products/cbd-cubes/). The conventional coconut milk based cannabis ice cream 420 has a soft, ice-cream texture and requires separate packaging for each dose of ice cream 420.

FIG. 38 is a diagram showing how the container 421 is placed onto a container holder 423. The container holder 423 includes a retainer opening 424 into which the container 421 is placed. The container holder 423 includes six retainer openings and holds up to six of the containers 421.

FIG. 39 is a diagram showing how the container holder 423 having six containers is placed into a package 425. The container holder 423 having the six containers is inserted via opening 426. After the container holder 423 having the six containers is inside the package 425, the package 425 is sealed.

FIG. 40 is a diagram of the package 425 containing the container holder 423 having the six containers with coconut milk based cannabis ice creams.

FIG. 41 is a table 500 showing the advantages of novel package 154 (shown in FIG. 7) and novel package 254 (shown in FIG. 19) over the conventional package 425 shown in FIG. 40. The novel packages 154 and 254 exhibit advantages with respect to storage capacity, packaging costs, waste generation, and quantity of cubes per package.

The novel packages 154 and 254 utilize minimal storage capacity as compared to the conventional package 425. The novel packages 154 and 254 have at least two flat surfaces allowing several of the novel packages 154 and 254 to be stacked above each other. The conventional package 425, on the other hand, does not have flat surfaces and does not provide an advantageous utilization of storage space.

The novel packages 154 and 254 involve minimal packaging costs as compared to the conventional package 425. The only packaging involved is the vacuum seal bag, resealable bag, or container in which the novel cubes are stored. At least one of the frozen cannabis juice purée cubes contacts the package. No additional packaging is inserted between the cubes. No additional packaging is inserted between the cubes and the outer package. The conventional package 425, on the other hand, has substantial packaging. For example, each cannabinoid structure is individually packaged in a separate container and covered with a lid. In addition, each of the individual containers is then placed onto a holder. Therefore, the conventional package 425 has significantly greater packaging costs than the novel packages 154 and 254.

The novel packages 154 and 254 generate minimal waste as compared to the conventional package 425. The novel packages 154 and 254 only generate waste from a single package, such as a bag, vacuum sealed bag, or container. The novel packages 154 and 254 may have a label disposed on an outer surface, but no other waste is generated because the entire contents of the novel packages 154 and 254 are consumed. The conventional package 425, on the other hand, generates substantial waste as compared to the novel packages 154 and 254 because of all of the packaging, including six containers, six lids, the container holder, and the outer packaging.

The novel packages 154 and 254 deliver significantly more cannabinoids per unit volume of packaging as compared to the conventional package 425. A single one of the novel packages 154 and 254 delivers twenty cubes due, in part, to the minimal packaging involved. The conventional package 425, on the other hand, only carries six coconut milk based cannabis ice creams.

Figure 42:
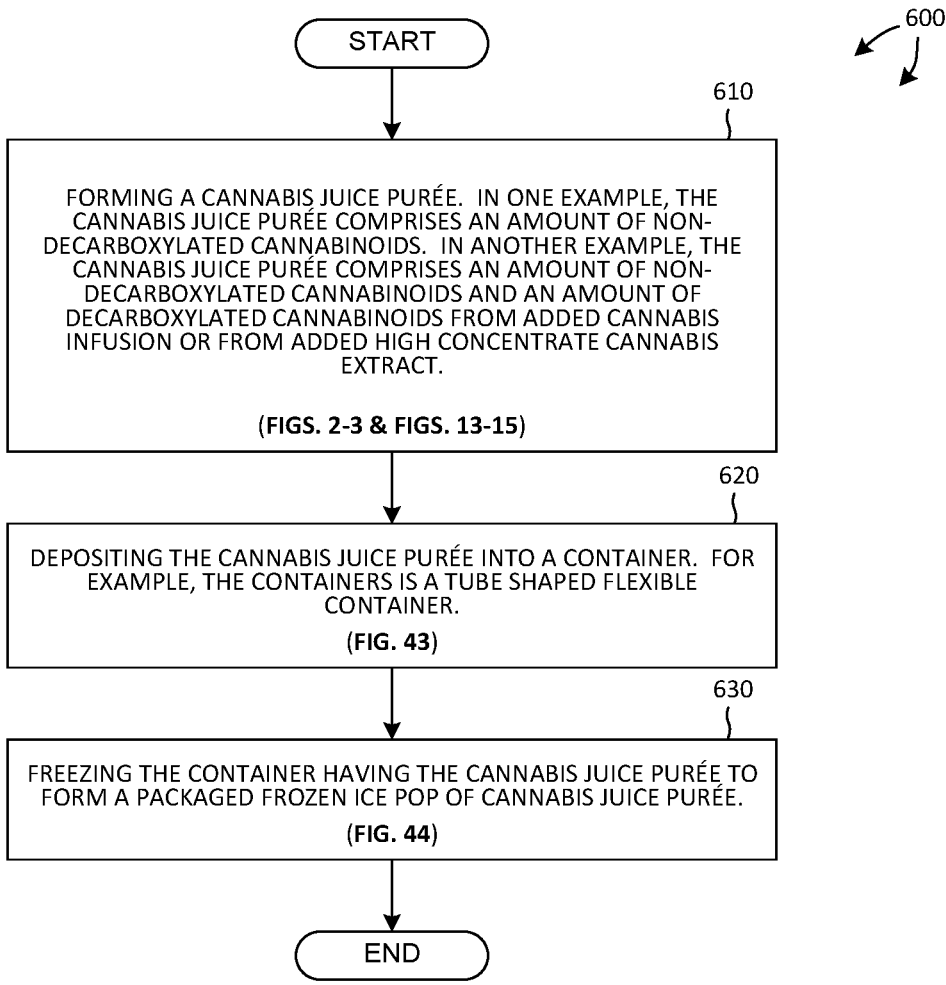
FIG. 42 is a flowchart of a method 600 in accordance with a third embodiment.

FIG. 42 is a flowchart of a method 600 in accordance with a third embodiment. The method 600 is a method of manufacturing and packaging a frozen ice pop of cannabis juice purée. In one specific embodiment, the packaged frozen ice pop of cannabis juice purée has an amount of non-decarboxylated cannabinoids and is non-psychoactive. In another specific embodiment, the packaged frozen ice pops of cannabis juice purée has an amount of non-decarboxylated cannabinoids and an amount of decarboxylated cannabinoids. The amount of decarboxylated cannabinoids in each ice pop is at least 5 mg. Decarboxylated cannabis infusion, non-decarboxylated high concentrate cannabis extract, or decarboxylated high concentrate cannabis extract are optionally added to the frozen ice pops of cannabis juice purée.

In a first step (step 610), a cannabis juice purée is formed. To form a frozen ice pop of cannabis juice purée that is non-psychoactive, raw cannabis material having an amount of non-decarboxylated cannabinoids is collected. For example, in FIG. 2, raw cannabis material 112 is collected by trimming leaves 113 from the cannabis plant 111, and in FIG. 3, the raw cannabis material 112 is blended in a blender 121 with water 122 and a thickening agent 123 to form a cannabis juice purée.

To form a packaged frozen ice pop of cannabis juice purée that has decarboxylated cannabinoids, a portion of the collected raw cannabis material is heated. For example, in FIG. 13, raw cannabis material 211 is collected from a first cannabis plant 212 and a second cannabis plant 213. A first portion 214 of the raw cannabis material 211 is obtained from the first cannabis plant 212. Next, the first portion of raw cannabis material 214 is blended in a blender 221 with water 222 and a thickening agent 223 to form a non-decarboxylated cannabis juice purée as shown in FIG. 14. Next, a second portion 216 of the raw cannabis material 211 is obtained from the second cannabis plant 213 as shown in FIG. 13. Next, the second portion of collected raw cannabis material is heated to form a decarboxylated cannabis infusion, as shown for example in FIG. 15. The non-decarboxylated cannabis juice purée and decarboxylated cannabis infusion are combined prior to freezing.

In both the non-decarboxylated and decarboxylated embodiments of the packaged frozen ice pop of cannabis juice purée, a sweetening agent is optionally added to the cannabis juice purée. The sweetening agent is selected from the group consisting of honey, stevia, fruit juice, sugar, corn syrup, or any other type of food grade sweetener. The sweetening agent provides a frozen ice pop of cannabis juice purée that is more palatable than if the sweetening agent were not included. Flavoring agents are optionally added to the packaged cannabis juice purée, such as fruit flavor, spice (apple, cherry, mint, tart, etc.), or any other type of food grade flavoring. Fruit juice, fruit, or vegetable material may also be added, such as blueberries, blueberry juice, carrots, or carrot juice.

Figure 43:
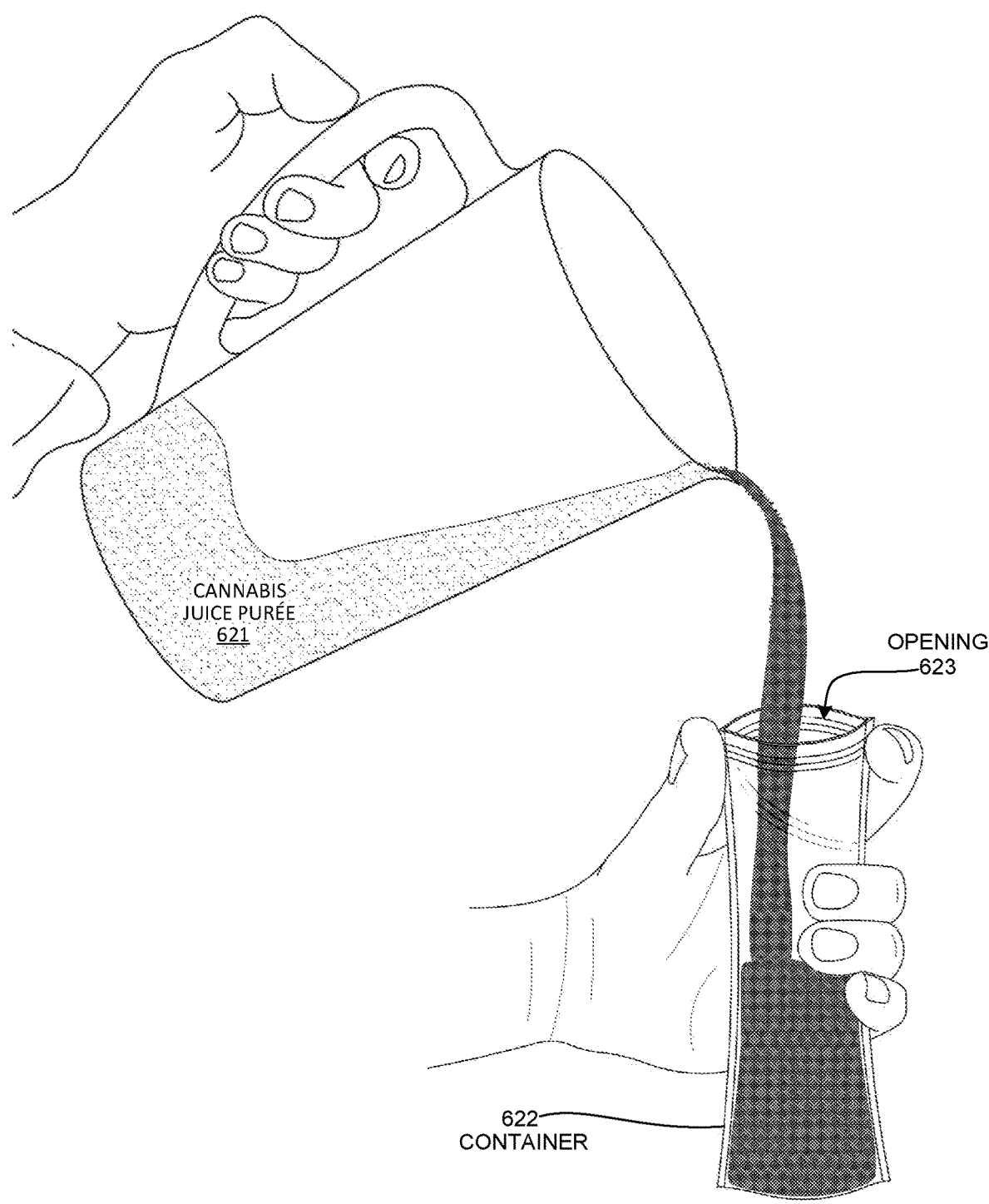
FIG. 43 is a perspective diagram showing how the cannabis juice purée 621 is deposited into container 622.

In a second step (step 620), the cannabis juice purée is deposited into a container. In one example, the container is a tube shaped container made of a flexible material. For example, in FIG. 43, the cannabis juice purée 621 is deposited into container 622 through opening 623. The container 622 is a tube shaped container formed from a thermoplastic polymer such as polypropylene plastic resin. In one example, the opening 623 of the container 622 is resealable. The container 622 with the resealable opening 623 is available from the following internet address: http://zipzicles.com/. In one example, the opening 623 of the container 622 is not resealable and is permanently sealed after the cannabis juice purée 621 is deposited into the container 622.

Figure 44:
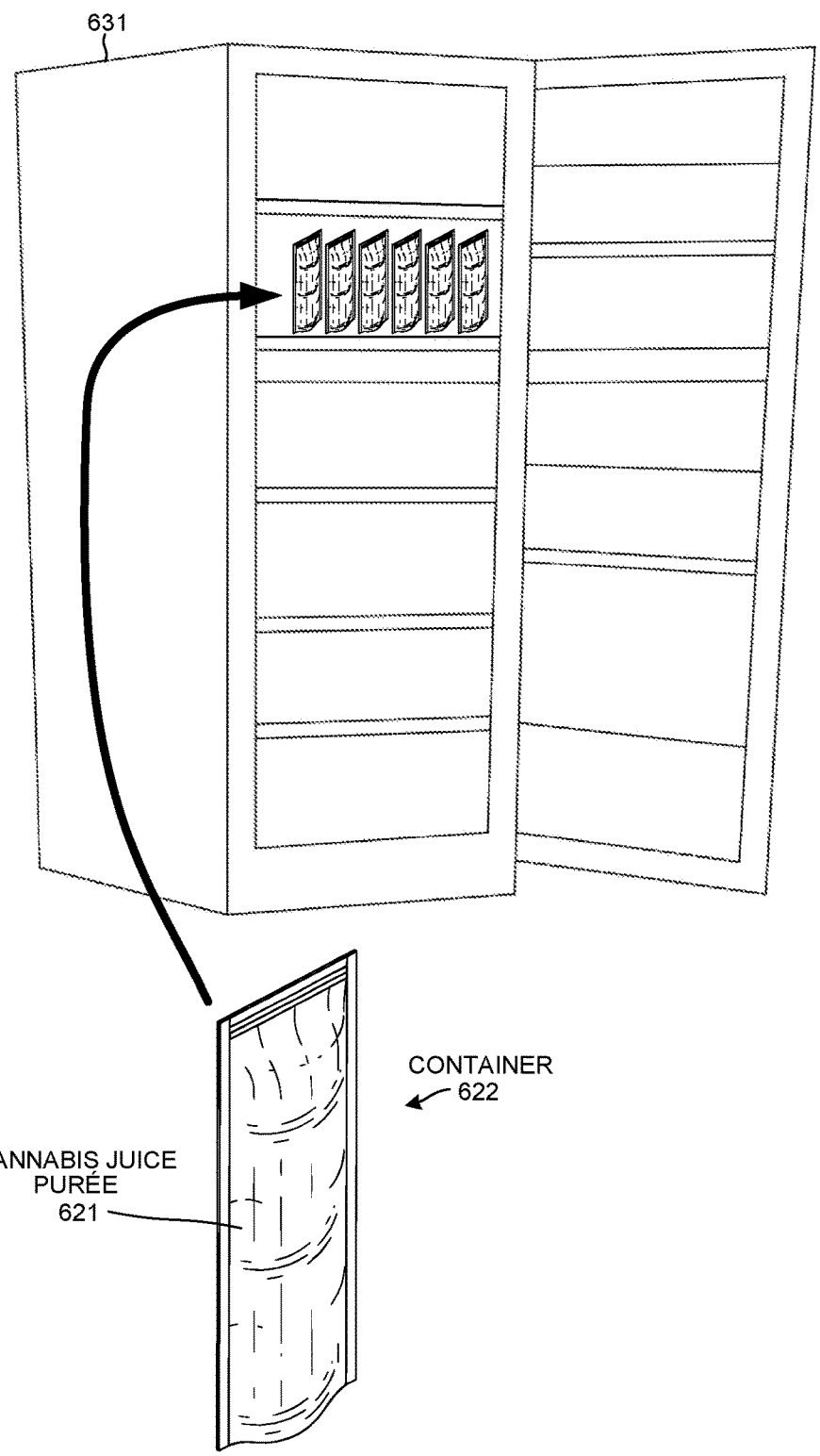
FIG. 44 is a perspective diagram showing how the container 622 having the cannabis juice purée 621 is placed in a freezer 631.

In a third step (step 630), the container having the cannabis juice purée to form a packaged frozen ice pop of cannabis juice purée. For example, in FIG. 44 the container 622 having the cannabis juice purée 621 is placed in a freezer 631 so that the cannabis juice purée 621 in the container 622 can freeze. The temperature within freezer 631 is typically between 0.0° F. and 5.0° F., but may be less than 0.0° F. Freezing the cannabis juice purée promotes preservation because harvested raw cannabis material is not acceptable for consumption after three days, even when the cannabis material is stored in a refrigerator. However, by freezing the cannabis juice purée to form the packaged frozen ice pop of cannabis juice purée, the shelf-life is extended for at least six months if properly stored in a freezer.

Figure 45A:
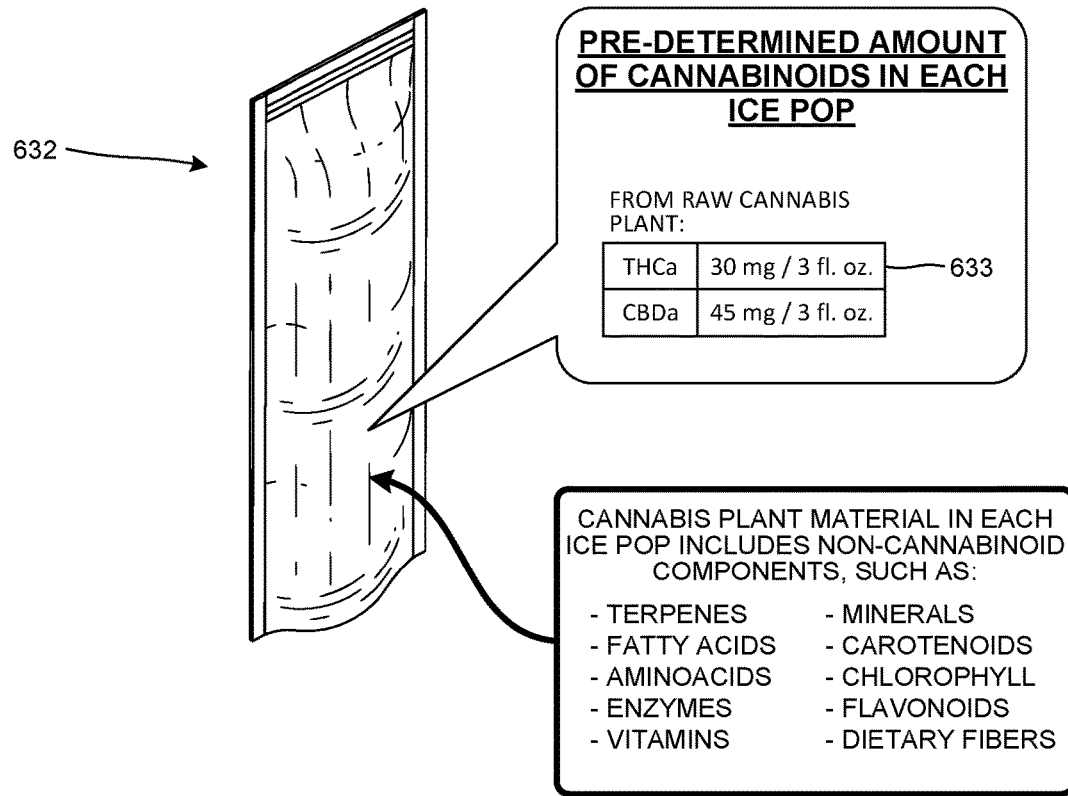
FIG. 45A is a perspective diagram of the packaged frozen ice pop of cannabis juice purée 632 with only non-decarboxylated cannabinoids.

FIG. 45A is a perspective diagram of the packaged frozen ice pop of cannabis juice purée 632 with only non-decarboxylated cannabinoids. The frozen ice pop of cannabis juice purée 632 has a cannabinoid profile 633. The packaged frozen ice pop of cannabis juice purée 632 is formed by carrying out the steps set forth in method 600 such that the cannabis juice purée in the first step (step 610) has only raw, blended cannabis material. None of the collected cannabis material is heated. The packaged frozen ice pop of cannabis juice purée 632 does not include any decarboxylated cannabinoids and the packaged frozen ice pop of cannabis juice purée 632 is not psychoactive. In this example, frozen ice pop of cannabis juice purée 632 has 30 mg of THCa per 3 fluid ounces and 45 mg of CBDa per 3 fluid ounces. The ratio of CBDa to THCa is 3:2. The amount of CBDa in each ice pop is greater than the amount of THCa, and the amount of CBD in each ice pop is greater than the amount of THC. In other embodiments, each ice pop has ratio of CBDa to THCa taken from the group consisting of: 2 CBDa to 1 THCa, 1 CBDa to 1 THCa, 1 CBDa to 2 THCa, 1 CBDa to 3 THCa, 3 CBDa to 1 THCa, 0 CBDa to 1 THCa (no CBDa, only THCa), and 1 CBDa to 0 THCa (no THCa, only CBDa). The frozen ice pop of cannabis juice purée may be made to include or exclude non-cannabinoid components of the cannabis plant that include terpenes, fatty acids, aminoacids, enzymes, vitamins, minerals, carotenoids, chlorophyll, flavonoids, and dietary fibers. In yet other embodiments, the frozen ice pop of cannabis juice purée has between 1 mg and 500 mg of THCa and between 1 mg and 500 mg of CBDa. Non-decarboxylated high concentrate cannabis extract may also be added to the frozen ice pop of cannabis juice purée to achieve high concentrations of non-decarboxylated cannabinoids.

Figure 45B:
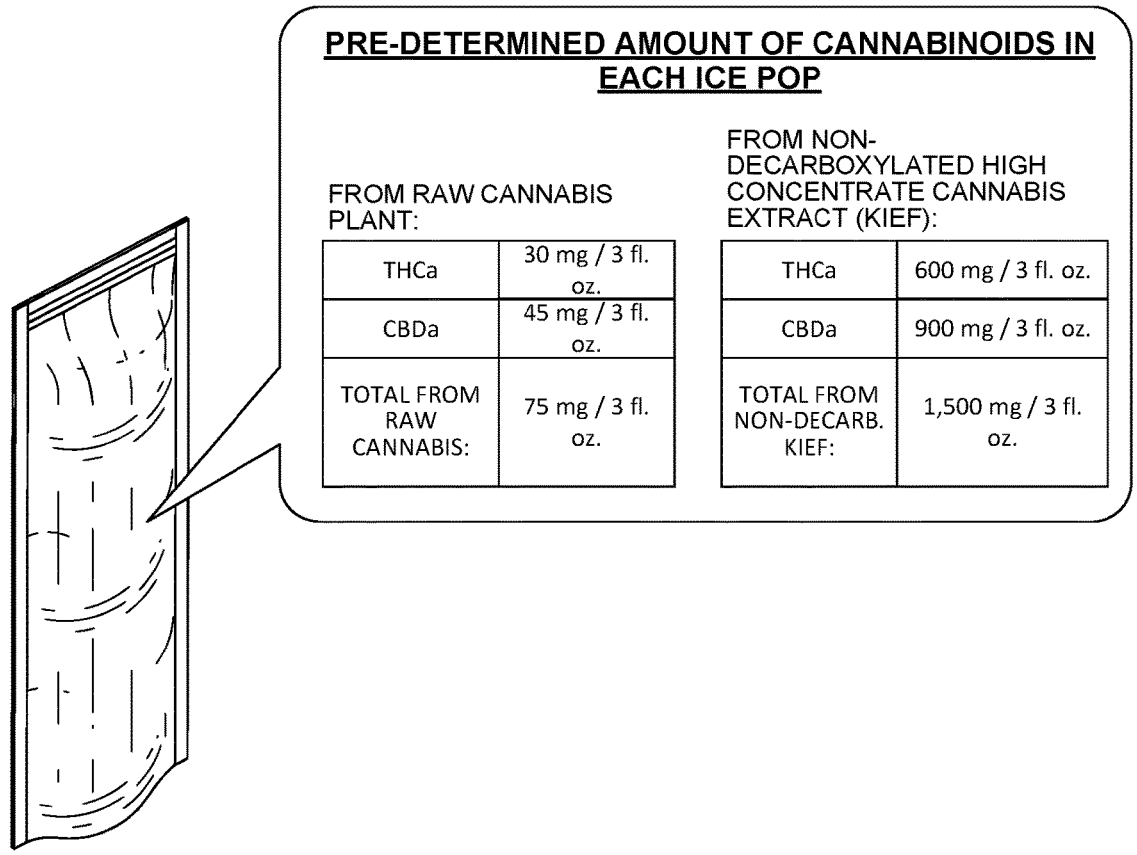
FIG. 45B is a perspective diagram of another embodiment of a packaged frozen ice pop of cannabis juice purée with added non-decarboxylated high concentrate cannabis extract.

FIG. 45B is a perspective diagram of another embodiment of a packaged frozen ice pop of cannabis juice purée with added non-decarboxylated high concentrate cannabis extract. In the example of FIG. 45B, the packaged frozen ice pop of cannabis juice purée has 75 mg of non-decarboxylated cannabinoids from raw cannabis plant and 1,500 mg of non-decarboxylated cannabinoids from non-decarboxylated high concentrate cannabis extract.

Figure 46A:
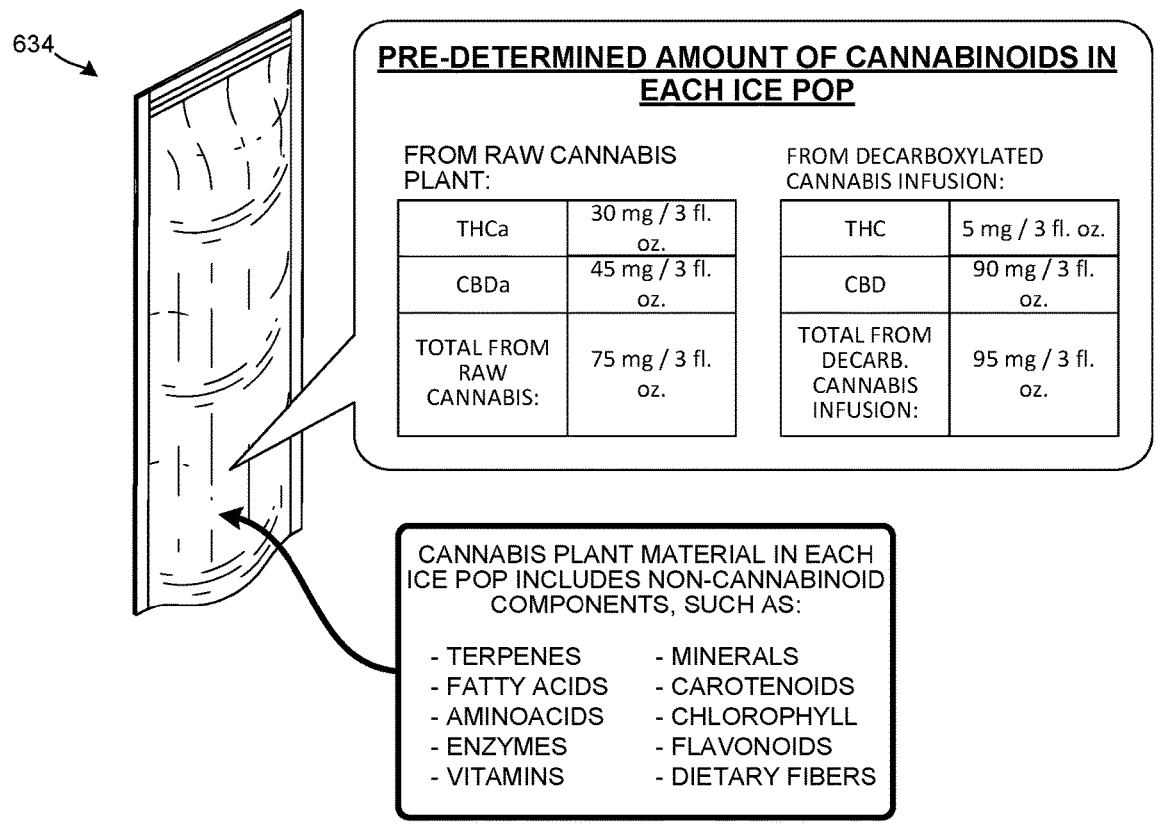
FIG. 46A is a perspective diagram of a packaged frozen ice pop of cannabis juice purée 634 with added decarboxylated cannabinoids.

FIG. 46A is a perspective diagram of a packaged frozen ice pop of cannabis juice purée 634 with added decarboxylated cannabinoids. The packaged frozen ice pop of cannabis juice purée 634 is formed by carrying out the steps set forth in method 600 such that the cannabis juice purée in the first step (step 610) has raw, blended cannabis material in addition to decarboxylated cannabis infusion. The packaged frozen ice pop of cannabis juice purée 634 includes non-decarboxylated cannabinoids and decarboxylated cannabinoids. In this example, packaged frozen ice pop of cannabis juice purée 634 has 75 mg of non-decarboxylated cannabinoids from raw cannabis plant and 95 mg of decarboxylated cannabinoids from decarboxylated cannabis infusion.

FIG. 46B is a perspective diagram of another embodiment of a packaged frozen ice pop of cannabis juice purée with added decarboxylated cannabis infusion and non-decarboxylated high concentrate cannabis extract. In the example of FIG. 46B, the packaged frozen ice pop of cannabis juice purée has 75 mg of non-decarboxylated cannabinoids from raw cannabis plant, 95 mg of decarboxylated cannabinoids from decarboxylated cannabis infusion, and 1,500 mg of non-decarboxylated cannabinoids from non-decarboxylated high concentrate cannabis extract.

Figure 46C:
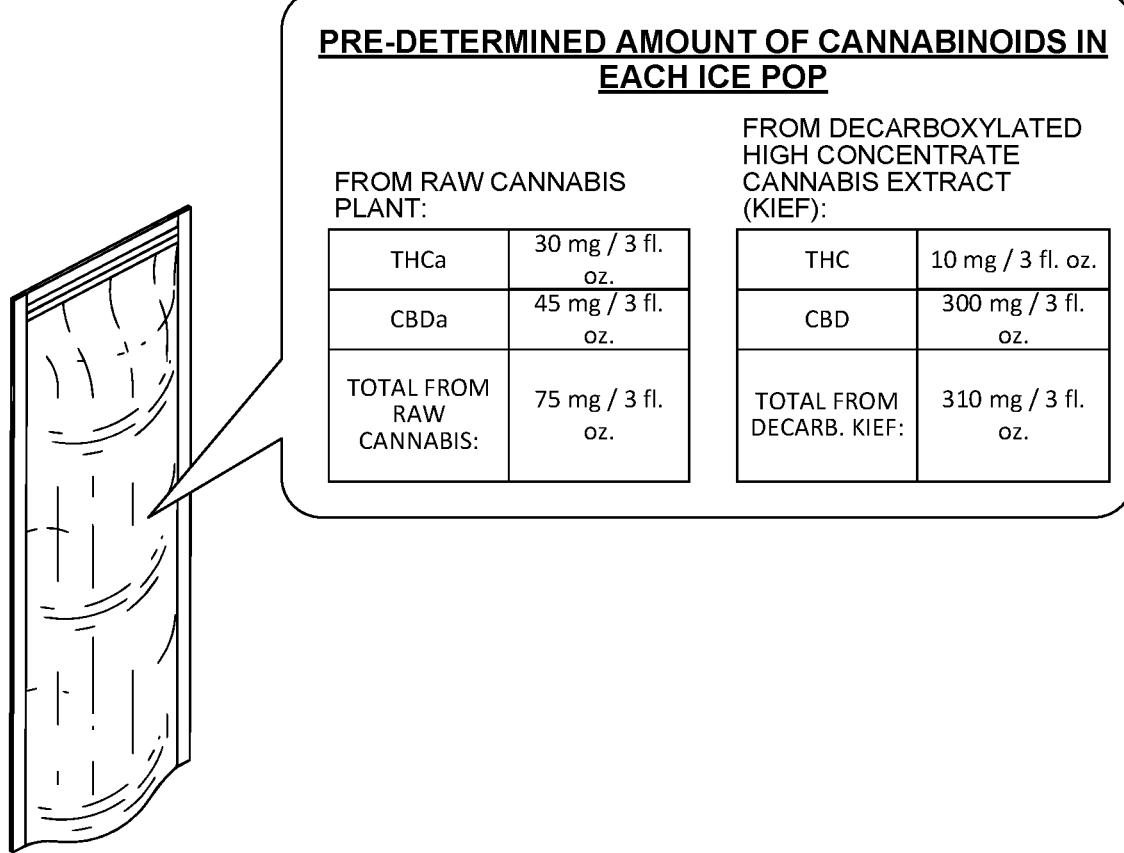
FIG. 46C is a perspective diagram of another embodiment of a packaged frozen ice pop of cannabis juice purée with added decarboxylated high concentrate cannabis extract.

FIG. 46C is a perspective diagram of another embodiment of a packaged frozen ice pop of cannabis juice purée with added decarboxylated high concentrate cannabis extract. In the example of FIG. 46C, the packaged frozen ice pop of cannabis juice purée has 75 mg of non-decarboxylated cannabinoids from raw cannabis plant and 310 mg of decarboxylated cannabinoids from decarboxylated high concentrate cannabis extract.

FIG. 46D is a perspective diagram of another embodiment of a packaged frozen ice pop of cannabis juice purée with added decarboxylated high concentrate cannabis extract and non-decarboxylated high concentrate cannabis extract. In the example of FIG. 46D, the packaged frozen ice pop of cannabis juice purée has 75 mg of non-decarboxylated cannabinoids from raw cannabis plant, 310 mg of decarboxylated cannabinoids from decarboxylated high concentrate cannabis extract, and 1,500 mg of non-decarboxylated cannabinoids from non-decarboxylated high concentrate cannabis extract.

Figure 47:
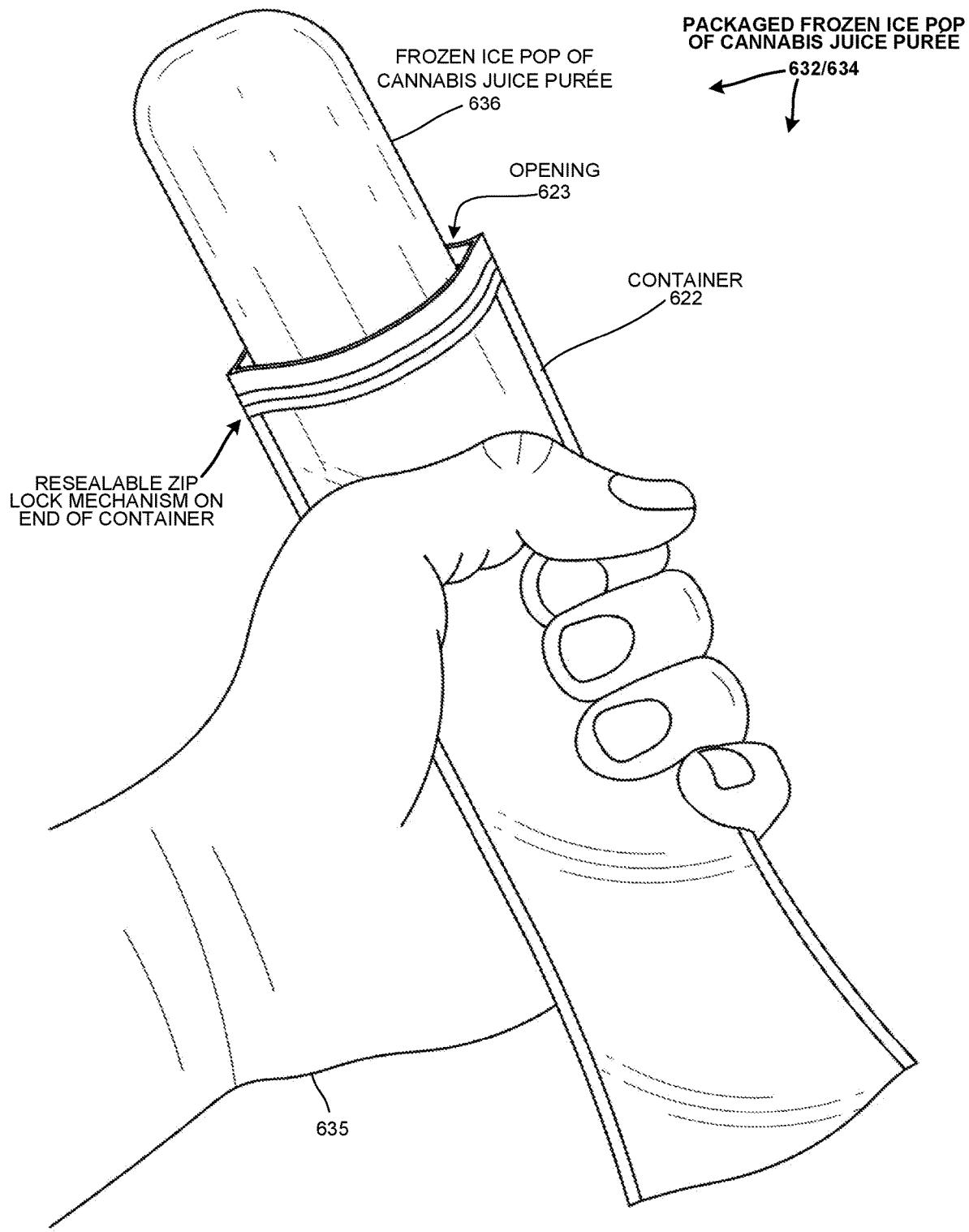
FIG. 47 is a diagram of a user 635 consuming the packaged frozen ice pop of cannabis juice purée 632/634.

FIG. 47 is a diagram of a user 635 consuming the packaged frozen ice pop of cannabis juice purée 632/634. The user 635 opens the top of the container 622 thereby forming an opening 623. The frozen ice pop of cannabis juice purée 636 passes through the opening for the user 635 to consume. In this example the opening 623 is resealable such that the user 635 can consume a portion of the packaged frozen ice pop of cannabis juice purée 632/634, reseal the top, and store the partially consumed packaged frozen ice pop of cannabis juice purée 632/634 in a freezer for future consumption.

FIG. 48 is a diagram of a side view of the packaged frozen ice pop of cannabis juice purée 632/634. The container 622 has an upper extent 637, a lower extent 638, a first side extent 639, and a second side extent 640. The frozen ice pop of cannabis juice purée 636 is disposed within an inner portion 641. The frozen ice pop of cannabis juice purée 636 directly contacts the inner portion 641 of container 622. No packaging material is disposed between the frozen ice pop of cannabis juice purée 636 and the inner portion 641 of container 622. The packaged frozen ice pop of cannabis juice purée 632/634 includes a resealable mechanism 642. The resealable mechanism 642 is similar to the resealable mechanisms provided in zipper storage bags or slider storage bags.

In this example, the packaged frozen ice pop of cannabis juice purée 632/634 is between 1.0 to 2.0 inches wide (dimension of upper and lower extents 637/638) and between 7.0 and 9.0 inches long (dimension of side extents 639/640). Each of the first and second side extents 639 and 640 is at least three times a length of each of the upper and lower extents 637 and 638. The upper extent 637 extends parallel to the lower extent 638. The first side extent 639 extends parallel to the second side extents 640. The packaged frozen ice pop of cannabis juice purée 632/634 has a rectangular shaped when viewed from the side perspective of FIG. 48.

FIG. 49 is a diagram of a top view of the packaged frozen ice pop of cannabis juice purée 632/634. The packaged frozen ice pop of cannabis juice purée 632/634 has an edge portion 643 having a first thickness 644. The packaged frozen ice pop of cannabis juice purée 632/634 has a center portion 645 having a second thickness 646. The second thickness 646 is at least ten times the first thickness 644. The packaged frozen ice pop of cannabis juice purée 632/634 has an oval shape when viewed from the top perspective of FIG. 49.

FIG. 50 is a diagram of a side view of another embodiment of a packaged frozen ice pop of cannabis juice purée 650 having a container 651 that is not resealable. A frozen ice pop of cannabis juice purée 652 is disposed within container 651. The packaged frozen ice pop of cannabis juice purée 650 has a top portion 653 that does not include a resealable mechanism as in the packaged frozen ice pop of cannabis juice purée 632/634 shown in FIG. 47. A user tears the top portion 653 of the container 651 to provide an opening so that the frozen ice pop of cannabis juice purée 652 passes through the opening and is consumed by the user.

Figure 51:
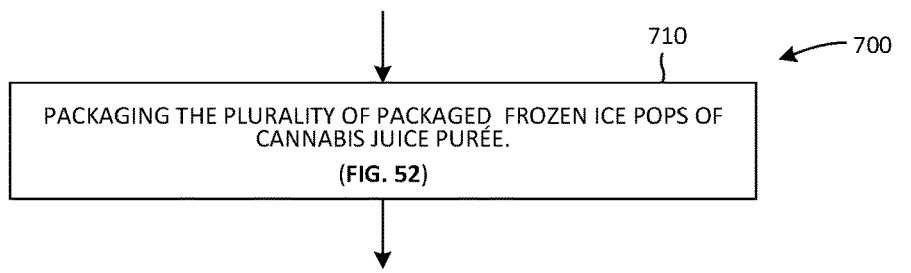
FIG. 51 is a flowchart of a method 700 to package a plurality of packaged frozen ice pops of cannabis juice purées.
Figure 52:
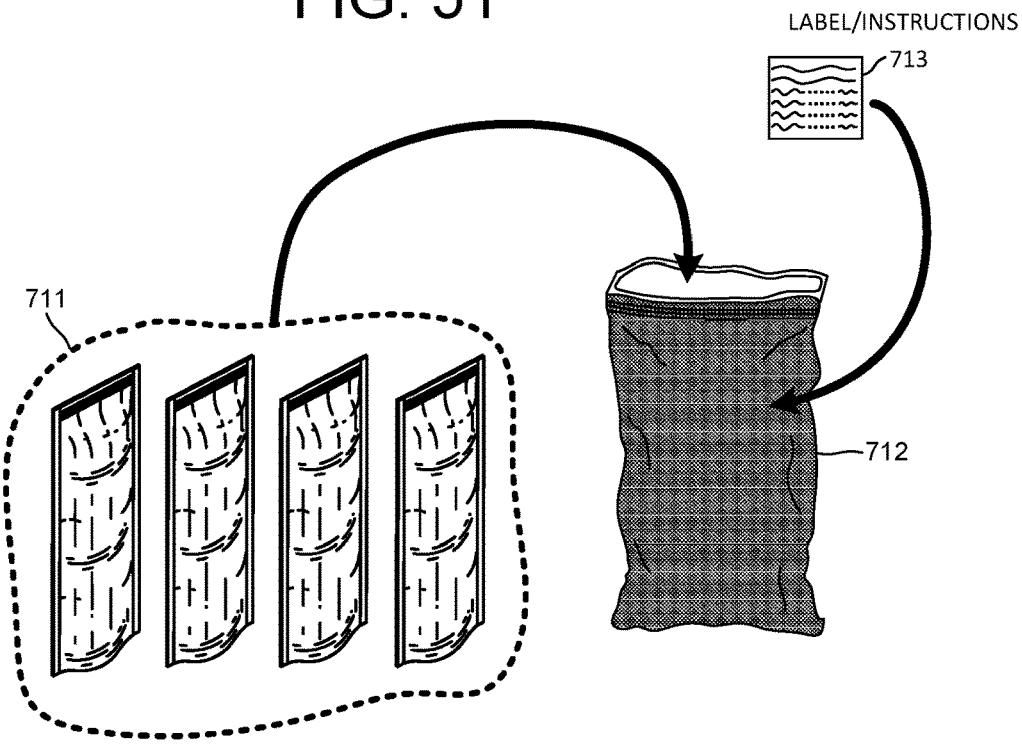
FIG. 52 is a perspective diagram showing how a plurality of packaged frozen ice pops of cannabis juice purées 711 is placed inside a package 712.

FIG. 51 is a flowchart of a method 700 to package a plurality of packaged frozen ice pops of cannabis juice purée. In a first step (step 710), a plurality of packaged frozen ice pops of cannabis juice purée is packaged into a container. For example, in FIG. 52, a plurality of packaged frozen ice pops of cannabis juice purée 711 is placed inside a package 712. The plurality of packaged frozen ice pops of cannabis juice purée 711 is disposed within the package 712. An amount of instructions is included with the package. In one example, the amount of instructions is provided on a label 713 affixed or printed directly onto the package and instructs the user on the types and amounts of cannabinoids present in each frozen ice pop of cannabis juice purée. In another example, a label is also printed or affixed onto each of the plurality of packaged frozen ice pops of cannabis juice purée 711. The amount of instructions may also instruct a user on how to consume the frozen ice pop of cannabis juice purée as well as provide information regarding health benefits and possible side effects.

Figure 53:
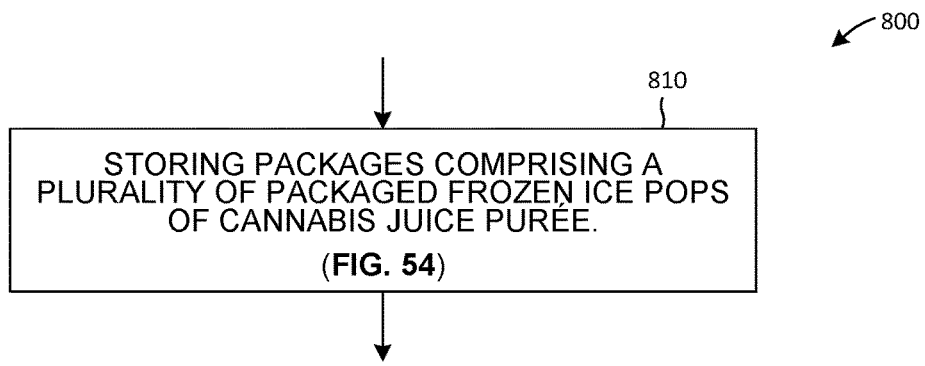
FIG. 53 is a flowchart of a method 800 to store packages comprising a plurality of packaged frozen ice pops of cannabis juice purée.
Figure 54:
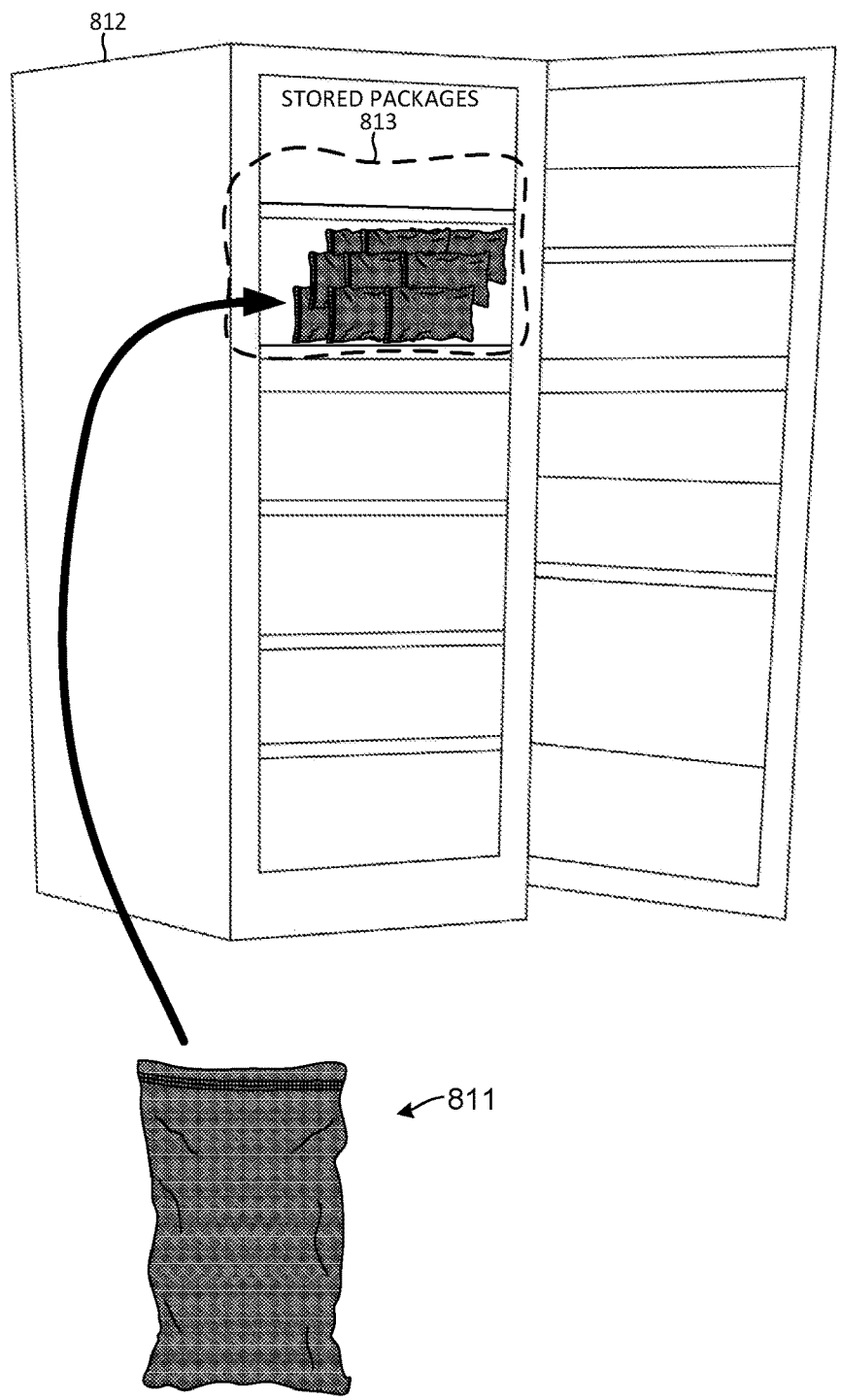
FIG. 54 is a perspective diagram showing how a plurality of packages 811 are stored in a freezer 812.

FIG. 53 is a flowchart of a method 800 to store packages comprising a plurality of packaged frozen ice pops of cannabis juice purée. For example, in a first step (step 810), a plurality of packaged frozen ice pops of cannabis juice purée are stored at a temperature that prevents the packaged frozen ice pops of cannabis juice purée from melting. For example, in FIG. 54, a plurality of packages 811 is stored in a freezer 812. The packages 811 are stored by arranging each package in a compartment of the freezer 812. The stored packages 813 are stored until they are to be distributed to dispensaries or users.

Figure 55:
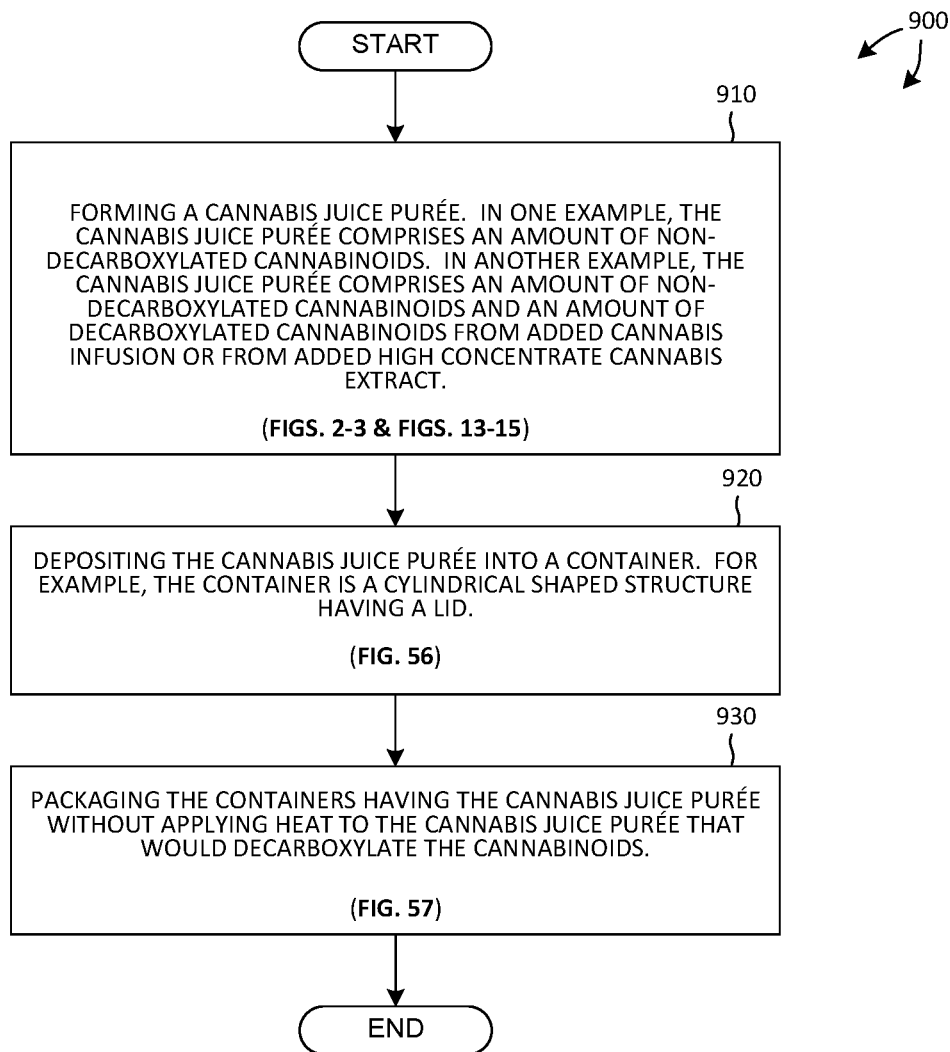
FIG. 55 is a flowchart of a method 900 in accordance with fourth embodiment.

FIG. 55 is a flowchart of a method 900 in accordance with a fourth embodiment. The method 900 is a method of manufacturing and packaging a cannabis juice purée. In one specific embodiment, the packaged cannabis juice purée has an amount of non-decarboxylated cannabinoids and is non-psychoactive. In another specific embodiment, the packaged cannabis juice purée has an amount of non-decarboxylated cannabinoids and an amount of decarboxylated cannabinoids. The amount of decarboxylated cannabinoids in each packaged cannabis juice purée is at least 5 mg. The packaged cannabis juice purée is not frozen and can be stored at room temperature or in a refrigerator until opened.

In a first step (step 910), a cannabis juice purée is formed. To form a packaged cannabis juice purée that is non-psychoactive, raw cannabis material having an amount of non-decarboxylated cannabinoids is collected. For example, in FIG. 2, raw cannabis material 112 is collected by trimming leaves 113 from the cannabis plant 111, and in FIG. 3, the raw cannabis material 112 is blended in a blender 121 with water 122 and a thickening agent 123 to form a cannabis juice purée.

To form a packaged cannabis juice purée that is psychoactive, a portion of the collected raw cannabis material is heated. For example, in FIG. 13, raw cannabis material 211 is collected from a first cannabis plant 212 and a second cannabis plant 213. A first portion 214 of the raw cannabis material 211 is obtained from the first cannabis plant 212. Next, the first portion of raw cannabis material 214 is blended in a blender 221 with water 222 and a thickening agent 223 to form a non-decarboxylated cannabis juice purée as shown in FIG. 14. Next, a second portion 216 of the raw cannabis material 211 is obtained from the second cannabis plant 213 as shown in FIG. 13. Next, the second portion of collected raw cannabis material is heated, as shown for example in FIG. 15. The non-decarboxylated cannabis juice purée is combined with the decarboxylated cannabis juice purée prior to packaging.

In both the non-decarboxylated embodiment and the decarboxylated embodiment of the packaged cannabis juice purée, a sweetening agent or flavoring agent is optionally added to the cannabis juice purée. The sweetening agent is selected from the group consisting of honey, stevia, fruit juice, sugar, corn syrup, or any other type of food grade sweetener. The sweetening agent provides a cannabinoid juice blend that is more palatable than if the sweetening agent were not included. Flavoring agents are optionally added to the packaged cannabis juice purée, such as fruit flavor, spice (apple, cherry, mint, tart, etc.), or any other type of food grade flavoring. Fruit juice, fruit, or vegetable material may also be added, such as blueberries, blueberry juice, carrots, or carrot juice.

Figure 56:
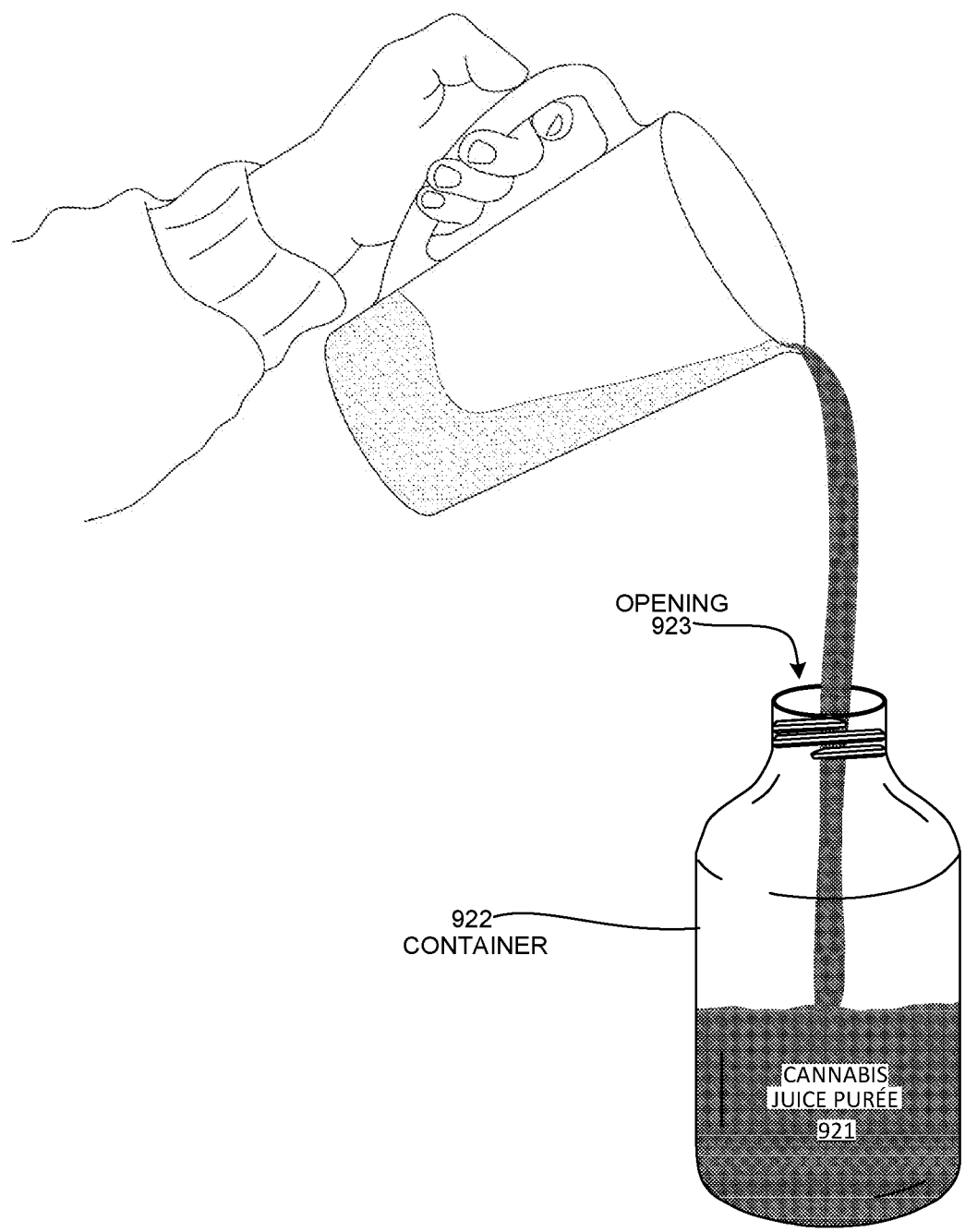
FIG. 56 is a perspective diagram showing how the cannabis juice purée 921 is deposited into a container 922.

In a second step (step 920), the cannabis juice purée is deposited into a container. In one example, the container is a cylindrical shaped structure having a lid. The container 921 is formed from a glass material, a plastic material, or a paper-based material. For example, in FIG. 56, the cannabis juice purée 921 is deposited into a container 922 through opening 923.

Figure 57:
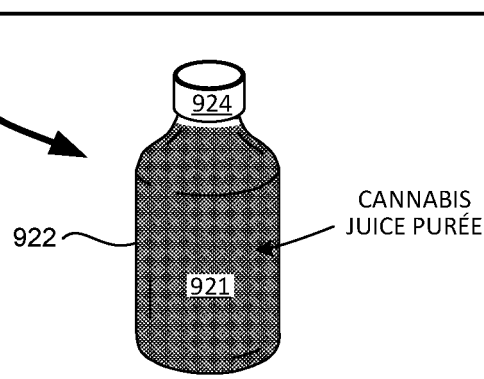
FIG. 57 is a perspective diagram of performing high pressure processing (HPP) during the packaging of the cannabis juice purée 921.

In a third step (step 930), the container having the cannabis juice purée is packaged without heating the cannabis juice purée. For example, in FIG. 57, the cannabis juice purée 921 is packaged using high pressure processing (HPP) without applying heat thereby preventing the cannabis juice purée 921 from decarboxylating during the packaging process. Conventional pasteurization methods, on the other hand, apply heat which may undesirably decarboxylate the cannabinoids in the cannabis juice purée.

During the HPP process, the cannabis juice purée 921 is loaded into a high pressure chamber filled with pressure transmitting fluid. In one example, the pressure transmitting fluid is water. The generated pressure is applied to the cannabis juice purée 921. A lid 924 is used to seal the opening 923 of the container 922. For additional information on HPP, see: (1) U.S. Pat. No. 9,277,763, entitled "Biopreservation Methods For Beverages And Other Foods", filed Jun. 23, 2014 by Beckman et al.; (2) U.S. Pat. No. 7,906,160, entitled "Protein beverage and method of making the same", filed Mar. 7, 2007 by Sherwood et al.; and (3) U.S. Pat. No. 5,232,726, entitled "Ultra-high pressure homogenization of unpasteurized juice", filed Oct. 8, 1992 by Clark et al. (the subject matter of these patent documents is incorporated herein in its entirety).

Figure 58A:
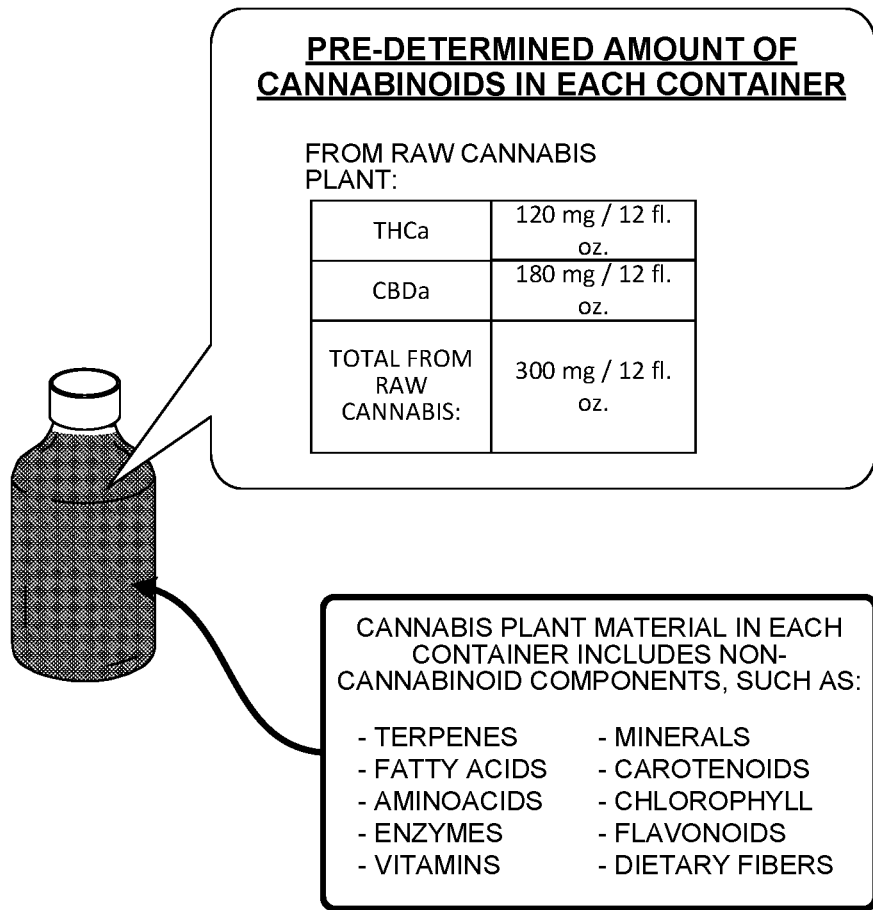
FIG. 58A is a perspective diagram of the packaged cannabis juice purée with only non-decarboxylated cannabinoids.

FIG. 58A is a perspective diagram of the packaged cannabis juice purée with only non-decarboxylated cannabinoids. The packaged cannabis juice purée has 120 mg of THCa and 180 mg of CBDa. The packaged cannabis juice purée is formed by carrying out the steps set forth in method 900 such that the cannabis juice purée in the first step (step 910) has only raw, blended cannabis material. None of the collected cannabis material is heated. The packaged cannabis juice purée does not include any decarboxylated cannabinoids and the packaged cannabis juice purée is not psychoactive. In this example, the ratio of CBDa to THCa is 3:2. The amount of CBDa in each packaged cannabis juice purée is greater than the amount of THCa, and the amount of CBD in each packaged cannabis juice purée is greater than the amount of THC. In other embodiments, each packaged cannabis juice purée has ratio of CBDa to THCa taken from the group consisting of: 2 CBDa to 1 THCa, 1 CBDa to 1 THCa, 1 CBDa to 2 THCa, 1 CBDa to 3 THCa, 3 CBDa to 1 THCa, 0 CBDa to 1 THCa (no CBDa, only THCa), and 1 CBDa to 0 THCa (no THCa, only CBDa). The packaged cannabis juice purée may be made to include or exclude non-cannabinoid components of the cannabis plant that include terpenes, fatty acids, aminoacids, enzymes, vitamins, minerals, carotenoids, chlorophyll, flavonoids, and dietary fibers. Non-decarboxylated high concentrate cannabis extract may also be added to the packaged cannabis juice purée to achieve high concentrations of non-decarboxylated cannabinoids.

FIG. 58B is a perspective diagram of another embodiment of a packaged cannabis juice purée with added non-decarboxylated high concentrate cannabis extract. In the example of FIG. 58B, the packaged cannabis juice purée has 300 mg of non-decarboxylated cannabinoids from raw cannabis plant and 6,000 mg of non-decarboxylated cannabinoids from non-decarboxylated high concentrate cannabis extract.

Figure 59A:
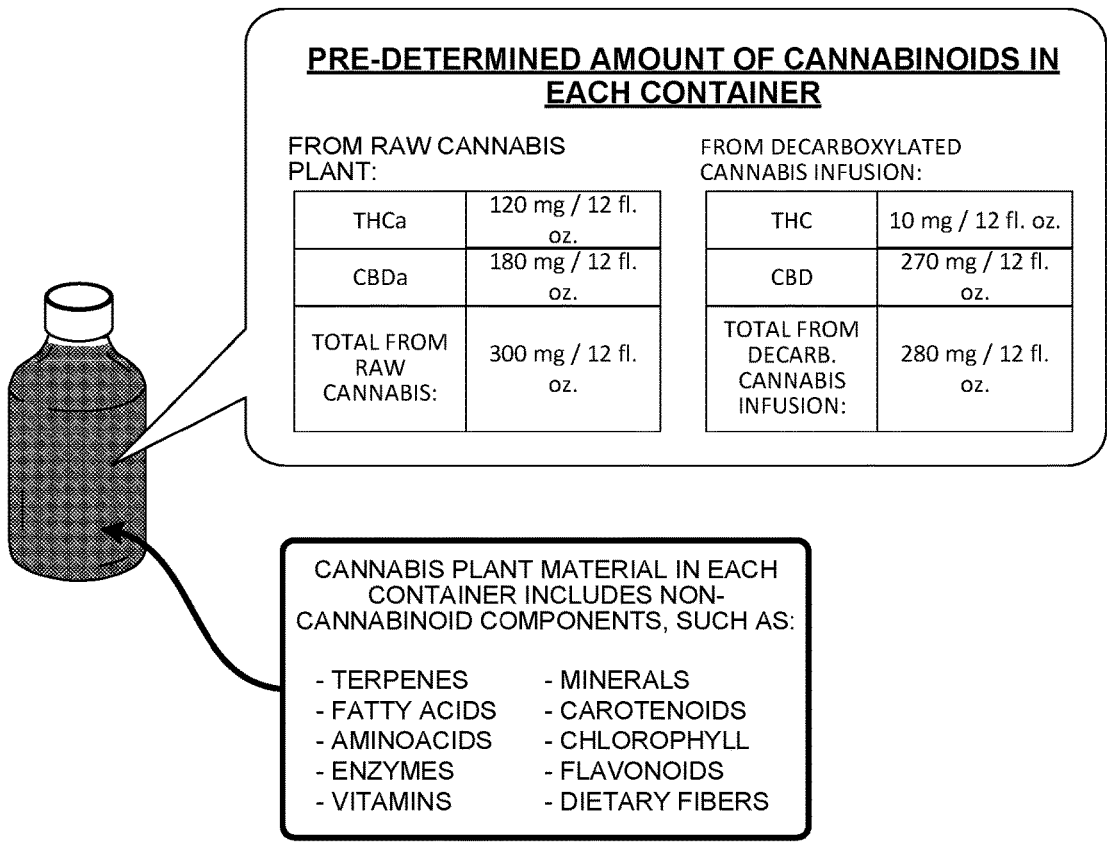
FIG. 59A is a perspective diagram of a packaged cannabis juice purée having decarboxylated cannabinoids.

FIG. 59A is a perspective diagram of a packaged cannabis juice purée with added decarboxylated cannabinoids. The packaged frozen ice pop of cannabis juice purée 634 is formed by carrying out the steps set forth in method 900 such that the cannabis juice purée in the first step (step 910) has raw, blended cannabis material in addition to decarboxylated cannabis infusion. The packaged cannabis juice purée includes non-decarboxylated cannabinoids and decarboxylated cannabinoids. In this example, packaged cannabis juice purée has 300 mg of non-decarboxylated cannabinoids from raw cannabis plant and 280 mg of decarboxylated cannabinoids from decarboxylated cannabis infusion.

FIG. 59B is a perspective diagram of another embodiment of a packaged cannabis juice purée with added decarboxylated cannabis infusion and non-decarboxylated high concentrate cannabis extract. In the example of FIG. 59B, the packaged cannabis juice purée has 300 mg of non-decarboxylated cannabinoids from raw cannabis plant, 280 mg of decarboxylated cannabinoids from decarboxylated cannabis infusion, and 6,000 mg of non-decarboxylated cannabinoids from non-decarboxylated high concentrate cannabis extract.

FIG. 59C is a perspective diagram of another embodiment of a packaged cannabis juice purée with added decarboxylated high concentrate cannabis extract. In the example of FIG. 59C, the packaged cannabis juice purée has 300 mg of non-decarboxylated cannabinoids from raw cannabis plant and 310 mg of decarboxylated cannabinoids from decarboxylated high concentrate cannabis extract.

FIG. 59D is a perspective diagram of another embodiment of a packaged cannabis juice purée with added decarboxylated high concentrate cannabis extract and non-decarboxylated high concentrate cannabis extract. In the example of FIG. 59D, the packaged cannabis juice purée has 300 mg of non-decarboxylated cannabinoids from raw cannabis plant, 310 mg of decarboxylated cannabinoids from decarboxylated high concentrate cannabis extract, and 6,000 mg of non-decarboxylated cannabinoids from non-decarboxylated high concentrate cannabis extract.

Figure 60:
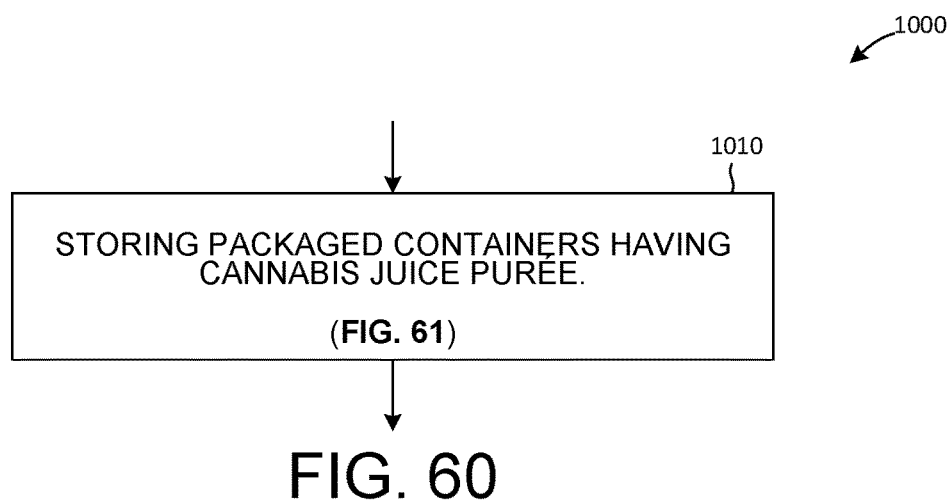
FIG. 60 is a flowchart of a method 1000 to store packaged containers having a cannabis juice purée.
Figure 61:
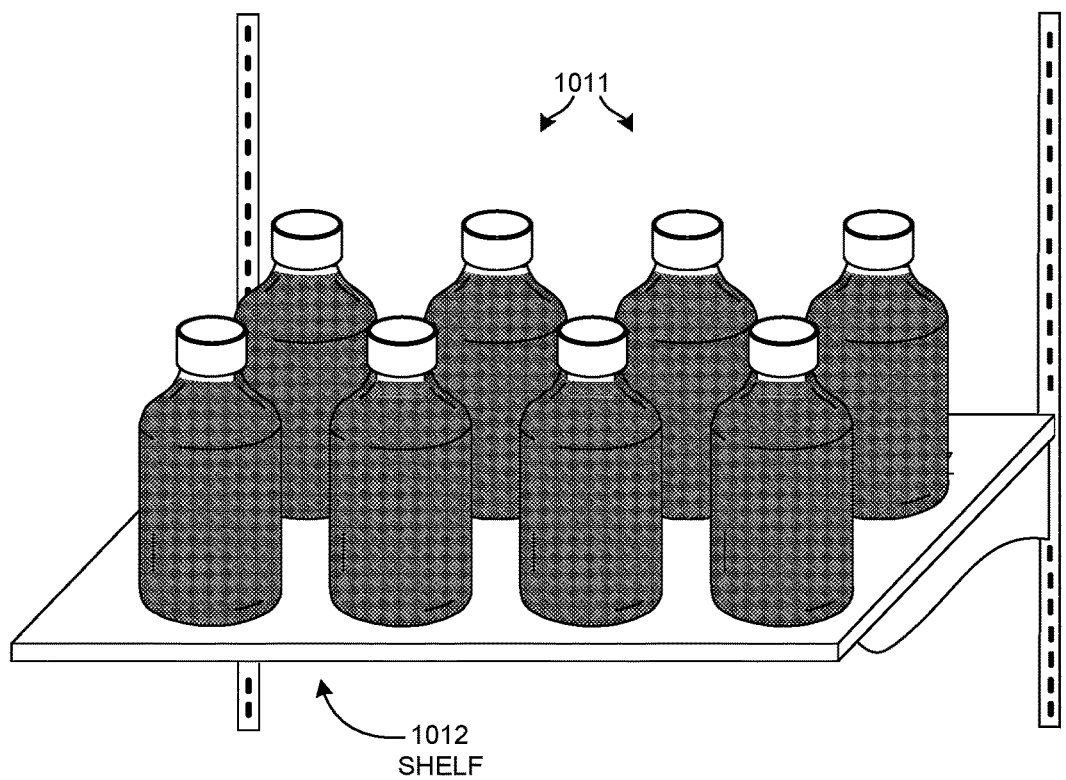
FIG. 61 is a perspective diagram of containers 1011 each having a cannabis juice purée that are stored on a shelf 1012.

FIG. 60 is a flowchart of a method 1000 to store packaged containers having a cannabis juice purée. In a first step (step 1010), packaged containers having a cannabis juice purée are stored. For example, in FIG. 61, containers 1011 each having a cannabis juice purée are stored on a shelf 1012. The shelf 1012 may be part of a retail-store, a dispensary, a storage facility, or a transport vehicle.

FIG. 62 is a table 1100 that shows the therapeutic benefits of various types of cannabinoids. The amount and type of cannabinoid present in each of the embodiments can vary depending on the specific therapeutic benefits being targeted. The cannabis juice purée used in the various embodiments has at least one type of cannabinoid listed in table 1100.

Although certain specific embodiments are described above for instructional purposes, the teachings of this patent document have general applicability and are not limited to the specific embodiments described above. For example, in addition to THC and CBD, other combinations of cannabinoids can be employed. For example, CBG is another cannabinoid that can be present in certain strains of cannabis. Non-decarboxylated CBG (CBGa) and decarboxylated CBG (CBG) can be used in forming the cannabis juice purée. In addition, CBN is another cannabinoid that can be present in certain strains of cannabis. Non-decarboxylated CBN (CBNa) and decarboxylated CBN (CBN) can be used in forming the cannabis juice purée. In addition, other cannabis strains with various terpene profiles can be added to the cannabis juice purée in the various embodiments. Accordingly, various modifications, adaptations, and combinations of various features of the described embodiments can be practiced without departing from the scope of the invention as set forth in the claims.

What is claimed is:

1. A container comprising:
    a frozen structure of cannabis juice purée, wherein the cannabis juice purée is formed by blending cannabis plant material of a cannabis plant, wherein all of the cannabis plant material is converted into the cannabis juice purée, wherein each frozen structure of cannabis juice purée has cannabinoids that include at least one of decarboxylated cannabinoids or non-decarboxylated cannabinoids, wherein the frozen structure is disposed within an inner portion of the container, wherein the container has an upper extent, a bottom extent, a first side extent, and a second side extent, wherein the first side extent extends along a first side of the container from the upper extent to the bottom extent, wherein the second side extent extends along a second side of the container from the upper extent to the bottom extent, and wherein the first side is opposite the second side.

2. The container of claim 1, wherein the frozen structure of cannabis juice purée is an ice pop of cannabis juice purée, and wherein the ice pop includes at least one of decarboxylated high concentrate cannabis extract, non-decarboxylated high concentrate cannabis extract, decarboxylated cannabis infusion, or heated cannabis material.

3. The container of claim 1, wherein the container is formed from a flexible material, wherein the upper extent is adapted to form an opening such that an inner portion of the container is exposed, and wherein the first side extent is at least three times a length of the upper extent.

4. The container of claim 1, wherein the frozen structure directly contacts the inner portion, and wherein no packaging material is disposed between the frozen structure and the inner portion of the container.

5. The container of claim 1, wherein the first side extent is parallel to the second side extent, and wherein the upper extent is parallel to the bottom extent.

6. The container of claim 1, wherein an edge portion of the container has a first thickness, wherein a center portion of the container has a second thickness, and wherein the second thickness is more than ten times the first thickness.

7. The container of claim 1, wherein cannabinoids include only non-decarboxylated cannabinoids, and wherein the cannabinoids does not include any decarboxylated cannabinoids.

8. The container of claim 1, wherein the cannabinoids include at least one cannabinoid taken from the group consisting of: cannabigerolic acid (CBGa), cannabigerovarin acid (CBGVA), tetrahydrocannabinolic acid (THCA), tetrahydrocannabivarin carboxylic acid (THCVA), cannabidiolic acid (CBDA), cannabidivarin acid (CBDVA), cannabichrome carboxylic acid (CBCA), cannabichrome varinic acid (CBCVA), tetrahydrocannabinol (THC), tetrahydrocannabivarin (THCV), tetrahydrocannabivarin acid (THVA), cannabidiol (CBD), cannabidivarin (CBDV), cannabichromene (CBC), cannabichromevarin (CBCV), cannabigerol (CBG), cannabigerovarin (CBGV), cannabinerolic acid (CBNA), cannabigerovarinic acid (CBNVA), cannabinol (CBN), cannabicyclol (CBL), and cannabicyclol acid (CBLA).

9. A method comprising:
(a) forming a cannabis juice purée, wherein the cannabis juice purée is formed by blending raw cannabis material, wherein all of the raw cannabis material is converted into the cannabis juice purée, and wherein the cannabis juice purée has cannabinoids;

(b) depositing the cannabis juice purée into a container without separating the blended raw cannabis material from juice of the cannabis plant; and
(c) freezing the container with the cannabis juice purée to form a packaged ice pop of cannabis juice purée.

10. The method of claim 9, wherein the forming of (a) involves blending the raw cannabis material with a thickening agent.

11. The method of claim 10, wherein the thickening agent is taken from the group consisting of: banana, avocado, psyllium husk, tapioca, and a food-grade thickening agent, wherein the forming of (a) further involves adding a sweetening agent, a flavoring agent, fruits, or vegetables to the cannabis juice purée, wherein the sweetening agent is taken from the group consisting of: honey, stevia, fruit juice, sugar, corn syrup, and a food grade sweetener, and wherein the flavoring agent is taken from the group consisting of: fruit flavoring and a spice.

12. The method of claim 9, further comprising:
(d) placing the packaged ice pop of cannabis juice purée into a package along with other packaged ice pops of cannabis juice purée, wherein the package includes a label that provides cannabinoid profile information of the ice pops of cannabis juice purée; and
(e) storing the package of packaged ice pops in a freezing temperature environment thereby maintaining the ice pops in a solid state.

13. The method of claim 9, wherein prior to the freezing of (c) at least one of decarboxylated high concentrate cannabis extract, non-decarboxylated high concentrate cannabis extract, decarboxylated cannabis infusion, or heated cannabis material is combined with the cannabis juice purée.

14. The method of claim 9, wherein the container is a plastic tube, wherein an end of the plastic tube has an opening, wherein the cannabis juice purée deposited in (b) passes through the opening into the inside of the container, and wherein the opening is selected from the group consisting of: a resealable opening, and a non-resealable opening.

15. The method of claim 9, wherein the cannabinoids include at least one of decarboxylated cannabinoids or non-decarboxylated cannabinoids.

16. The method of claim 9, wherein the packaged ice pop of cannabis juice purée has an upper extent, a lower extent, a first side extent, and a second side extent, wherein an end of the packaged ice pop of cannabis juice purée is adapted to form an opening such that the ice pop passes through the opening to be consumed, and wherein a length of the first side extent is more than three times a length of the upper extent.

* * * * *